US009695233B2

(12) United States Patent
Duerr et al.

(10) Patent No.: US 9,695,233 B2
(45) Date of Patent: Jul. 4, 2017

(54) BISPECIFIC ANTI-VEGF/ANTI-ANG-2 ANTIBODIES AND THEIR USE IN THE TREATMENT OF OCULAR VASCULAR DISEASES

(71) Applicant: Roche Glycart AG, Schlieren (CH)

(72) Inventors: Harald Duerr, Starnberg (DE); Frank Herting, Penzberg (DE); Christian Klein, Bonstetten (CH); Joerg Thomas Regula, Munich (DE); Matthias Rueth, Penzberg (DE); Kay-Gunnar Stubenrauch, Penzberg (CH)

(73) Assignee: ROCHE GLYCART AG (CH)

( * ) Notice: Subject to any disclaimer, the term of this patent is extended or adjusted under 35 U.S.C. 154(b) by 0 days.

(21) Appl. No.: 13/940,091

(22) Filed: Jul. 11, 2013

(65) Prior Publication Data
US 2014/0017244 A1 Jan. 16, 2014

(30) Foreign Application Priority Data

Jul. 13, 2012 (EP) ................................. 12176299

(51) Int. Cl.
*C07K 16/22* (2006.01)
*A61K 39/395* (2006.01)
*A61K 39/00* (2006.01)

(52) U.S. Cl.
CPC ........ *C07K 16/22* (2013.01); *A61K 2039/505* (2013.01); *C07K 2317/31* (2013.01); *C07K 2317/52* (2013.01); *C07K 2317/56* (2013.01); *C07K 2317/92* (2013.01)

(58) Field of Classification Search
CPC ............ C07K 2317/31; C07K 2317/52; C07K 2317/56; C07K 2317/71; C07K 2317/72; C07K 2317/92; C07K 2317/94; C07K 2317/76; C07K 16/22; C07K 2317/524; A61K 2039/505
See application file for complete search history.

(56) References Cited

U.S. PATENT DOCUMENTS

| | | | |
|---|---|---|---|
| 4,275,149 A | 6/1981 | Litman et al. | |
| 4,318,980 A | 3/1982 | Boguslaski et al. | |
| 4,490,473 A | 12/1984 | Brunhouse | |
| 4,676,980 A | 6/1987 | Segal et al. | |
| 4,737,456 A | 4/1988 | Weng et al. | |
| 4,752,601 A | 6/1988 | Hahn | |
| 4,816,567 A | 3/1989 | Cabilly et al. | |
| 5,047,335 A | 9/1991 | Paulson et al. | |
| 5,091,178 A | 2/1992 | Hellstrom et al. | |
| 5,202,238 A | 4/1993 | Fell et al. | |
| 5,204,244 A | 4/1993 | Fell et al. | |
| 5,208,020 A | 5/1993 | Chari et al. | |
| 5,225,539 A | 7/1993 | Winter | |
| 5,278,299 A | 1/1994 | Wong et al. | |
| 5,348,876 A | 9/1994 | Michaelsen et al. |
| 5,416,064 A | 5/1995 | Chari et al. |
| 5,419,904 A | 5/1995 | Irie |
| 5,500,362 A | 3/1996 | Robinson et al. |
| 5,510,261 A | 4/1996 | Goochee et al. |
| 5,571,894 A | 11/1996 | Wels et al. |
| 5,576,184 A | 11/1996 | Better et al. |
| 5,587,458 A | 12/1996 | King et al. |
| 5,624,821 A | 4/1997 | Winter et al. |
| 5,635,483 A | 6/1997 | Pettit et al. |
| 5,648,237 A | 7/1997 | Carter |
| 5,648,260 A | 7/1997 | Winter et al. |
| 5,698,449 A | 12/1997 | Baumann et al. |
| 5,712,374 A | 1/1998 | Kuntsmann et al. |
| 5,714,586 A | 2/1998 | Kunstmann et al. |
| 5,730,977 A | 3/1998 | Ooka et al. |
| 5,731,168 A | 3/1998 | Carter et al. |
| 5,736,137 A | 4/1998 | Anderson et al. |
| 5,739,116 A | 4/1998 | Hamann et al. |
| 5,747,035 A | 5/1998 | Presta et al. |
| 5,750,373 A | 5/1998 | Garrard et al. |
| 5,767,285 A | 6/1998 | Hamann et al. |
| 5,770,429 A | 6/1998 | Lonberg et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,821,337 A | 10/1998 | Carter et al. |
| 5,834,597 A | 11/1998 | Tso et al. |

(Continued)

FOREIGN PATENT DOCUMENTS

| | | |
|---|---|---|
| CA | 2369292 A | 10/2000 |
| CA | 2645891 | 9/2007 |

(Continued)

OTHER PUBLICATIONS

Chennamsetty et al., "Aggregation-Prone Motifs in Human Immunoglobulin G" J. Mol. Biol. 391:404-413 ( 2009).
Chennamsetty et al., "Design og therapeutic proteins with enhanced stability" PNAS 106(29):11937-11942 ( 2009).
Asahara et al., "Tie2 Receptor Ligands, Angiopoietin-1 and Angiopoietin-2, Modulate VEGF-Induced Postnatal Neovascularization" Circulation Research 83:233-240 ( 1998).
Atwell et al., "Stable heterodimers from remodeling the domain interface of a homodimer using a phage display library" J. Mol. Biol. 270(1):26-35 ( 1997).

(Continued)

*Primary Examiner* — Phuong Huynh
(74) *Attorney, Agent, or Firm* — Grant E. Kalinowski

(57) ABSTRACT

The present invention relates to bispecific antibody against human vascular endothelial growth factor (VEGF/VEGF-A) and against human angiopoietin-2 (ANG-2) of human IgG1 or IgG4 subclass with mutations I253A, H310A, and H435A, methods for their production, pharmaceutical compositions containing said antibodies, and uses thereof.

11 Claims, 15 Drawing Sheets

(56) References Cited

U.S. PATENT DOCUMENTS

| | | | |
|---|---|---|---|
| 5,840,523 A | 11/1998 | Simmons et al. |
| 5,843,398 A | 12/1998 | Kaminski et al. |
| 5,859,205 A | 1/1999 | Adair et al. |
| 5,869,046 A | 2/1999 | Presta et al. |
| 5,877,296 A | 3/1999 | Hamann et al. |
| 5,885,573 A | 3/1999 | Bluestone et al. |
| 5,959,177 A | 9/1999 | Hein et al. |
| 5,985,599 A | 11/1999 | Mckenzie et al. |
| 6,030,613 A | 2/2000 | Blumberg et al. |
| 6,040,498 A | 3/2000 | Stomp et al. |
| 6,054,297 A | 4/2000 | Carter et al. |
| 6,075,181 A | 6/2000 | Kucherlaopati et al. |
| 6,086,875 A | 7/2000 | Blumberg et al. |
| 6,136,310 A | 10/2000 | Hanna et al. |
| 6,150,584 A | 11/2000 | Kucherlapati et al. |
| 6,165,464 A | 12/2000 | Hudziak et al. |
| 6,165,745 A | 12/2000 | Ward et al. |
| 6,166,185 A | 12/2000 | Davis et al. |
| 6,171,586 B1 | 1/2001 | Lam et al. |
| 6,172,213 B1 | 1/2001 | Lowman et al. |
| 6,180,377 B1 | 1/2001 | Morgan et al. |
| 6,194,551 B1 | 2/2001 | Idusogie et al. |
| 6,242,195 B1 | 6/2001 | Idusogie et al. |
| 6,248,516 B1 | 6/2001 | Winter et al. |
| 6,267,958 B1 | 7/2001 | Andya et al. |
| 6,277,375 B1 * | 8/2001 | Ward .................. 424/133.1 |
| 6,323,321 B1 | 11/2001 | Buhring |
| 6,417,429 B1 | 7/2002 | Hein et al. |
| 6,420,548 B1 | 7/2002 | Vezina et al. |
| 6,485,726 B1 | 11/2002 | Blumberg et al. |
| 6,491,916 B1 | 12/2002 | Bluestone et al. |
| 6,528,624 B1 | 3/2003 | Idusogie et al. |
| 6,538,124 B1 | 3/2003 | Idusogie et al. |
| 6,582,959 B2 | 6/2003 | Kim |
| 6,586,207 B2 | 7/2003 | Tirrell et al. |
| 6,630,579 B2 | 10/2003 | Chari et al. |
| 6,676,927 B1 | 1/2004 | Ravetch |
| 6,703,020 B1 | 3/2004 | Thorpe et al. |
| 6,706,265 B1 | 3/2004 | Bolt et al. |
| 6,737,056 B1 | 5/2004 | Presta |
| 6,815,540 B1 | 11/2004 | Pluckthun et al. |
| 6,821,505 B2 | 11/2004 | Ward |
| 6,897,044 B1 | 5/2005 | Braslawsky et al. |
| 6,946,292 B2 | 9/2005 | Kanda et al. |
| 6,982,321 B2 | 1/2006 | Winter |
| 7,041,870 B2 | 5/2006 | Tomizuka et al. |
| 7,060,269 B1 | 6/2006 | Baca et al. |
| 7,083,784 B2 | 8/2006 | Dall'Acqua et al. |
| 7,087,409 B2 | 8/2006 | Barbas et al. |
| 7,122,637 B2 | 10/2006 | Presta |
| 7,125,978 B1 | 10/2006 | Vezina et al. |
| 7,129,330 B1 | 10/2006 | Little et al. |
| 7,183,387 B1 | 2/2007 | Presta |
| 7,189,826 B2 | 3/2007 | Rodman |
| 7,214,775 B2 | 5/2007 | Hanai et al. |
| 7,276,585 B2 | 10/2007 | Lazar et al. |
| 7,297,775 B2 | 11/2007 | Idusogie et al. |
| 7,317,091 B2 | 1/2008 | Lazar et al. |
| 7,332,581 B2 | 2/2008 | Presta |
| 7,335,742 B2 | 2/2008 | Presta |
| 7,364,731 B2 | 4/2008 | Idusogie et al. |
| 7,371,826 B2 | 5/2008 | Presta |
| 7,416,727 B2 | 8/2008 | Presta |
| 7,498,298 B2 | 3/2009 | Doronina et al. |
| 7,521,541 B2 | 4/2009 | Eigenbrot et al. |
| 7,527,791 B2 | 5/2009 | Adams et al. |
| 7,563,441 B2 | 7/2009 | Graus et al. |
| 7,598,055 B2 | 10/2009 | Bobrowicz et al. |
| 7,632,497 B2 | 12/2009 | Stavenhagen |
| 7,678,373 B2 | 3/2010 | Desnoyers et al. |
| 7,691,977 B2 | 4/2010 | Fuh et al. |
| 7,741,072 B2 | 6/2010 | Idusogie et al. |
| 7,785,791 B2 | 8/2010 | Presta |
| 7,790,558 B2 | 9/2010 | Presta |
| 7,919,257 B2 | 4/2011 | Hoogenboom et al. |
| 7,923,538 B2 | 4/2011 | Shitara et al. |
| 7,931,895 B2 | 4/2011 | Beliard et al. |
| 7,960,512 B2 | 6/2011 | Stavenhagen et al. |
| 7,994,290 B2 | 8/2011 | Shitara et al. |
| 8,088,376 B2 | 1/2012 | Chamberlain et al. |
| 8,133,979 B2 | 3/2012 | Brinkmann et al. |
| 8,163,882 B2 | 4/2012 | Presta |
| 8,268,314 B2 | 9/2012 | Baehner et al. |
| 8,361,747 B2 | 1/2013 | Brinkmann et al. |
| 8,399,626 B2 | 3/2013 | Brinkmann et al. |
| 8,674,083 B2 | 3/2014 | Presta |
| 8,945,552 B2 | 2/2015 | Baehner et al. |
| 8,969,526 B2 * | 3/2015 | Baehner et al. .......... 530/387.1 |
| 2001/0036459 A1 | 11/2001 | Ravetch |
| 2002/0098193 A1 | 7/2002 | Ward |
| 2002/0197256 A1 | 12/2002 | Grewal |
| 2003/0064053 A1 | 4/2003 | Liu et al. |
| 2003/0115614 A1 | 6/2003 | Kanda et al. |
| 2003/0118592 A1 | 6/2003 | Ledbetter et al. |
| 2003/0124129 A1 | 7/2003 | Oliner et al. |
| 2003/0158389 A1 | 8/2003 | Idusogie et al. |
| 2003/0161826 A1 | 8/2003 | Arnason et al. |
| 2003/0166868 A1 | 9/2003 | Presta et al. |
| 2003/0190311 A1 | 10/2003 | Dall'Acqua et al. |
| 2003/0190317 A1 | 10/2003 | Baca et al. |
| 2003/0203409 A1 | 10/2003 | Kim |
| 2003/0206899 A1 | 11/2003 | Ferrara et al. |
| 2004/0002587 A1 | 1/2004 | Watkins et al. |
| 2004/0093621 A1 | 5/2004 | Shitara et al. |
| 2004/0110226 A1 | 6/2004 | Lazar et al. |
| 2004/0132101 A1 | 7/2004 | Lazar et al. |
| 2004/0191244 A1 | 9/2004 | Presta |
| 2004/0191256 A1 | 9/2004 | Raju |
| 2004/0191265 A1 | 9/2004 | Schenerman et al. |
| 2004/0214988 A1 | 10/2004 | Tirrell et al. |
| 2004/0228856 A1 | 11/2004 | Presta |
| 2005/0014934 A1 | 1/2005 | Hinton et al. |
| 2005/0031613 A1 | 2/2005 | Nakamura et al. |
| 2005/0031626 A1 | 2/2005 | Stevenson |
| 2005/0032114 A1 | 2/2005 | Hinton et al. |
| 2005/0037000 A1 | 2/2005 | Stavenhagen et al. |
| 2005/0054832 A1 | 3/2005 | Lazar et al. |
| 2005/0079170 A1 | 4/2005 | Le Gall et al. |
| 2005/0079574 A1 | 4/2005 | Bond |
| 2005/0079605 A1 | 4/2005 | Umana et al. |
| 2005/0112126 A1 | 5/2005 | Baca et al. |
| 2005/0118174 A1 | 6/2005 | Presta |
| 2005/0119455 A1 | 6/2005 | Fuh et al. |
| 2005/0136051 A1 | 6/2005 | Scallon |
| 2005/0142133 A1 | 6/2005 | Lazar et al. |
| 2005/0152894 A1 | 7/2005 | Krummen et al. |
| 2005/0186208 A1 | 8/2005 | Fyfe et al. |
| 2005/0227324 A1 | 10/2005 | Huang et al. |
| 2005/0233382 A1 | 10/2005 | Presta |
| 2005/0249722 A1 | 11/2005 | Beliard et al. |
| 2005/0249723 A1 | 11/2005 | Lazar |
| 2005/0260186 A1 | 11/2005 | Bookbinder et al. |
| 2005/0266000 A1 | 12/2005 | Bond |
| 2005/0272916 A1 | 12/2005 | Hanai et al. |
| 2005/0276799 A1 | 12/2005 | Hinton et al. |
| 2005/0276805 A1 | 12/2005 | Hanai et al. |
| 2006/0009360 A1 | 1/2006 | Pifer et al. |
| 2006/0018909 A1 | 1/2006 | Oliner et al. |
| 2006/0018911 A1 | 1/2006 | Ault-Riche et al. |
| 2006/0024292 A1 | 2/2006 | Gerngross et al. |
| 2006/0024298 A1 | 2/2006 | Lazar et al. |
| 2006/0024300 A1 | 2/2006 | Adams et al. |
| 2006/0024304 A1 | 2/2006 | Gerngross et al. |
| 2006/0025576 A1 | 2/2006 | Miller et al. |
| 2006/0029604 A1 | 2/2006 | Gerngross et al. |
| 2006/0034828 A1 | 2/2006 | Gerngross et al. |
| 2006/0034829 A1 | 2/2006 | Gerngross et al. |
| 2006/0034830 A1 | 2/2006 | Gerngross et al. |
| 2006/0067930 A1 | 3/2006 | Adams et al. |
| 2006/0074225 A1 | 4/2006 | Chamberlain et al. |
| 2006/0104968 A1 | 5/2006 | Bookbinder et al. |
| 2006/0121032 A1 | 6/2006 | Dahiyat et al. |
| 2006/0122370 A1 | 6/2006 | Oliner et al. |
| 2006/0134709 A1 | 6/2006 | Stavenhagen et al. |

(56) References Cited

U.S. PATENT DOCUMENTS

| | | |
|---|---|---|
| 2006/0140934 A1 | 6/2006 | Gegg et al. |
| 2006/0153838 A1 | 7/2006 | Watkins et al. |
| 2006/0160996 A9 | 7/2006 | Lazar et al. |
| 2006/0173170 A1 | 8/2006 | Chamberlain et al. |
| 2006/0194290 A1 | 8/2006 | Presta |
| 2006/0194291 A1 | 8/2006 | Presta |
| 2006/0194954 A1 | 8/2006 | Idusogie et al. |
| 2006/0194957 A1 | 8/2006 | Presta |
| 2006/0198840 A1 | 9/2006 | Dall'Acqua et al. |
| 2006/0235208 A1 | 10/2006 | Lazar et al. |
| 2006/0246004 A1 | 11/2006 | Adams et al. |
| 2006/0246071 A1 | 11/2006 | Green et al. |
| 2006/0275282 A1 | 12/2006 | Moore et al. |
| 2006/0275283 A1 | 12/2006 | Van Vlijmen et al. |
| 2006/0280747 A1 | 12/2006 | Fuh et al. |
| 2007/0003546 A1 | 1/2007 | Lazar et al. |
| 2007/0009523 A1 | 1/2007 | Presta |
| 2007/0020260 A1 | 1/2007 | Presta |
| 2007/0020267 A1 | 1/2007 | Fuh et al. |
| 2007/0036806 A1 | 2/2007 | Glaesner et al. |
| 2007/0041966 A1 | 2/2007 | Armour et al. |
| 2007/0048300 A1 | 3/2007 | Taylor et al. |
| 2007/0053901 A1 | 3/2007 | Lazar et al. |
| 2007/0061900 A1 | 3/2007 | Murphy et al. |
| 2007/0117126 A1 | 5/2007 | Sidhu et al. |
| 2007/0122403 A1 | 5/2007 | Dall'Acqua et al. |
| 2007/0122406 A1 | 5/2007 | Chamberlain et al. |
| 2007/0135620 A1 | 6/2007 | Chamberlain et al. |
| 2007/0141065 A1 | 6/2007 | Fuh et al. |
| 2007/0148171 A1 | 6/2007 | Lazar et al. |
| 2007/0160597 A1 | 7/2007 | Lazar et al. |
| 2007/0160598 A1 | 7/2007 | Dennis et al. |
| 2007/0161783 A1 | 7/2007 | Barbosa et al. |
| 2007/0166309 A1 | 7/2007 | Lazar et al. |
| 2007/0202098 A1 | 8/2007 | Lazar et al. |
| 2007/0219133 A1 | 9/2007 | Lazar et al. |
| 2007/0224189 A1 | 9/2007 | Lazar et al. |
| 2007/0224192 A1 | 9/2007 | Lazar et al. |
| 2007/0231329 A1 | 10/2007 | Lazar et al. |
| 2007/0237764 A1 | 10/2007 | Birtalan et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0238665 A1 | 10/2007 | Lazar et al. |
| 2007/0243188 A1 | 10/2007 | Lazar et al. |
| 2007/0248602 A1 | 10/2007 | Lazar et al. |
| 2007/0248603 A1 | 10/2007 | Lazar et al. |
| 2007/0286859 A1 | 12/2007 | Lazar et al. |
| 2007/0292936 A1 | 12/2007 | Barthelemy et al. |
| 2008/0051563 A1 | 2/2008 | Lazar et al. |
| 2008/0057056 A1 | 3/2008 | Lazar et al. |
| 2008/0069820 A1 | 3/2008 | Fuh et al. |
| 2008/0095762 A1 | 4/2008 | Presta |
| 2008/0138338 A1 | 6/2008 | Idusogie et al. |
| 2008/0152649 A1 | 6/2008 | Chamberlain et al. |
| 2008/0154025 A1 | 6/2008 | Lazar et al. |
| 2008/0161541 A1 | 7/2008 | Lazar et al. |
| 2008/0181890 A1 | 7/2008 | Lazar et al. |
| 2008/0206242 A1 | 8/2008 | Lawrence et al. |
| 2008/0274105 A1 | 11/2008 | Presta |
| 2008/0274108 A1 | 11/2008 | Presta |
| 2009/0041770 A1 | 2/2009 | Chamberlain et al. |
| 2009/0060911 A1 | 3/2009 | Ravetch |
| 2009/0068182 A1 | 3/2009 | Young et al. |
| 2009/0148441 A1 | 6/2009 | Gillies |
| 2009/0162359 A1 | 6/2009 | Klein et al. |
| 2009/0162360 A1 | 6/2009 | Klein et al. |
| 2009/0163699 A1 | 6/2009 | Chamberlain et al. |
| 2009/0175851 A1 | 7/2009 | Klein |
| 2009/0232811 A1 | 9/2009 | Klein et al. |
| 2010/0098730 A1 | 4/2010 | Lowman et al. |
| 2010/0111967 A1* | 5/2010 | Baehner et al. .......... 424/158.1 |
| 2010/0166740 A1 | 7/2010 | Endl et al. |
| 2010/0166749 A1 | 7/2010 | Presta |
| 2010/0255013 A1 | 10/2010 | Presta |
| 2011/0052584 A1 | 3/2011 | Ravetch |
| 2011/0086050 A1 | 4/2011 | Presta |
| 2011/0293632 A1 | 12/2011 | Presta |
| 2012/0201813 A1 | 8/2012 | Presta |
| 2012/0321627 A1 | 12/2012 | Baehner et al. |
| 2013/0156789 A1 | 6/2013 | Brinkmann et al. |
| 2014/0065151 A1 | 3/2014 | Brinkmann et al. |
| 2014/0065707 A1 | 3/2014 | Brinkmann et al. |
| 2015/0004166 A1 | 1/2015 | Baehner et al. |

FOREIGN PATENT DOCUMENTS

| | | |
|---|---|---|
| CA | 2 700 986 | 4/2009 |
| CL | 147-2007 | 1/2007 |
| CN | 101098890 | 1/2008 |
| CN | 102250247 | 11/2011 |
| CN | 102250248 | 11/2011 |
| EC | SP992970 | 1/2000 |
| EP | 0 404 097 B1 | 6/1990 |
| EP | 0 425 235 B1 | 9/1996 |
| EP | 0 359 096 | 11/1997 |
| EP | 0 811 691 B1 | 12/1997 |
| EP | 1176195 A1 | 1/2002 |
| EP | 0 666 868 B1 | 4/2002 |
| EP | 1 270 595 B1 | 1/2003 |
| EP | 1331266 A1 | 7/2003 |
| EP | 1331266 A4 | 7/2003 |
| EP | 0 904 107 | 10/2004 |
| EP | 1 498 491 A1 | 1/2005 |
| EP | 1 498 491 A4 | 1/2005 |
| EP | 1870459 | 3/2006 |
| EP | 1 068 241 B1 | 10/2007 |
| EP | 1 870 459 A1 | 12/2007 |
| EP | 1 692 182 B1 | 4/2010 |
| EP | 2 248 829 | 11/2010 |
| EP | 2252632 | 1/2014 |
| JP | 2006255668 | 9/2006 |
| RU | 2005136988 | 6/2006 |
| WO | 88/07089 A1 | 9/1988 |
| WO | 92/16562 | 10/1992 |
| WO | 93/01161 A1 | 1/1993 |
| WO | 93/06217 | 4/1993 |
| WO | 93/08829 A1 | 5/1993 |
| WO | 93/16185 A2 | 8/1993 |
| WO | 93/16185 A3 | 8/1993 |
| WO | 93/22332 A2 | 11/1993 |
| WO | 93/22332 A3 | 11/1993 |
| WO | 94/08027 A1 | 4/1994 |
| WO | 93/10202 | 5/1994 |
| WO | 94/11026 A2 | 5/1994 |
| WO | 94/11026 A3 | 5/1994 |
| WO | 97/10202 | 5/1994 |
| WO | 94/29350 | 12/1994 |
| WO | 94/29351 A2 | 12/1994 |
| WO | 95/09917 A1 | 4/1995 |
| WO | 96/27011 | 9/1996 |
| WO | 96/27011 A1 | 9/1996 |
| WO | 96/30046 | 10/1996 |
| WO | 96/32478 A1 | 10/1996 |
| WO | 97/01580 A1 | 1/1997 |
| WO | 97/28267 A1 | 8/1997 |
| WO | 97/30087 A1 | 8/1997 |
| WO | 97/34631 A1 | 9/1997 |
| WO | 97/43316 A1 | 11/1997 |
| WO | 97/44362 A1 | 11/1997 |
| WO | 98/23289 A1 | 6/1998 |
| WO | 98/33924 A1 | 8/1998 |
| WO | 98/45331 A2 | 10/1998 |
| WO | 98/45331 A3 | 10/1998 |
| WO | 98/45332 | 10/1998 |
| WO | 98/45332 A2 | 10/1998 |
| WO | 98/48032 A2 | 10/1998 |
| WO | 98/48032 A3 | 10/1998 |
| WO | 98/52975 A1 | 11/1998 |
| WO | 98/58964 A1 | 12/1998 |
| WO | 99/22764 A1 | 5/1999 |
| WO | 99/43713 A1 | 9/1999 |
| WO | 99/51642 A1 | 10/1999 |
| WO | 99/54342 A1 | 10/1999 |

(56) References Cited

FOREIGN PATENT DOCUMENTS

| | | |
|---|---|---|
| WO | 99/58572 A1 | 11/1999 |
| WO | 00/09560 A2 | 2/2000 |
| WO | 00/09560 A3 | 2/2000 |
| WO | 00/35956 A1 | 6/2000 |
| WO | 00/42072 A2 | 7/2000 |
| WO | 00/42072 A3 | 7/2000 |
| WO | 00/61739 A1 | 10/2000 |
| WO | 00/75348 | 12/2000 |
| WO | 01/40309 A2 | 6/2001 |
| WO | 01/64754 A1 | 7/2001 |
| WO | 01/58957 A2 | 8/2001 |
| WO | 01/58957 A3 | 8/2001 |
| WO | 01/77181 | 10/2001 |
| WO | 01/77342 A | 10/2001 |
| WO | 02/31140 A1 | 4/2002 |
| WO | 02/060919 A2 | 8/2002 |
| WO | 02/083854 A2 | 10/2002 |
| WO | 03/011878 A2 | 2/2003 |
| WO | 03/020906 A2 | 3/2003 |
| WO | 03/030833 A2 | 4/2003 |
| WO | 03/035835 A2 | 5/2003 |
| WO | 03/055993 A1 | 7/2003 |
| WO | 03/057134 A2 | 7/2003 |
| WO | 03/073238 A2 | 9/2003 |
| WO | 03/073238 A3 | 9/2003 |
| WO | 03/074679 | 9/2003 |
| WO | 03/106501 A1 | 12/2003 |
| WO | 2004/004662 A2 | 1/2004 |
| WO | 2004/004662 A3 | 1/2004 |
| WO | 2004/004798 A2 | 1/2004 |
| WO | 2004/011611 A2 | 2/2004 |
| WO | 2004/029207 A2 | 4/2004 |
| WO | 2004/029207 A3 | 4/2004 |
| WO | 2004/035752 A2 | 4/2004 |
| WO | 2004/035752 A3 | 4/2004 |
| WO | 2004/063351 A2 | 7/2004 |
| WO | 2004/092219 A2 | 10/2004 |
| WO | 2004/092219 A3 | 10/2004 |
| WO | 2004/099249 A2 | 11/2004 |
| WO | 2005/000900 A1 | 1/2005 |
| WO | 2005/012359 A2 | 2/2005 |
| WO | 2005/018572 A2 | 3/2005 |
| WO | 2005/018572 A3 | 3/2005 |
| WO | 2005/035727 A2 | 4/2005 |
| WO | 2005/035727 A3 | 4/2005 |
| WO | 2005/037867 A1 | 4/2005 |
| WO | 2005/040217 A2 | 5/2005 |
| WO | 2005/040217 A8 | 5/2005 |
| WO | 2005/044853 A2 | 5/2005 |
| WO | 2005/047327 A2 | 5/2005 |
| WO | 2005/047327 A8 | 5/2005 |
| WO | 2005/054273 | 6/2005 |
| WO | 2005/074524 A3 | 8/2005 |
| WO | 2005/100402 A1 | 10/2005 |
| WO | 2005/123780 A2 | 12/2005 |
| WO | 2005/123780 A3 | 12/2005 |
| WO | 2006/002058 A2 | 1/2006 |
| WO | 2006/020114 A2 | 2/2006 |
| WO | 2006/020114 A3 | 2/2006 |
| WO | 2006/029879 A2 | 3/2006 |
| WO | 2006/031370 A2 | 3/2006 |
| WO | 2006/044908 A2 | 4/2006 |
| WO | 2006/045049 | 4/2006 |
| WO | 2006/047350 A3 | 5/2006 |
| WO | 2006/053301 A2 | 5/2006 |
| WO | 2006/053301 A3 | 5/2006 |
| WO | 2006/053301 A9 | 5/2006 |
| WO | 2006/0473350 | 5/2006 |
| WO | 2006/068953 A2 | 6/2006 |
| WO | 2006/076594 A2 | 7/2006 |
| WO | 2006/076594 A3 | 7/2006 |
| WO | 2006/093794 A1 | 9/2006 |
| WO | 2006/116260 A2 | 11/2006 |
| WO | 2007/024715 A2 | 3/2007 |
| WO | 2007/024715 A3 | 3/2007 |
| WO | 2007/024715 A9 | 3/2007 |
| WO | 2007/033216 | 3/2007 |
| WO | 2007/044887 A2 | 4/2007 |
| WO | 2007/068895 | 6/2007 |
| WO | 2007/089445 | 8/2007 |
| WO | 2007/109254 A2 | 9/2007 |
| WO | 2005/074524 A2 | 5/2007 |
| WO | 2008/073300 | 6/2008 |
| WO | 2008/077077 A2 | 6/2008 |
| WO | 2008/132568 | 11/2008 |
| WO | 2008/149147 | 12/2008 |
| WO | 2008/149149 | 12/2008 |
| WO | 2009/006520 A1 | 1/2009 |
| WO | 2009/032782 A2 | 3/2009 |
| WO | 2009/058492 A2 | 5/2009 |
| WO | 2009/058492 A3 | 5/2009 |
| WO | 2009/058812 A1 | 5/2009 |
| WO | 2009/068649 | 6/2009 |
| WO | 2009/073160 A1 | 6/2009 |
| WO | 2009/080251 A1 | 7/2009 |
| WO | 2009/080252 A2 | 7/2009 |
| WO | 2009/080253 A1 | 7/2009 |
| WO | 2009/080254 A1 | 7/2009 |
| WO | 2009/086320 A1 | 7/2009 |
| WO | 2009/089004 A1 | 7/2009 |
| WO | 2009/100309 A2 | 8/2009 |
| WO | 2009/100309 A3 | 8/2009 |
| WO | 2009/105269 | 8/2009 |
| WO | 2009/134776 A2 | 11/2009 |
| WO | 2009/136352 | 11/2009 |
| WO | 2009/142460 A2 | 11/2009 |
| WO | 2009/155513 | 12/2009 |
| WO | 2009/155724 | 12/2009 |
| WO | 2010/027981 | 3/2010 |
| WO | 2010/040508 A1 | 4/2010 |
| WO | 2010/045193 A1 | 4/2010 |
| WO | 99/37791 | 2/2011 |
| WO | 2011/014469 | 2/2011 |
| WO | 2011/117329 | 9/2011 |
| WO | 2011/117330 | 9/2011 |
| WO | 2011/139718 | 11/2011 |
| WO | 2012/131078 | 10/2012 |
| WO | 2010/069532 A1 | 6/2013 |

OTHER PUBLICATIONS

Barnes et al., "Advances in animal cell recombinant Protein production: GS-NS0 expression system" Cytotechnology 32(2):109-23 (Feb. 2000).

Barnes et al., "Characterization of the stability of recombinant protein production in the GS-NS0 expression system" Biotechnol Bioeng 73(4):261-70 (May 2001).

Berkman, R. A. et al., "Expression of the vascular permeability factor/vascular endothelial growth factor gene in central nervous system neoplasms" J Clin Invest 91:153-159 (Jan. 1993).

Boerner et al., "Production of antigen-specific human monoclonal antibodies from in vitro-primes human splenocytes" J Immunol 147(1):86-95 (Jul. 1, 1991).

Brown, L. F. et al., "Expression of vascular permeability factor (vascular endothelial growth factor) and its receptors in breast cancer" Hum Pathol 26(1):86-91 ( 1995).

Brown, L. F. et al., "Expression of vascular permeability factor (Vascular endothelial growth factor) and its receptors in adenocarcinomas of the gastrointestinal tract" Cancer Res 53:4727-4735 (Oct. 1, 1993).

Bruggemann et al., "Designer mice: the production of human antibody repertoires in transgenic animals" Year in Immunology 7:33-40 ( 1993).

Carter et al., "Humanization of an anti-p185 $^{HER2}$ antibody for human cancer therapy" P Natl Acad Sci USA 89:4285-4289 (May 1992).

Cheung et al., "Endothelial Tie2/Tek Ligands Angiopoietin-1 (ANGPT1) and Angiopoietin-2 (ANGPT2): Regional Localization of the Human Genes to 8q22.3-q23 and 8p23" Genomics 48:389-391 ( 1998).

Cohen et al., "Nonchromosomal Antibiotic Resistance in Bacteria: Genetic Transformation of *Escherichia coli* by R-Factor DNA" Proc. Natl. Acad. Sci. USA 69(8):2110-2114 (Aug. 1972).

(56) References Cited

OTHER PUBLICATIONS

Connolly et al., "Human vascular permeability factor. Isolation from U937 cells" J Biol Chem. 264(33):20017-24 ( 1989).
Davis et al. et al., "Isolation of angiopoietin-1, a ligand for the TIE2 receptor, by secretion-trap expression cloning" Cell 87(7):1161-1169 (Dec. 27, 1996).
Deissler et al., "Actions of Bevacizumab and Ranibizumab on Microvascular Retinal Endothelil Cells: Similarities and Differences" Br. J. Ophthalmol. 96:1023-1028 (2012).
Durocher et al. et al., "High-level and high-throughput recombinant protein production by transient transfection of suspension-growing human 293-EBNA1 cells" Nucleic Acids Res 30(2):E9 ( 2002).
Dvorak et al., "Vascular permeability factor/vascular endothelial growth factor, microvascular hyperpermeability, and angiogenesis" Am J Pathol 146(5):1029-1039(May 1995).
Edelman et al., "The covalent structure of an entire γG immunoglobulin molecule" P Natl Acad Sci USA 63:78-85 ( 1969).
Ferrara and Davis-Smyth, "The Biology of Vascular Endothelial Growth Factor" Endocr Rev 18(1):4-25 ( 1997).
Folkman and Shing, "Angiogenesis" J Biol Chem 267(16):10931-10934 (Jun. 5, 1992).
Geisse et al., "Eukaryotic Expression Systems: A Comparison" Protein Expres Purif 8:271-282 ( 1996).
Graham and Van Der Eb et al., "A New Technique for the Assay of Infectivity of Human Adenovirus 5 DNA" Virology 52:456-467 ( 1973).
He et al., "High-throughput dynamic light scattering methods for measuring visosity of concentrated protein solutions" Analytical Biochemistry 399:141-143 (2010).
Hoogenboom and Winter, "By-passing immunisation human antibodies from synthetic repertoires of germline $V_H$ gene segments rearranged in vitro" J. Mol. Biol. 227:381-388 ( 1992).
Jakobovits et al., "Analysis of Homozygous Mutant Chimeric Mice:Deletion of the Immunoglobulin Heavy-chain Joining Region Blocks B-cell Development and Antibody Production" P Natl Acad Sci USA 90:2551-2555 (Mar. 1993).
Jakobovits et al., "Germ-line Transmission and Expression of a Human-Derived Yeast Artificial Chromosome" Nature 362(6417):255-258 (Mar. 18, 1993).
Johnson et al. et al., "Kabat Database and its applications: 30 years after the first variability plot" Nucleic Acids Res 28(1):214-218 ( 2000).
Kabat et al. Sequences of Proteins of Immunological Interest Fifth edition,NIH Publication,:91-3242 ( 1991).
Kabat et al., "Evolutionary and structural influences on light chain constant (C/subL/nor) region of human of human and mouse immunoglobulins" Proc Natl Acad Sci U S A. 72(7):2785-8 (Jul. 1975).
Kaufman, "Overview of Vector Design for Mammalian Gene Expression" Mol Biotechnol 16:151-160 ( 2000).
Keck et al., "Vascular Permeability Factor, an Endothelial Cell Mitogen Related to PDGF" Science 246:1309-1312 ( 1989).
Kim et al., "Angiopoietin-2 at high concentration can enhance endothelial cell survival through the phosphatidylinositol 3'-kinase/Akt signal transduction pathway" Oncogene 19:4549-4552 ( 2000).
Kim et al., "FcRn receptor-mediated pharmacokinetics of therapeutic IgG in the eye" Molecular Vision 5:2803-2812 ( 2009).
Kim et al., "Mapping the site on human IgG for binding of the MHC class I-related receptor, FcRn" Eur J Immunol 29(9):2819-2825 (Sep. 1999).
Kim et al., "Molecular cloning and characterization of a novel angiopoietin family protein, angiopoietin-3" FEBS LETT 443(3):353-356 ( 1999).
Kim et al., "Molecular cloning, expression and characterization of angiopoietin-related protein" The Journal of Biological Chemistry 274(37):26523-26528 ( 1999).
Klagsbrun and D'Amore, "Regulators of angiogenesis" Ann Rev Physiol 53:217-239 ( 1991).

Kobayashi et al., "Similarities in the biodistribution of iodine-labeled anti-tac single-chain disulfide-stabilized Fv fragment and anti-tac disulfide-stabilized Fv fragment" Nuclear Med. & Biol. 25:387-393 ( 1998).
Kuo et al., "Neonatal Fc receptor: from immunity to therapeutics" J. Clin. Immunol. 30:777-789 ( 2010).
Leung et al., "Vascular Endothelial Growth Factor is a Secreted Angiogenic Mitogen" Science 246:1306-1309 (Dec. 1989).
Maisonpierre et al. et al., "Angiopoietin-2, a Natural Antagonist for Tie2 that Disrupts in vivo Angiogenesis" Science 277:55-60 (Jul. 4, 1997).
Makrides, S., et al., "Components of Vctors for Gene Transfer and Expression in mammalian cells" Protein Expression and Purification 17:183-202 ( 1999).
Marks et al., "By-passing immunization, Human antibodies from V-gene libraries from V-gene libraries displayed on phage" J. Mol. Biol. 222:581-597 ( 1991).
Mattern, J. et al., "Association of vascular endothelial growth factor expression with intratumoral microvessel density and tumour cell proliferation in human epidermoid lung carcinoma" Brit J Cancer 73:931-934 ( 1996).
Merchant et al., "An Efficient Route to Human Bispecific IgG" Nat Biotechnol. 16:677-681 (Jul. 1998).
Meyer et al., "Bevacizumab immune complexes activate platelets and induce thrombosis in FCGR2A transgenic mice" J. of Thrombosis and Haemostasis 7:171-181 ( 2008).
Neuberger et al., "A hapten-specific chimaeric IgE antibody with human physiological effector function" Nature 314:268-270 (Mar. 21, 1985).
Norderhaug et al. et al., "Versatile Vectors for Transient and Stable Expression of Recombinant Antibody Molecules in Mammalian Cells" J Immunol Methods 204:77-87 ( 1997).
Orlandi et al. et al., "Cloning Immunoglobulin Variable Domains for Expression by the Polymerase Chain Reaction" P Natl Acad Sci USA 86:3833-3837 (May 1989).
Qiao et al., "Dependence of antibody-mediated presentation of antigen on FcRn" PNAS 105(27):9337-9342 ( 2008).
Rajagopal et al., "A Form of Anti-Tac(Fv) Which is Both Single-chain and Disulfide Stabilized: Comparison with its Single-chain and Disulfide-stabilized Homologs" Protein Eng 10(12):1453-1459 ( 1997).
Ridgway et al., "'Knobs-into-holes' Engineering of Antibody $C_H3$ Domains for Heavy Chain Heterodimerization" Protein Eng 9(7):617-621 ( 1996).
Riechmann et al., "Reshaping human antibodies for therapy" Nature 332:323-327 (Mar. 1988).
Ritter et al., "Myeloid progenitors differentiate into microglia and promote vascualr repair in a model of ischemic retinopathy" J. of Clinical Investigation 116(12):3266-3276 ( 2006).
Rogers et al., "The mouse cornea micropocket angiogenesis assay" Nature Protocols 2(10):2545-2550 ( 2007).
Russelakis-Carneiro et al., "Inflammatory response and retinal ganglion cell degeneration following intraocular injection of ME7" Neuropathology and Applied Neurobiology 25:196-206 ( 1999).
Schlaeger et al. et al., "Transient Gene Expression in Mammalian Cells Grown in Serum-free Suspension Culture" Cytotechnology 30:71-83 ( 1999).
Schlaeger, E. et al., "The protein hydrolysate, primatone RL, is a cost-effective multiple growth promoter of mammalian cel culture in serum-containing and serum-free medi and displays anti-apoptosis properties" J. of Immunological Methods 194:191-199 ( 1996).
Schmidt et al., "Suppression of Metastasis Fomation by a Recombinant Single Chain Antibody-Toxin Targeted to Full-length and Oncogenic Variant EGF Receptors" Oncogene 18:1711-1721 ( 1999).
Sinapis et al., "pharmacokinetics of intravitreal bevacizumab (Avastin®) in rabbits" Clinical Ophthalmology 5:697-704 ( 2011).
van Dijk and van de Winkel, "Human antibodies as next generation therapeutics" Curr Opin Chem Biol 5(4):368-74 (Aug. 2001).
Vijayalakshmi, "Antibody purification methods" Appl Biochem Biotech 75:93-102 ( 1998).

(56) References Cited

OTHER PUBLICATIONS

Werner et al., "Appropriate mammalian expression systems for biopharmaceuticals" Arznei-Forschung/Drug Res 48(8):870-880 ( 1998).
Wray et al., "Experimental allergic encephalomyelitis" Arch. Neurol. 33:183-185 ( 1976).
Yancopoulos et al., "Vascular-specific growth factors and blood vessel formation" Nature 407:242-248 ( 2000).
Monkos et al., "Concentration and temperature dependence of viscosity in lysozyme aqueous solutions" Biochimica et Biophysica Acta 1339:304-310 ( 1997).
Mooney et al., "The viscosity of a concentrated suspension of spherical particles" J. of Colloid Science 6(2):162-170 ( 1951).
White et al., "Antibody-targeted immunotherapy for treatment of malignancy" Ann Rev Med 52:125-145 ( 2001).
Zhang et al., Chemistry of Life 27:166-169 ( 2007).
Zhang et al., "English translation of the Abstract" Chemistry of Life 27:166-169 ( 2007).
(The Merck Index, An encyclopedia of Chemicals, Drugs, and Biologicals), Maryadale J. O'Neil, 14th Edition, Whitehouse Station, NJ USA:Merck Research Laboratories, Division of Merck & Co, Inc.,:26-27 ( 2006).
(Translation of Korean Office Action in Corres Korean App 2011 7008184 Oct. 10, 2012).
(Translation of Taiwanese Off Act in Corres Taiwan App 098142952 Jul. 2, 2012).
Atwell et al., "Stable Heterodimers from Remodeling the Domain Interface of a Homodimer using a Phage Display Library" Journal of Mol. Biol. 270:26-35 ( 1997).
Beckman et al., "Antibody Constructs in Cancer Therapy" Cancer 109(2):170-179 (Jan. 15, 2007).
Borgstrom et al., "Complete Inhibition of Angiogenesis and Growth of Microtumors by Anti-Vascular Endothelial Growth Factor Neutralizing Antibody: Novel Concerts of Angiostatic Therapy from Intravital Videomicrocopy" Cancer Research 56:4032-4039 ( 1996).
Brown et al., "A Human Monoclonal Anti-ANG2 Antibody Leads to Broad Antitumor Activity in Combination with VEGF Inhibitors and Chemotherapy Agents in Preclinical Models" Molecular Cancer Therapeutics 9(1):145-156 (Jan. 2010).
Carter, "Bispecific human IgG by design" J Immunol Methods 248(1-2):7-15 (Feb. 1, 2001).
Casset et al., Biochem. Biophys. Res. Commun. 307(1):198-205 ( 2003).
Cespedes, Maria V., "Mouse Models in Oncogenesis and Cancer Therapy" Clin. Transl. Oncol. 8(5):318-29 (2006).
Chan et al., "Therapeutic antibodies for autoimmunity and inflammation" Nature Reviews Immunology 10:301-316 (May 2010).
Chan et al., "Variable Region Domain Exchange in Human IgGs Promotes Antibody Complex Formation with Accompanying Structural Changes and Altered Affector Functions" Molecular Immunology 41:527-538 ( 2004).
Coloma et al., "Design and Production of Novel Tetravalent Bispecific Antibodies" Nature Biotechnology 15:159-163 ( 1997).
Coxon et al., "Combined Treatment of Angiopoietin and VEGF Pathway Antagonists Enhances Antitumor Activity in Preclinical Models of Colon Carcinoma" Proceedings of the American Association for Cancer Research Annual Meeting:262-263 ( 2008).
Dennis, Carina, "Off by a Whisker" Nature 442:739-741 (2006).
Fischer and Leger, "Bispecific antibodies: Molecules that enable novel therapeutic strategies" Pathobiology 74:3-14 ( 2007).
Fujimori et al., "A Modeling Analysis of Monoclonal Antibody Percolation Through Tumors: A Binding Site Barrier" J. Nuc. Med. 31:1191-1198 ( 1990).
Hammes et al., "Angiopoietin-2 causes pericyte dropout in the normal retina—Evidence for involvement in diabetic retinopathy" Diabetes 53:1104-1110 (Apr. 2004).
Holliger et al., "Engineered antibody fragments and the rise of single domains" Nat Biotechnol 23(9):1126-36 (Sep. 2005).

Jaumdally et al., "Systemic and intracardiac vascular endothelial growth factor and angiopoietin-1 and -2 levels in coronary artery disease: Effects of angioplasty" Annals of Medicine 39:298-305 ( 2007).
Jendreyko et al., "Phenotypic Knockout of VEGF-R2 and Tie-2 with an Intradiabody Reduces Tumor Growth and Angiogenesis in Vivo" PNAS 102(23):8293-8298 ( 2005).
Jendreyko et al., "Simultaneous, Phenotypic Knockout of VEGF-R2 and Tie-2 with an Intradiabody Enhances Antiangiogenic Effects in Vivo" Klinische Padiatrie 218:143-151 ( 2006).
Kienast et al., "Ang-2-VEGF-A CrossMab, a Novel Bispecific Human IgG1 Antibody Blocking VEGF-A and Ang-2 Functions Simultaneously, Mediates Potent Antitumor, Antiangiogenic, and Antimetastatic Efficacy" Clin Cancer Res 19(242):6730-6740 (Dec. 15, 2013).
Kim et al., "Inhibition of vascualr endothelial growth factor-induced angiogenesis suppresses tumour growth in vivo" Nature 362:841-844 (Apr. 1993).
Klimka et al., British Journal of Cancer, 83:252-260 ( 2000).
Liang et al., "Cross-Species Vascular Endothelial Growth Factor (VEGF)-Blocking Antibodies Completely Inhibit the Growth of Human Tumor Xenografts and Measure the Contribution of Stromal VEGF" Journal of Biological Chemistry 28(2):951-961 ( 2006).
Lu et al., "A fully human recombinant IgG-like bispecific antibody to both the epidermal growth factor receptor and the insulin-like growth factor receptor for enhanced antitumor activity" J. Biol. Chem. 280(20):19665-72 ( 2005).
Lu et al., "Simultaneous blockade of both the epidermal growth factor receptor and the insulin-like growth factor receptor signaling pathways in cancer cells with a fully human recombinant bispecific antibody" J. Biol. Chem. 279(4):2856-65 ( 2004).
Mabry et al., "Engineering of stable bispecific antibodies targeting IL-17A and IL-23" Protein Engineering, Design & Selection 23(3):115-127 ( 2010).
MacCallum et al., J. Mol. Biol. 262(5):732-745 (Oct. 1996).
Melnyk et al., "Vascular Endothelial Growth Factor Promotes Tumor Dissemination by a Mechanism Distinct from its Effect on Primary Tumor Growth" Cancer Research 56:921-924 ( 1996).
Miller et al., "Design, Construction, and in Vitro Analyses of Multivalent Antibodies" Journal of Immunology 170:4854-4861 ( 2003).
Morrison et al., "Chimeric human antibody molecules: Mouse antigen-binding domains with human constant region domains" P Natl Acad Sci USA 81:6851-6855 (Nov. 1984).
Morrison et al., "Variable Region Domain Exchange Influences the Functional Properties of IgG" Journal of Immunology 160:2802-2808 ( 1998).
Morrison, S., "Two Heads are Better Than One—A new Design for Bispecific Antibodies Enables Efficient Production of Stable Molecules with Good Pharmacodynamic Properties." Nat Biotechnol 25(11):1233-1234 ( 2007).
Niu, G. et al., "Human epidermal growth factor receptor 2 regulates angiopoietin-2 expression in breast cancer via AKT and mitogen-activated protein kinase pathways" Cancer Research 67:1487-1493 ( 2007).
Notice of Opposition for Ecuadorian Application No. SP-2013-DIV-11-11139-D1 with English translation. (Mar. 6, 2015).
Oliner et al., "Suppression of Angiogenesis and Tumor Growth by Selective Inhibition of Angiopoietin-2" Cancer Cell 6(5):507-516 ( 2004).
Padlan, Mol. Immunol. 31(3):169-217 (Feb. 1994).
Paul, Fundamental Immunology,(3rd Edition):292-295 ( 1993).
Presta et al., "Humanization of an Anti-Vascular Endothelial Growth Factor Monoclonal Antibody for the Therapy of Solid Tumors and Other Disorders" Cancer Res 57(20):4593-4599 (Oct. 15, 1997).
Ridgway et al., "Knobs-into-holes' engineering of antibody CH3 domains for heavy chain heterodimerization" Protein Engineering 9(7):617-621 ( 1996).
Rossi, E.A. et al., "Multivalent Anti-CD20/Anti-CD22 Bispecific Antibody Fusion Proteins Made by the DNL Method Show Potent Lymphoma Cytotoxicity" Abstract ASH Annual Meeting, pp. Abstract 2495 (2006).

(56) References Cited

OTHER PUBLICATIONS

Rudikoff et al., "Single amino acid substitution altering antigen-binding specificity" Proc. Natl. Acad. Sci. USA, 79(6):1979-1983 (Mar. 1982).
Rudnick et al., "Affinity and Avidity in Antibody-Based Tumor Targeting" Cancer Biotherapy and Radiopharmaceuticals 24:155-162 ( 2009).
Schaefer et al., "Immunoglobulin domain crossover as a generic approach for the production of bispecific IgG antibodies" Proceedings of the National Academy of Sciences 108(27):11187-11192 (Jul. 5, 2011).
Schoonjans et al., "Fab Chains as an Efficient Heterodimerization Scaffold for the Production of Recombinant Bispecific and Trispecific Antibody Derivatives" Journal of Immunology 165:7050-7057 ( 2000).
Shen et al., "Single Variable Domain Antibody as a Versatile Building Block for the Construction of IgG-like Bispecific Antiobodies" Journal of Immunological methods 318:65-74 ( 2007).
Simon et al., "Antibody Domain Mutants Demonstrate Autonomy of the Antigen Binding Site" EMBO Journal 9(4):1051-1056 ( 1990).
Talmadge, James E., et al., "Murine Models to Evaluate Novel and Conventional Therapeutic Strategies for Cancer" Am. J. Pathol. 170(3):793-804 (2007).
Thomas et al., EJC Supplements, 8(7):156-157 (Nov. 2010).
Thomas, M. et al., "A novel angiopoietin-2 selective fully human antibody with potent anti-tumoral and anti-angiogenic efficacy and superior side effect profile compares to pan-angiopoietin-1-2 inhibitors" PLOS One 8(2):1-11 ( 2013).
Thurber et al., "Antibody tumor penetration: transport opposed by systemic and antigen-mediated clearance" Advanced Drug Delivery Reviews 60:1421-1437 ( 2008).
Voskoglou-Nomikos, Theodora, et al., "Clinical Predictive Value of the in Vitro Cell Line, Human Xenograft, and Mouse Allograft Preclinical Cancer Models" Clin. Can. Res. 9:4227-4239 (Sep. 15, 2003).
Warren et al., "Regulation by Vascular Endothelial Growth Factor of Human Colon Cancer Tumorigenesis in a Mouse Model of Experimental Liver Metastasis" Journal of Clinical Investigation 95:1789-1797 ( 1995).
Wu et al., "Simultaneous Targeting of Multiple Disease Mediators by a Dual-Variable-Domain Immunoglobulin" Nature Biotech. 25:1290-1297 ( 2007).
Xie et al., "A new Format of bispecific antibody: highly efficient heterodimerization, expression and tumor cell lysis" Journal of Immunological Methods 296:95-101 ( 2005).
"International Search Report and Written Opinion for PCT/US2009/060443".
(Int'l Search Report for PCT Application No. PCT/US02/33739, Filed on Oct. 22, 2002, two pages Jun. 16, 2003).
(Kabat et al., NIH Publication 91 (1991) 3242, National Technical Information Service, Springfield, VA),.
pp. 1-6 (Original claims of the U.S. Pat. No. 6,737,056 restricted Jan. 14, 2000).
pp. 1-8 (Restriction Requirement for the U.S. Pat. No. 6,737,056 Sep. 25, 2001).
Abes et al., "Activating and inhibitory Fcγ receptors in immunotherapy: being the actor or being the target" Expert Rev Clin Immunol 5(6):735-747 (2009).
Adamis, A. P. et al., "Inhibition of Vascular Endothelial Growth Factor Prevents Retinal Ischemia-Associated Iris Neovascularization in a Nonhuman Primate" Arch Ophthalmol-Chic 114(1):66-71 (1996).
Allan and Isliker, "Studies on the complement-binding site of rabbit immunoglobulin G-I Modification of tryptophan residues and their role in anticomplementary activity of rabbit IgG" Immunochemistry 11(4):175-180 (Apr. 1974).
Almagro et al., "Humanization of antibodies" Frontiers in Bioscience 13:1619-1633 (Jan. 2008).

Anderson et al., "Targeted anti-cancer therapy using rituximab, a chimaeric anti-CD20 antibody (IDEC-C2B8) in the treatment of non-Hodgkin's B-cell lymphoma" Biochemical Soc. Transactions 25:75 (1997).
Angal et al. "A single amino acid substituion abolishes the heterogeneity of chimeric mouse/human (IgG4) antibody" Mol Immunol 30(1):105-108 (Jan. 1993).
Angata et al., "Differential and Cooperative Polysialylation of the Neutral Cell Adhesion Molecule by Two Polysialyltransferases, PST and STX" The Journal of Biological Chemistry 273(43):28524-28532 (Oct. 23, 1998).
Armour et al., "Recombinant Human IgG Molecules Lacking Fcγ Receptor I Binding and Monocyte Triggering Activities" Eur J Immunol 29(8):2613-2624 (1999).
Artandi et al., "Monoclonal IgM rheumatoid factors bind IgG at a discontinuous epitope comprised of amino acid loops from heavy-chain constant-region domains 2 and 3" P Natl Acad Sci USA 89(1):94-98 (Jan. 1, 1992).
Baca et al., "Antibody humanization using monovalent phage display" J Biol Chem 272(16):10678-10684 (1997).
Bloom et al., "Intrachain disulfide bond in the core hinge region of human IgG4" Protein Sci 6:407-415 (1997).
Bolland et al., "SHIP modulates immune receptor responses by regulating membrane association of Btk" Immunity 8(4):509-516 (Apr. 1998).
Boyd et al. et al., "The Effect of the Removal of Sialic Acid, Galactose and Total Carbohydrate on the Functional Activity of Campath-1H." Mol Immunol 32:1311-1318 (1995).
Brambell, "The Transmission of Immunity from Mother to Young and the Catabolism of Immunoglobulins" Lancet 2:1087-1093 (Nov. 19, 1966).
Bredius et al., "Role of neutrophil FcγRIIa (CD32) and FcγRIIIb (CD16) polymorphic forms in phagocytosis of human IgG1- and IgG3-opsonized bacteria and erythrocytes" Immunology 83(4):624-630 (Dec. 1994).
Brekke and Sandlie et al., "Therapeutic antibodies for human diseases at the dawn of the twenty-first century" Nat Rev Drug Discov 2(1):52-62 (Jan. 2003).
Brekke et al., "Structure-Function Relationships of Human IgG" Immunologist 2:125-130 (1994).
Brekke et al., "Human IgG Isotype-Specific Amino Acid Residues Affecting Complement-Mediated Cell Lysis and Phagocytosis." Eur J Immunol 24(10);2542-2541 (Oct. 1994).
Brennan et al., "Preparation of bispecific antibodies by chemical recombination of monoclonal immunoglobulin $G_1$ fragments" Science 229:81-83 (1985).
Brodeur et al. Monoclonal Antibody Production Techniques and Applications New York: Marcel Dekker, Inc.,:51-63 (1987).
Bruggemann et al., "Comparison of the effector functions of human immunoglobulins using a matched set of chimeric antibodies" J Exp Med 166(5):1351-61 (Nov. 1987).
Burmeister et al., "Crystal Structure of the Complex of Rat Neonatal Fc Receptor with Fc." Nature 372(6504):379-383 (Nov. 24, 1994).
Burton et al., "Human Antibody Effector Function" Adv Immunol 51:1-84 (1992).
Burton et al., "The Clq Receptor Site on Immunoglobulin G." Nature 288(5789):338-344 (Nov. 27, 1980).
Burton, D., "Immunoglobulin G: Functional sites" Mol Immunol 22(3):161-206 (1985).
Burton. et al., "Molecular recognition of antibody (IgG) by cellular Fc receptor (FcRI)" Mol Immunol 25(11):1175-1181 (1988).
Byrn et al. et al., "Biological Properties of CD4 Immunoadhesin" Nature 344:667-670 (Apr. 12, 1990).
Cameron, Deborah J., "Specificity of Macrophage-Mediated Cytotoxicity: Role of Target and Effector Cell Fucose." Immunol Lett 11:39-44 (1985).
Canfield et al., "The Binding Affinity of Human IgG for its High Affinity Fc Receptor is Determined by Multiple Amino Acids in the $C_H2$ Domain and is Modulated by the Hinge Region." J Exp Med 173(6):1483-1491 (Jun. 1, 1991).
Capel et al., "Heterogencity of human IgG Fc receptors" Immunomethods 4:35-34 (1994).

(56) References Cited

OTHER PUBLICATIONS

Capon et al., "Designing CD4 Immunoadhesins for AIDS Therapy" Nature 337:525-531 (Feb. 9, 1989).
Carroll et al., "Extensive C1q-Complement Initiated Lysis of Human Platelets by IgG Subclass Murine Monoclonal Antibodies to the CD9 Antigen" Thrombosis Research 59:831-839 (1990).
Carter et al., "Improved oligonucleotide site-directed mutagenesis Using M13 vectors" Nucl Acids Res 13(12):4431-4443 (1985).
Chappel et al., "Identification of Secondary FcγRI Binding Site within a Genetically Engineered Human IgG Antibody" J Biol Chem 268:25124-251131 (1993).
Chappel et al., "Indentification of the Fcγ Receptor Class I Binding Site in Human IgG Through the use of Recombinant IgG1/IgG2 Hybrid and Point-Mutated Antibodies." P Natl Acad Sci USA 88(20):9036-9040 (Oct. 15, 1991).
Chari et al., "Immunoconjugates containing novel maytansinoids: Promising anticancer drugs" Cancer Res 52:127-131 (Jan. 1992).
Charlton, K.A., "Expression and isolation of recombinant antibody fragments in E. coli" Method molec biol 248:245-254 (2003).
Chen et al., "Selection and analysis of an optimized anti-VEGF antibody: crystal structure of an affinity-matured Fab in complex with antigen" J Mol Biol 293(4):865-881 (1999).
Chin and Schultz, "In vivo photocrosslinking with unnatural amino acid mutagenesis" Chembiochem 11:1135-1137 (2002).
Chin et al., "Addition of a photocrosslinking amino acid to the genetic code of Escherichia coli" P Natl Acad Sci USA 99(17):11020-11024 (Aug. 2002).
Chin et al., "Addition of p-Axido-L-phenylalanine to the genetic code of escherichia coli" J Am Chem Soc 124:9026-9027 (2002).
Chothia et al., "Canonical structures for the hypervariable regions of immunoglobulins" J Mol Biol 196:901-917 (1987).
Chowdhury, "Engineering hot spots for affinity enhancement of antibodies" Methods Molec Biol 207:179-196 (2008).
Clackson et al., "Making antibody fragments using phage display libraries" Nature 352:624-628 (Aug. 1991).
Clark et al., "Molecular Basis for a Polymorphism Involving Fc Receptor II on Human Monocytes" Journal of Immunology 5:1731-1734 (1989).
Clark, "IgG effector mechanisms" Chem Immunol. 65:88-110 (1997).
Clynes et al., "Cytotoxic antibodies trigger inflammation through Fc receptors" Immunity 3(1):21-26 (Jul. 1995).
Clynes et al., "Fc receptors are required in passive and active immunity to melanoma" P Natl Acad Sci USA 95:652-656 (Jan. 1998).
Clynes et al., "Inhibitory Fc Receptors Modulate in Vivo Cytoxicity Against Tumor Targets" Nature Med. 6(4):443-446 (Apr. 2000).
Clynes et al., "Modulation of immune complec-induced inflammation in vivo by the coordinate expression of activation and inhibitory Fc receptors" J Exp Med 189(1):179-185 (Jan. 4, 1999).
Clynes et al., "Uncoupling of immune complex formation and kidney damage in autoimmune glomerulonephritis" Science 279(5353):1052-1054 (Feb. 13, 1998).
Cook et al., "Identification of Contact Residues in the IgE Binding Side of Human FcεRIα" Biochemistry 36(50):15579-15588 (Dec. 1997).
Extended European Search Report in EP Appln. No. 11 16 0251.
International Search Report and Written Opinion of the International Searching Authority on patentability for International Patent Application No. PCT/EP2012/055393.
Cosimi, "Clinical Development of Orthoclone OKT3" Transplant P 19(2 Suppl Suppl 1):7-16 (Apr. 1987).
Cragg et al., "Antibody specificity controls in vivo effector mechanisms of anti-CD20 reagents" Blood 103(7):2738-2743 (2004).
Cragg et al., "Complement-mediated lysis by anti-CD20 mAb correlates with segregation into lipid rafts" Blood 101(3):1045-1052 (2003).
Cunningham et al., "High-resolutions epitope mapping of hGH-receptor interactions by alanine-scanning mutagenesis" Science 244:1081-1085 (Jun. 2, 1989).
Daeron, M., "Fc receptor biology" Annu Rev Immunol 15:203-234 (1997).
Dall'Acqua et al., "Modulation of the effector functions of a human IgG1 through engineering of its hinge region" J Immunol. 177:1129-38 (2006).
Dall'Acqua et al., "Antibody humanization by framework shuffling" Methods 36:43-60 (2005).
Dall'Acqua et al., "Increasing the affinity of a human IgG1 for the neonatal Fc receptor: biological consequences" J Immunol 169(9):5171-5180 (Nov. 1, 2002).
Dall'Acqua et al., "Properties of human IgG1s engineered for enhanced binding to the neonatal Fc receptor (FcRn)" J Biol Chem 281(33):23514-24 (Aug. 2006).
Dard et al., "DNA Sequence Variability of IGHG3 Alleles Associated to The Main G3m Haplotypes in Human Populations" European Journal of Human Genetics 9:765-772 (2001).
Datta-Mannan et al., "Humanized IgG1 variants with differential binding properties to the neonatal Fc receptor: relationship to pharmacokinetics in mice and primates" Drug Metab Dispos 35(1):89-94 (Jan. 2007).
Datta-Mannan et al., "Monoclonal antibody clearance. Impact of modulating the interaction of IgG with the neonatal Fc receptor" J Biol Chem 282(3):1709-17 (Jan. 19, 2007).
Davies et al., "Expression of GnTIII in a Recombinant Anti-CD20 CHO Production Cell Line: Expression of Antibodies with Altered Glycoforms Leads to an Increase in ADCC Through Higher Affinity for FcγRIII" Biotechnol Bioeng. 74(4):288-294 (2001).
Davis et al., "Fc receptor homologs: newest members of a remarkably diverse Fc receptor gene family" Immunological Reviews 190:123-136 (2002).
De Haas et al., "Fcγ receptors of phagocytes" J Lab Clin Med 126:330-341 (Oct. 1995).
De Reys et al., "Human platelet aggregation by murine monoclonal antiplatelet antibodies is subtype-dependent" Blood 81:1792-1800 (1993).
De Vita et al. et al., "Efficacy of Selective B Cell Blockade in the Treatment of Rheumatoid Arthritis" Arthritis Rheum 46(8):2029-2033 (Aug. 2002).
Deisenhofer, J, "Crystallographic Refinement and Atomic Models of a Human Fc Fragment and Its Complex with Fragment B of Protein A from Staphylococcus aureus at 2.9- and 2.8-A Resolution" Biochemisty-US 20(9):2361-2370 (1981).
Deng et al. et al., "Pharmacokinetics of Humanized Monoclonal Anti-Tumor Necrosis Factor-α Antibody and Its Neonatal Fc Receptor Variants in Mice and Cynomolgus Monkeys" Drug Metab Dispos 38(4):600-605 (2010).
DeReys et al., "Human Platelet Aggregation by Murine Monoclonal Antiplatelet Antibodies is Subtype-Dependent" Blood 7:1792-1800 (1993).
Dorai et al, et al., "Aglycosylated Chimeric Mouse/Human IgG1 Antibody Retains Some Effector Function." Hybridoma 10(2):211-217 (1991).
Dubowchik et al., "Doxorubicin immunoconjugates containing bivalent, lysosomally-cleavable dipeptide linkages" Bioorg Med Chem Lett 12:1529-1532 (2002).
Duncan and Winter, "The Binding Site for C1q on IgG" Nature 332:738-740 (Apr. 21, 1988).
Duncan et al., "Localization of the Binding Site for the Human High-Affinity Fc Receptor on IgG." Nature 332:563-564 (Apr. 7, 1988).
Eccles et al., "Monoclonal antibodies targeting cancer: 'magic bullets' or just the trigger?" Breast Cancer Research 3(2):86-90 (2001).
El-Amine et al., "In vivo induction of tolerance by an Ig peptide is not affected by the deletion if FcR or a mutated IgG Fc fragment" Int Immunol. 14(7):761-6 (Jul. 2002).
Elbein, Alan D., "Glycosidase Inhibitors: Inhibitors of N-Linked Oligosaccharide Processing" FASEB J 5:3055-3063 (1991).
Ellison et al. et al., "Linkage and sequence homology of two human immunoglobulin gamma heavy chain constant region genes" P Natl Acad Sci USA 79:1984-1988 (Mar. 1982).

(56) References Cited

OTHER PUBLICATIONS

Ellman et al., "Biosynthetic method for introducting unnatural amino acids site-specifically into proteins" Meth Enzym 202:301-336 (1991).
Fellouse et al., "Synthetic antibodies from a four-amino-acid code: A dominant role for tyrosine in antigen recognition" P Natl Acad Sci USA 101(34)12467-12472 (Aug. 24, 2004).
Ferrara et al., "Clinical applications of angiogenic growth factors and their inhibitors" Nat Med 5(12):1359-1364 (Dec. 1999).
Ferrara et al., "Modulation of therapeutic antibody effector functions by glycosylation engineering: influence of Golgi enzyme localization domain and co-expression of heterologous beta1, 4-N-acetylglucosaminyltransferase III and Golgi alpha-mannosidase II" Biotechnology and Bioengineering 93(5):851-861 (2006).
Flatman et al., "Process analytics for purification of monoclonal antibodies" J Chromatogr 848:79-87 (2007).
Fridman, W., "Fc receptors and immunoglobulin binding factors" Faseb J 5(12):2684-2690 (Sep. 1991).
Fundamental Immunology, Paul, W.E., 2nd edition, New York: Raven Press pp. 60 and 61 (1989).
Gavin et al. Chapter 2: The Immunoglobulin Receptors and their Physiological and Pathological Roled in immunity "Molecular basis for hte interaction of Fc receptors with immunoglobulins" J.G.J. van de Winkel and P.M. Hogarth, The Netherlands,: Kluwer Academic Pulblishers,: 11-35 (1998).
Gazzano-Santoro et al., "A non-radioactive complement-dependent cytotoxicity assay for anti-CD20 monoclonal antibody" J Immunol Methods 202:163-171 (1997).
Gergely et al., "Fc Receptors on Lymphocytes and K Cells." Biochem Soc T 12(5):739-743 (Oct. 1984).
Gerngros, "Advances in the production of human therapeutic proteins in yeasts and filamentous fungi" Nature Biotechnology 22(11):1409-1414 (Nov. 2004).
Gessner et al. et al., "The IgG Fc Receptor Family" Ann Hematol 76:231-248 (1998).
Ghebrehiwet et al., "Isolation, cDNA cloning, and overexpression of a 33-kD cell surface glycoprotein that binds to the globular "heads" of C1q" J Exp Med 179(6):1809-1821 (Jun. 1, 1994).
Ghetie and Ward, "FcRn: the MHC class I-related receptor that is more than an IgG transporter" Immunol Today 18(12):592-598 (Dec. 1997).
Ghetie et al., "Abnormally short serum half-lives of IgG in β2-microglobulin-deficient mice" Eur J Immunol 26(3):690-696 (Mar. 1996).
Ghetie et al., "Increasing the serum persistence of an IgG fragment by random mutagenesis" Nat Biotechnol 15(7):637-640 (Jul. 1997).
Gillies et al., "MRI of the tumor microenvironment" J Magn Reson Imaging 16(4):430-50 (Oct. 2002).
Glennie and Johnson et al., "Clinical Trials of Antibody Therapy" Immunol Today 21(8):403-410 (2000).
Goding, Monoclonal Antibodies: Principles and Practice Production and Application of Monoclonal Antibodies in Cell Biology, Biochemistry and Immunology Academic Press,:56-103 (1986).
Gorman et al., "Transient Production of Proteins Using an Adenovirus Transformed Cell Line" DNA Prot Eng Tech 2(1):3-10 (1990).
Graham et al., "Characteristics of a Human Cell Line Transformed by DNA from Human Adenovirus Type 5" J Gen Virol 36:59-72 (1977).
Greenwood et al., "Engineering multiple-domain forms of the therapeutic antibody CAMPATH-1H: effects on complement lysis" Therapeutic Immunology 1(5):247-255 (Oct. 1994).
Greenwood et al., "Structural motifs involved in human IgG antibody effector functions" Eur J Immunol 23(5):1098-1104 (May 1993).
Griffiths et al., "Human anti-self antibodies with high specificity from phage display libraries" Embo J 12(2):725-734 (Feb. 1993).
Groenink et al., "On the interaction between agalactosyl IgG and Fcγ receptors" Eur. J. Immunol. 26:1404-1407 (1996).
Gruber et al., "Efficient tumor cell lysis mediated by a bispecific single chain antibody expressed in *Escherichia coli*" J Immunol 152:5368-5374 (1994).
Guddat et al., "Three-dimensional structure of a human immunoglobulin with a hinge deletion" P Natl Acad Sci USA 90:4271-4275 (1993).
Gurbaxni and Morrison, "Development of new models for the analysis of Fc-FcRn interactions" Mol Immunol. 43:1379-89 (2006).
Guyer et al., "Immunoglobulin binding by mouse intestinal epithelial cell receptors" J Immunol 117(2):587-593 (Aug. 1976).
Haagen et al., "Interaction of Human Monocyte Fcγ Receptors with Rat IgG2b: A New Indicator for the FcγRIIa (R-H131) Polymorphism" J Immunol 154:1852-1860 (1995).
Hadley et al., "The functional activity of FcγRII and FcγRIII on subsets of human lymphocytes" Immunology 76(3)446-451 (Jul. 1992).
Hand et al., "Comparative Biological Properties of a Recombinant Chimeric Anti-Carcinoma mAb and a Recombinant Aglycosylated Variant" Cancer Immunoal. Immunother 35:165-174 (1992).
Harlow and Lane Antibodies. A Laboratory Manual, New York: Cold Spring Harbor Laboratory pp. 321-358 (1988).
Harlow and Lane Antibodies: A Laboratory Manual Cold Spring Harbor, N.Y.:Cold Spring Harbor Laboratory, vol. Chap. 14 (1988).
Harris et al., "Crystallographic Structure of an Intact IgG1 Monoclonal Antibody" J Mol Biol 275:861-872 (1998).
Harris et al., "Refined Structure of an Intact IgG2a Monoclonal Antibody" Biochemistry-US 36:1581-1597 (1997).
Hashim and Cushley et al., "Role of Processing of N-Linked Oligosaccharides in Control of Secretion from Rat Hybridomas" Mol Immunol 24:1087-1096 (1987).
Hashim and Cushley et al., "Simultaneous Inhibition of Multiple Steps in the Processing of N-Linked Oliogosaccharides Does Not Impair Immunoglobulin Secretion From Rat Hybridoma Cells." Immunology 63:383-388 (1988).
Hatta et al., "Association of Fcγ Receptor IIIB, But Not of Fcγ Receptor IIA and IIIA, Polymorphisms with Systemic Lupus Erthematosus in Japanese." Genes Immun 1:53-60 (1999).
Heiken et al., "T lymphocyte development in the absence of Fcε receptor Iγ subunit: analysis of thymic-dependent and independent αβ and γδ pathways" Eur J Immunol 26(8):1938-1943 (Aug. 1996).
Hellstrom et al., "Antitumor effects of L6, an IgG2 antibody that reacts with most human carcinomas" P Natl Acad Sci USA 83:7059-7063 (Sep. 1986).
Hellstrom et al., "Strong antitumor activities of IgG3 antibodies to a human melanoma-associated ganglioside" P Natl Acad Sci USA 82:1499-1502 (Mar. 1985).
Henry et al., "Participation of the N-terminal region of Cε3 in the binding of human IgE to its high-affinity receptor FεRI" Biochemistry-US 36:15568-15578 (1997).
Hessell et al., "Fc receptor but not complement binding is important in antibody protection against HIV" Nature 449:101-105 (Sep. 6, 2007).
Hezareh et al., "Effector function activities of a panel of mutants of a broadly neutralizing antibody against human immunodeficiency virus type 1" J Virol 75(24):12161-8 (Dec. 2001).
Hills et al., "Metabolic control of recombinant monoclonal antibody N-glycosylation in GS-NS0 cells" Biotechnol Bioeng 75:239-251 (2001).
Hinman et al., "Preparation and characterization of monoclonal antibody conjugates of the calicheamicins: A novel and potent family of antitumor antibodies" Cancer Res 53:3336-3342 (Jul. 15, 1993).
Hinton et al., "An engineered human IgG1 antibody with longer serum half-life" J Immunol 176(1):346-56 (2006).
Hinton et al., "Engineered human IgG antibodies with longer serum half-lives in primates" J Biol Chem 279(8):6213-6216 (Feb. 20, 2004).
Hobbs et al. et al., "Interaction of Aglycosyl Immunoglobulins with the IgG Fc Transport Receptor From Neonatal Rat Gut: Comparison of Deglycosylation by Tunicamycin Treatment and Genetic Engineering." Mol Immunol 29:949-956 (1992).

(56) References Cited

OTHER PUBLICATIONS

Hogarth et al., "Characterization of FcR Ig-binding sites and epitope mapping" Immunomethods 4(1):17-24 (Feb. 1994).
Holliger et al., "Diabodies': Small bivalent and bispecific antibody fragments" P Natl Acad Sci USA 90:6444-6448 (Jul. 1993).
Hoogenboom et al., "Overview of antibody phage-display technology and its applications" Methods Mol Biol 178:1-37 (2002).
Houck et al., "The Vascular Endothelial Growth Factor Family: Identification of a Fourth Molecular Species and Characterization of Alternative Splicing of RNA" Mol Endocrinal 5(12):1806-14 (1991).
Hudson et al., "Engineered antibodies" Nature Medicine 9(1):129-134 (Jan. 2003).
Hudziak et al., "p185$^{HER2}$ monoclonal antibody has antiproliferative effects in vitro and sensitizes human breast tumor cells to tumor necrosis factor" Mol Cell Biol 9(3):1165-1172 (Mar. 1989).
Huizinga et al., "Binding Characteristics of Dimeric IgG Subclass Complexes to Human Neutrophils" J Immunol 142:2359-2364 (1989).
Hulett et al., "Chimeric Fc Receptors Identify Functional Domains of the Murine High Affinity Receptors for IgG" J Immunol 147:1863-1868 (1991).
Hutchins et al., "Improved biodistribution, tumor targeting, and reduced immunogenicity in mice with a immunogenicity with a γ4 variant of Campath-1H4 variant of Campath-1H" P Natl Acad Sci USA 92:11980-11984 (Dec. 1995).
Idusogie et al., "Engineered Antibodies with Increased Activity to Recruit Complement" J Immunol 166(4):2571-2575 (Feb. 15, 2001).
Idusogie et al., "Mapping of the C1q Binding Site on Rituxan, A Chimeric Antibody with a Human IgG1 Fc" J Immunol 164(8):4178-4184 (2000).
Israel et al., "Increased clearance of IgG in mice that lack beta 2-microglobulin: possible protective role of FcRn" Immunology 89(4):573-8 (Dec. 1996).
Jaakkola et al., "In vivo detection of vasvular adhesion protein-1 in experimental inflammation" Am J Pathol 157(2):463-471 (Aug. 2000).
Janeway et al. Immunobiology, The Immune System in Health and Disease CB Ltd and Garland Publishing Inc., NY & London,:3-29-3:30 (1994).
Jarvis and Finn et al., "Biochemical Analysis of the N-Glycosylation Pathway in Baculovirus-Infected Lepidopteran Insect Cells" Virology 212:500-511 (1995).
Jassal et al., "Sialylation of Human IgG-Fc Carbohydrate by Transfected Rat α2,6-Sialyltransferase" Biochem Bioph Res Co 286:243-249 (2001).
Jefferis and Lund, "Interaction sites on human IgG-Fc and FcγR: current models" Immunol Lett 82(1-2):57-65 (2002).
Jefferis et al. et al., "A Comparative Study of the N-Linked Oliogsaccharide Structures of Human IgG Subclass Proteins" Biochem J 268:529-537 (1990).
Jefferis et al. et al., "IgG-Fc-Mediated Effector Functions: Molecular Definition of Interaction Sites for Effector Ligands and the Role of Glycosylation." Immunol Rev 163:59-76 (1998).
Jefferis et al. et al., "Recognition sites on human IgG for Fcγ receptors: the role of glycosylation" Immunol Lett 44:111-117 (1995).
Jefferis et al., "Molecular Definition of Interaction Sites on Human IgG for Fc Receptors (huFcγR)" Mol Immunol 27(12):1237-1240 (1990).
Jeffrey et al., "Dipeptide-based highly potent doxorubicin antibody conjugates" Bioorganic Med Chem Letters 16:358-362 (2006).
Jensen et al., "Rapid tumor lysis in a patient with B-cell chronic lymphocytic leukemia and lymphocytosis treated with an anti-CD20 monoclonal antibody (IDEC-C2B8, rituximab)" Annals of Hematology 77(1-2):89-91 (Jul.-Aug. 1998).
Jones et al., "The mechanism of intestinal uptake and transcellular transport of IgG in the neonatal rat" J Clin Invest. 51(11):2916-27 (Nov. 1972).

Kabat et al. Sequences of Proteins of Immunological Interest (Table of Contents, Introduction and Constant Region Sequences sections), 5th edition, Bethesda, MD:NIH, vol. 1:647-723 (1991).
Kam et al., "Carbon nanotubes as multifunctional biological transporters and near-infrared agents for selective cancer cell destruction" P Natl Acad Sci USA 102(33):11600-11605 (Aug. 2005).
Kamei et al., "Quantitative methods for developing Fc mutants with extended half-lives" Biotechnol Bioeng. 92(6):748-60 (Dec. 2005).
Kaneko et al., "Anti-inflammatory activity of immunoglobulin G resulting from Fc sialylation" Science 313:670-673 (Aug. 2006).
Kaneko et al., "Optimizing therapeutic antibody function progress with Fc domain engineering" Biodrugs 25(1):1-11 (2011).
Kashmiri et al., "SDR grafting—a new approach to antibody humanization" Methods 36:25-34 (2005).
Kanushal and Elbein et al., "Glycosidase Inhibitors in Study of Glycoconjugates" Method Enzymol 230:316-329 (1994).
Kilmartin et al. et al., "Rat Monoclonal Antitubulin Antibodies Derived by Using a New Nonsecreting Rat Cell Line" J Cell Biol 93:576-582 (Jun. 1982).
Kim et al. et al., "Catabolism of the Murine IgG1 Molecule: Evidence That Both CH2-CH3 Domain Interfaces are Required for Persistance of IgG1 in the Ciculation of Mice" Scand J Immunol 40(4):457-465 (1994).
Kim et al. et al., "The Vascular Endothelial Growth Factor Proteins: Identification of Biologically Relevant Regions by Neutralizing Monoclonal Antibodies" Growth Factors 7:53-64 (1992).
Kim et al., "Identifying Amino Acid Residues that Influence Plasma Clearance of Murine IgG1 Fragments by Site-Directed Mutagenesis." Eur J Immunol 24:542-548 (1994).
Kim et al., "Localization of the site of the murine IgG1 molecule that is involved in binding to the murine intestinal Fc receptor" Eur J Immunoal 24:2429-2434 (1994).
Kindt et al. Kuby Immunology Sixth edition, New York:W. H. Freeman and Company,:91 (2007).
King and Adair et al., "Recombinant Antibodies for the Diagnosis and Therapy of Human Disease." Curr Opin Drug Discovery Develop 2(2):110-117 (1999).
King et al., "Monoclonal antibody conjugates of doxorubicin prepared with branched peptide linkers: Inhibition of aggregation by methoxytriethyleneglycol chains" J Med Chem 45:4336-4343 (2002).
Koene et al., "FcγRIIIa-158V/F Polymorphism Influences the Binding of the IgG by Natural Killer Cell FcγRIIIa, Independently of the FcγRIIIa-48L/R/H Phentype" Blood 90(3):1109-1114 (1997).
Kohler et al., "Continuous cultures of fused cells secreting antibody of predefined specificity" Nature 256:495-497 (Aug. 7, 1975).
Kojima et al. et al., "Characterization of Mouse ST8Sia II (STX) as a Neural Cell Adhesion Molecule-specific Polysialic Acid Synthase" J Biol Chem 271:19457-19463 (1996).
Kojima et al., "Alpha 1,6-linked fucose affects the expression and stability of polysialic acid-carrying glycoproteins in Chinese hamster ovary cells" J. Biochem 124:726-737 (1998).
Kostelny et al., "Formation of a bispecific antibody by the use of leucine zippers" J Immunol 148(5):1547-1553 (Mar. 1, 1992).
Kozbor et al., "A human hybrid myeloma for production of human monoclonal antibodies" J Immunol 133(6):3001-3005 (Dec. 1984).
Kratz et al., "Prodrugs of anthracyclines in cancer chemotherapy" Curr Med Chem 13:477-523 (2006).
Krummen et al., "Executive Summary Engineering CHO Cells to Maximize Sialic Acid Content of Recombinant Glycoproteins" Other Cambridge Healthtech Institute's Fourth Annual Protein Expression Meeting, Hilton McLean, Tysons' Corner, McLean Virginia, (Apr. 5-6, 2001).
Kumpel et al., "Galatosylation of human IgG monoclonal anti-D produced by EBV-transformed B-lymphoblastoid cell lines is dependent on culture method and affects Fc receptor-mediated functional activity" Hum. Antibod. Hybriodomas 5(3):143-151 (1994).
Kunkel, T., "Rapid and efficient site-specific mutagenesis without phenotypic selection" P Natl Acad Sci USA 82:488-492 (Jan. 1985).
Lauvrak et al., "Identification and characterisation of C1q-binding phage displayed peptides" Biochemistry-US 378(12):1509-1519 (Dec. 1997).

(56) References Cited

OTHER PUBLICATIONS

Lazar et al., "Engineered antibody Fc variants with enhanced effector function" Proc Natl Acad Sci U S A. 103(11):4005-10 (Mar. 2006).
Leatherbarrow et al. et al., "Effector Functions of a Monoclonal Aglycosylated Mouse IgG2a: Binding and Activation of Complement Component C1 and Interaction with Human Moncyte Fc Receptor." Mol Immunol 22(4):407-415 (1985).
Lee et al., "Bivalent antibody phage display mimics natural immuoglobulin" J Immunol Methods 284:119-132 (2004).
Lee et al., "High-affinity human antibodies from phage-displayed synthetic Fab libraries with a single framework scaffold" J Mol Biol 340:1073-1093 (2004).
Lehrnbecher et al., "Variant genotypes of FcγRIIIA influence the development of Kaposi's sarcoma in HIV-infected men" Blood 95(7):2386-2390 (2000).
Lehrnbecher et al., "Variant Genotypes of the Low-Affinity Fcγ Receptors in Two Control Populations and a Review of Low-Affinity Fcγ Receptor Polymorphisms in Control and Disease Populations." Blood 94(12):4220-4232 (Dec. 15, 1999).
Levy et al. et al., "Human Lymphoblastoid Lines From Lymph Node and Spleen" Cancer 22:517-524 (Sep. 1968).
Li et al., "Human antibodies for immunotherapy development generated via a human B cell hybridoma technology" P Natl Acad Sci USA 103(10):3557-62 (Mar. 2006).
Li et al., "Optimization of humanized IgGs in glycoengineered Pichia pastoris" Nat Biotechnol 24(2):210-215 (Feb. 2006).
Li et al., "Reconstitution of human FcγRIII cell type specifically in transgenic mice" J Exp Med 183(3):1259-1263 (Mar. 1, 1996).
Lifely et al., "Glycosylation and Biological Activity of CAMPATCH-1H Expressed in Different Cell Lines and Grown Under Different Culture Conditions." Glycobiology 5(8):813-822 (Dec. 1995).
Liu et al. et al., "Characterization of Complex Formation by Humanized Anti-IgE Monoclonal Antibody and Monoclonal Human IgE" Biochemistry-US 34:10474-10482 (1995).
Lode et al., "Targeted therapy with a novel enediyene antibiotic calicheamicin $\theta^I_1$ effectively suppresses growth and dissemination of liver metastases in a syngeneic model of murine neuroblastoma" Cancer Res 58:2925-2928 (Jul. 15, 1998).
Lonberg, "Fully human antibodies from transgenic mouse and phage display platforms" Current Opin Immunol 20:450-459 (2008).
Lonberg, "Human antibodies from transgenic animals" Nat Biotechnol 23(9):1117-1125 (Sep. 2005).
Lorenz et al., "Strong Association Between the Responder Status of the FCγII Receptor and Recurrent Spontaneous Abortion." Eur J Immunogenet 22(5):397-401 (Oct. 1995).
Loyet et al. et al., "Technology comparisons for anti-therapeutic antibody and neutralizing antibody assays in the context of an anti-TNH pharmacokinetic study" J Immunol Methods 345:17-28 (2009).
Lucas et al., "High-level production of recombinant proteins in CHO cells using a dicistronic DHFR intron expression vector" Nucleic Acids Res 24(9):1774-1779 (1996).
Lund et al., "Human FcγRI and Fcγ RII interact with distinct but overlapping sites on human IgG" J Immunol 147(8):2657-2662 (Oct. 15, 1991).
Lund et al., "Multiple binding sites on the $C_H2$ domain of IgG for mouse FcγR11" Mol Immunol 29(1):53-59 (Jan. 1992).
Lund et al., "Multiple Interactions of the IgG with Its Core Oligosaccharide Can Modulate Recognition by Complement and Human Fcγ Receptor I and Influence The Synthesis of Its Oligosaccharide Chains" J Immunol 157:4963-4969 (1996).
Lund et al., "Oligosaccharide-protein interactions in IgG can modulate recognition by Fcγ receptors" Faseb J 9:115-119 (1995).
Macher et al., "Proteins at membrane surfaces—a review of approaches" Mol. BioSyst. 3:705-713 (2007).
Makrides, "Therapeutic Inhibition of the Complement System" Pharmacological Reviews 50(1):59-87 (1998).
Male, D. Immunology, An Illustrated Outline London: Gower Medical Publishing Ltd.,:21-24 (1986).
Malhotra et al. et al., "Glycosylation Changes of IgG Associated with Rheumatoid Arthritis Can Activate Complement Via the Mannose-Binding Protein" Nat Med 1:237-243 (1995).
Marionneau et al. et al., "Susceptibility of Rat Colon Carcinoma Cells to Lymphokine Activated Killer-Mediated Cytotoxicity is Decreased by α1,2-Fucosylation" Int J Cancer 86:713-717 (2000).
Marks and Bradbury Methods Mol Biol, Antibody Engineering "Selection of human antibodies from phage display libraries" Benny K. C. Lo,Humana Press, vol. 248:161-176 (2004).
Marks et al., "By-passing immunization. Building high affinity human antibodies by chain shuffling" Bio/Technology 10:779-783 (Jul. 1992).
Martin et al., "Crystal structure at 2.8 A of an FcRn/heterodimeric Fc complex: mechanism of pH-dependent binding" Mol Cell 7(4):867-877 (Apr. 2001).
Masuda et al., "Enhanced binding affinity for FcγRIIIa of fucose-negative antibody is sufficient to induce maximal antibody-dependent cellular cytotoxicity" Molec Immunol 44:3122-3131 (May 2007).
Mather et al., "Culture of testicular cells in hormone-supplemented serum-free medium" Ann NY Acad Sci 383:44-68 (1982).
Mather, "Establishment and characterization of two distinct mouse testicular epithelial cell lines" Biol Reprod 23:243-252 (1980).
Maxwell et al., "Crystal structure of the human leukocyte Fc receptor, FcγRIIa" Nat Struct Biol 6(5):473-442 (May 1999).
Mayo Clinic Staff, "Goiter" http://www.mayoclinic.com/health/goiter/DS00217/method (Sep. 9, 2011).
McCafferty et al., "Phage antibodies: filamentouse phage displaying antibody variable domains" Nature 348:552-554 (Dec. 6, 1990).
McCarthy et al., "Bidirectional transcytosis of IgG by the rat neonatal Fc receptor expressed in a rat kidney cell line: a system to study protein transport across epithelia" J Cell Sci. 113:1277-85 (Apr. 2000).
Medesan et al., "Comparative studies of rat IgG to further delineate the Fc:FcRN interaction site" Eur J Immunol 28:2092-2100 (1998).
Medesan et al., "Delineation of the amino acid residues involved in transcytosis and catabolism of mouse IgG1" J Immunol 158(5):2211-2217 (Mar. 1, 1997).
Medesan et al., "Localization of the site of the IgG molecule that regulates maternofetal transmission in mice" Eur J Immunol 26(10):2533-2536 (Oct. 1996).
Mellis et al., "Structures of the Oligosaccharides Present at the Three Asparagine-Linked Glycosylation Sites of Human IgD" The Journal of Biological Chemistry 258(19):11546-11556 (Oct. 10, 1983).
Meng et al., "Green fluorescent protein as a second selectable marker for selection of high producing clones from transfected CHO cells" Gene 242:201-207 (2000).
Michaeli et al., "Optimised Fc variants with enhanced effector function" Expert Opinion Ther. Patents 16(10):1449-1452 (2006).
Mikayama et al., "Molecular cloning and functional expression of a cDNA encoding glycosylation-inhibiting factor" Proc. Natl. Acad. Sci. USA 90(21):10056-10060 (Nov. 1, 1993).
Miller et al., "A Novel Role for the Fc Receptor γ Subunit: Enhancement of the FcγR Ligand Affinity" J Exp Med 183:2227-2233 (1996).
Milstein et al., "Hybrid hybridomas and their use in immunohistochemistry" Nature 305:537-540 (Oct. 6, 1983).
Mimura et al. et al., "The influence of glycosylation on the thermal stability and effector function expression of human IgG1-Fc: properties of a series of truncated glycoforms" Mol Immunol 37(12-13):697-706 (Aug. 2000).
Mizushima et al., "Structural Basis for Improved Efficacy of Therapeutic Antibodies on Defucosylation of Their Fc Glycans" Genes to Cells 16:1071-1080 (2011).
Moore et al., "Engineered Fc cariant antibodies with enhanced ability to recruit complement and mediate effector functions" Landes Bioscience 2(2):181-189 (2010).
Morgan et al., "The N-terminal end of the $C_H2$ domain of chimeric human IgG1 anti-HLA-DR is necessary for C1q, FcγRI and FcγRIII binding" Immunology 86(2):319-324 (Oct. 1995).

(56) References Cited

OTHER PUBLICATIONS

Morris, "2 The receptor hypothesis of protein ingestion" Antigen Absorption by the Gut, W. A. Hemmings, Baltimore: University Park Press pp. 3-22 (1978).
Morrison et al., "Structural Determinants of Human IgG Function" Immunologist 2:119-124 (1994).
Murray et al. Harper's Biochemistry "Chapter 4, Amino Acids" Appleton & Lange, 23rd edition,:23-28.
Nagarajan et al., "Ligand binding and phagocytosis by CD16 (Fc γ receptor III) isoforms. Phagocytic signaling by associated ζ and γ subunits in Chinese hamster ovary cells" J Biol Chem 270(43):25762-24770 (Oct. 27, 1995).
Nagy et al., "Stability of cytotoxic luteinizing hormone-releasing hormone conjugate (AN-152) containng doxorubicin 12-O-hemiglutarate in mouse and human serum in vitro: implications for the design of preclinical studies" P Natl Acad Sci USA 97(2):829-34 (Jan. 18, 2000).
Natsume et al., "Improving Effector Functions of Antibodies for Cancer Treatment: Enhancing ADCC and CDC" Drug Design, Development and Therapy 3:7-16 (2009).
Newkirk et al., "Rheumatoid factor avidity in patients with rheumatoid arthritis: identification of pathogenic RFs which correlate with disease parameters and with the gal(0) glycoform of IgG" J Clin Immunol 15(5):250-257 (Sep. 1995).
Newman et al., "Modification of the Fc region of a primatized IgG antibody to human CD4 retains its ability to modulate CD4 receptors but does not deplete CD4(+) T cells in chimpanzees" Clin Immunol 98(2):164-75 (Feb. 2001).
Ngo et al. The Protein Folding Problem and Tertiary Structure Prediction "Computational Complexity and the Levinthal Paradox" Merz & Le Grand, Boston:Birkhauser,:491-506 (1994).
Ni, "Research progress and future perspectives in antibodomics and antibodomic drugs" Xiandai Mianyixue ((Abstract only)), 26(4):265-168 (2006).
Nieto et al., "Involvement of the Fcγ receptor IIIA genotypes in susceptibility to rheumatoid arthritis" Arthritis Rheum 43(4):735-739 (2000).
Niu and Chiu, "FDA perspective on peptide formulation and stability issues" J Pharm Sci 87(11):1331-1334 (Nov. 1998).
Noren et al., "A general method for site-specific incorporation of unnatural amino acids into proteins" Science 244(4901):182-188 (Apr. 14, 1989).
Nose et al. et al., "Biological Significance of Carbohydrate Chains on Monoclonal Antibodies" P Natl Acad Sci USA 80:6632-6636 (Nov. 1983).
Ober et al., "Exocytosis of IgG as mediated by the receptor, FcRn: an analysis at the single-molecule level" Proc Natl Acad Sci U S A. 101(30):11076-81 (Jul. 2004).
Ober et al., "Visualizing the site and dynamics of IgG salvage by the MHC class I-related receptor, FcRn" J Immunol. 172(4):2021-9 (Feb. 2004).
Ober et al., "Differences in promiscuity for antibody—FcRn interactions across species: implications for therapeutic antibodies" International Immunology 13(12):1551-1559 (2001).
Oganesyan et al. et al., "Structural characterization of a human Fc fragment engineered for extended serum half-life" Mol Immunol 46:1750-1755 (2009).
Oganesyan et al., "Structural characterization of a human Fc fragment engineered for lack of effector functions" Acta Cryst D64:700-704 (2008).
Ohyama et al. et al., "Molecular Cloning and Expression of GDP-D-mannose-4,6-Dehydratase, A Key Enzyme for Fucose Metabolism Defective in Lec13 Cells" J Biol Chem 273(23):14582-7 (1998).
Okada et al., "Cutting Edge: Role of the inositol phasphatase SHIP in B cell receptor-induced $Ca^{2+}$ oscillatory response" J Immunol 161(10):5129-5132 (Nov. 15, 1998).
Okafo et al. et al., "Simple Differentiation Between Core-Fucosylated and Nonfucosylated Glycans by Capillary Electrophoresis" Anal Biochem 240:68-74 (1996).

Okazaki et al., "Fucose depletion from human IgG1 oligosaccharide enhances binding enthalpy and association rate between IgG1 and FcgammaRIIIa" J Mol Biol 336(5):1239-1249 (Mar. 5, 2004).
Olafsen et al., "Tunable pharmacokinetics: modifying the in vivo half-life of antibodies by directed mutagenesis of the Fc fragment" Nat Protoc. 1(4):2048-60 (2006).
Ono et al., "Deletion of SHIP or SHP-1 reveals two distinct pathways for inhibitory signaling" Cell 90(2):293-301 (Jul. 25, 1997).
Ono et al., "Role of the inositol phasphatase SHIP in negative regulation of the immune system by the receptor FcγRIIB" Nature 383(6597):263-266 (Sep. 19, 1996).
Osbourn et al., "From rodent reagents to human therapeutics using antibody guided selection" Methods 36:61-68 (2005).
O'Sullivan et al., "Methods for the preparation of enzyme-antibody conjugates for use in enzyme immunoassay" Method Enzymol 73:147-166 (1981).
Padlan, "A possible procedure for reducing the immunogenicity of antibody variable domains while preserving their ligand-binding properties" Mol Immunol 28(4/4):489-498 (1991).
Papac et al., "A high-throughput microscale method to release N-linked oligosaccharide from glycoproteins for matrix-assisted laser desorption/ionization time-of-flight mass spectrometric analysis" Glycobiology 8(5):4445-454 (1998).
Papac et al., "Analysis of Acidic Oligosaccharides and Glycopeptides by Matrix-Assisted Laser Desorption/Ionization Time-of-Flight Mass Spectrometry" Anal Chem 68:3215-3223 (1996).
Parekh et al., "Association of rheumatoid arthritis and primary osteoarthritis with changes in the glycosylation pattern of total serum IgG" Nature 316:452-457 (1985).
Penichet and Morrison et al., "Antibody-Cytokine Fusion Proteins for the Therapy of Cancer" J Immunol Methods 248:91-101 (2001).
Petkova et al., "Enhanced half-life of genetically engineered human IgG1 antibodies in a humanized FcRn mouse model: potential application in humorally mediated autoimmune disease" Int Immunol 18(12):1759-69 (Dec. 2006).
Pluckthun, A. The Pharmacology of Monoclonal Antibodies: Handbook of Pharmacology "Antibodies from *Escherichia coli*" (Chapter 11), Rosenberg and Moore, eds. Berlin Springer-Verlag, vol. 113:269-315 (1994).
Popkov et al., "Human/mouse cross-reactive anti-VEGF receptor 2 recombinant antibodies selected from an immune b9 allotype rabbit antibody library" J Immunol Methods 288:149-164 (May 2004).
Popov et al., "The stoichiometry and affinity of the interaction of murine Fc fragments with the MHC class I-related receptor, FcRn" Mol Immunol 33(6):521-530 (Apr. 1996).
Porges et al., "Novel Fcγ Receptor I Family Gene Products in Human Mononuclear Cells" J Clin Invest 90:2102-2109 (1992).
Portolano et al., "Lack of promiscuity in autoantigen-specifc H and L chain combinations as revealed by human H and L chain 'Roulette'" J Immunol 150(3):880-887 (Feb. 1993).
Prabhat et al., "Elucidation of intracellular recycling pathways leading to exocytosis of the Fc receptor, FcRn, by using multifocal plane microscopy" Proc Natl Acad Sci U S A. 104(14):5889-94 (Apr. 2007).
Praetor et al., "Intracellular traffic of the MHC class I-like IgG Fc receptor, FcRn, expressed in epithelial MDCK cells" J Cell Sci. 112:2291-9 (Jul. 1999).
Presta et al. et al., "Engineering therapeutic antibodies for improved function" Biochemical Society 30:487-490 (2002).
Presta et al., "Humanization of an antibody directed against IgE" J Immunol 151(5):2623-2632 (Sep. 1993).
Presta et al., "Molecular engineering and design of therapeutic antibodies" Current Opinion in Immunology 20:460-470 (2008).
Presta, L. G., "Engineering of therapeutic antibodies to minimize immunogenicity and optimize function" Adv Drug Deliver Rev 58:640-656 (2006).
Presta, Leonard, "Antibody engineering for therapeutics" Curr Opin Struc Biol 13:519-525 (2003).
Presta, Leonard, "Selection, design, and engineering of therapeutic antibodies" J Allergy Clin Immun 116:731-736 (Oct. 2005).

(56) References Cited

OTHER PUBLICATIONS

Queen et al., "A humanized antibody that binds to the interleukin 2 receptors" P Natl Acad Sci USA 86(24):10029-10033 (Dec. 1989).
Radaev et al., "The Structure of a Human Type III Fcγ Receptor in Complex with Fc" Journal of Biological Chemistry 276:16469-16477 (2001).
Raghavan and Bjorkman, "Fc receptors and their interactions with immunoglobulins" Annu Rev Cell Dev Biol 12:181-220 (1996).
Raghavan et al., "Analysis of the pH dependence of the neonatal Fc receptor/immunoglobulin G interaction using antibody and receptor variants" Biochemistry-US 34(45):14649-14657 (Nov. 14, 1995).
Raju et al. et al., "Species-Specific Variation in Glycosylation of IgG: Evidence for the Species-Specific Sialylation and Branch-Specific Galactosylation and Importance for Engineering Recombinant Glycoprotein Therapeutics." Glycobiology 10(5):477-486 (2000).
Ravetch and Bolland, "IgG Fc receptors" Ann Rev Immunol 19:275-290 (2001).
Ravetch and Kinet, "Fc receptors" Annu Rev Immunol 9:457-492 (1991).
Ravetch et al., "Divergent roles for Fc receptors and complement in vivo" Annu Rev Immunol 16:421-432 (1998).
Ravetch, J., "Fc receptors" Curr Opin Immunol 9(1):121-125 (Feb. 1997).
Ravetch, J., "Fc receptors: rubor redux" Cell 78(4):553-560 (Aug. 26, 1994).
Reff et al., "Depletion of B cells in vivo by a chimeric mouse human monoclonal antibody to CD20" Blood 83(2):435-445 (1994).
Repp et al., "Combined Fc-Protein- and Fc-Glyco-Engineering of scFv-Fc Fusion Proteins Synergistically Enhances CD16a Binding but Does Not Further Enhance NK-Cell Mediated ADCC" J. Immunol. Methods 373(1-2):67-78 (Oct. 28, 2011).
Ripka and Stanley et al., "Lectin-Resistant CHO Cells: Selection of Four New Pea Lectin-Resistant Phenotypes" Somat Cell Molec Gen 12(1):51-62 (1986).
Ripka et al., "Two Chinese hamster ovary glycosylation mutants affected in the conversion of GDP-mannose to GDP-fucose" Arch Biochem Biophys 249(2):533-545 (Sep. 1986).
Rodewald, "pH-dependent binding of immunoglobulins to intestinal cells of the neonatal rat" J Cell Biol. 71(2):666-9 (Nov. 1976).
Roopenian and Akilesh, "FcRn: the neonatal Fc receptor comes of age" Nat Rev Immunol 7:715-725 (2007).
Roopenian et al., "The MHC class I-like IgG receptor controls perinatal IgG transport, IgG homeostasis, and fate of IgG-Fc-coupled drugs" J Immunol. 170(7):3528-33 (Apr. 2003).
Rosok et al., "A combinatorial library strategy for the rapid humanization of anticarcinoma BR96 Fab" J Biol Chem 271(37):22611-22618 (Sep. 13, 1996).
Rothman et al. et al., "Antibody-Dependent Cytotoxicity Mediated by Natural Killer Cells is Enhances by Castanospermine-Induced Alterations of IgG Glycosylation" Mol Immunol 26(12):1113-1123 (1989).
Routier et al., "The glycosylation pattern of a humanized IgGI antibody (D1.3) expressed in CHO cells" Glycoconjugate J 14:201-207 (1997).
Rudd et al. et al., "Glycosylation and the Immune System" Science 291:2370-2376 (2001).
Sampson et al. et al., "Unarmed, Tumor-Specific Monoclonal Antibody Effectively Treats Brain Tumors" P Natl Acad Sci USA 97:7503-7508 (Jan. 2000).
Sarmay et al., "Ligand Inhibition Studies on the Role of Fc Receptors in Antibody-Dependent Cell-Mediated Cytotoxicity." Mol Immunol 21(1):43-51 (Jan. 1984).
Sarmay et al., "Mapping and comparison of the interaction sites on the Fc region of IgG responsible for triggering antibody dependent cellular cytotoxicity (ADCC) through different types of human Fcγ receptor" Mol Immunol 29(5):633-639 (May 1992).
Sato, "Molecular diagnosis of tumor angiogenesis and anti-angiogenic cancer therapy" Int J Clin Oncol 8(4):200-206 (Aug. 2003).
Sautes Cell-Mediated Effects of Immunoglobulins "Chapter 2, Structure and Expression of Fc Receptors (FcR)" Wolf Herman Fridman and Catherine Sautes, R.G. Landes Company,:29-66 (1997).
Schlaeth et al., "Fc-engineered EGF-R antibodies mediate improved antibody-dependent cellular cytotoxicity (ADCC) against KRAS-mutated tumor cells" Cancer Science 101(5):1080-1088 (May 2010).
Schrama et al., "Antibody Targeted Drugs as Cancer Therapeutics" Nature Reviews Drug Discovery 5:147-159 (Feb. 2006).
Segal, "Introduction: Bispecific Antibodies" J Immunol Methods 248(1-2):1-6 (Feb. 1, 2001).
Sensel et al., "Amino acid differences in the N-terminus of $C_H2$ influence the relative abilities of IgG2 and IgG3 to activate complement" Mol Immunol 34(14):1019-1029 (Oct. 1997).
Shields et al. et al., "Lack of Fucose on Human IgG1 N-Linked Oligosaccharide Improves Binding to Human FcγRIII and Antibody-dependent Cellular Toxicity" J Biol Chem 277(30):26733-26740 (Jul. 26, 2002).
Shields et al., "High resolution mapping of the binding site on human IgG1 for Fc gamma RI, Fc gamma RII, Fc gamma RIII, and FcRn and design of IgG1 variants with improved binding to the Fc gamma. R" J Biol Chem 276(9):6591-6604 (Mar. 2, 2001).
Shim et al., "One Target, different effects: a comparison of distinct therapeutic antibodies against the same targets" Experimental and Molecular Medicine 43(10):539-549 (Oct. 2011).
Shinkawa et al. et al., "The Absense of Fucose but Not the Presence of Galactose or Bisecting N-Acetyclucosamine of Human IgG1 Complex-type Oligosaccharides Shows the Critical Role of Enhancing Antibody-dependent Cellular Cytotoxicity" J Biol Chem 278(5):3466-3473 (Jan. 31, 2003).
Shitara et al., "A New Vector for the High Level Expression of Chimeric Antibodies in Myeloma Cells" Journal of Immunological Methods 167:271-278 (1994).
Shores et al., "T cell development in mice lacking all T cell receptor ζ family members (ζ, η, and FcεRIγ)" J Exp Med 187(7):1093-1101 (Apr. 6, 1998).
Sidhu et al., "Phage-displayed antibody libraries of synthetic heavy chain complementarity determining regions" J Mol Biol 338(2):299-310 (2004).
Simon et al., "Consolidation treatment with chimeric anti-GD2-antibody ch14.18 in children older than 1 year with metastatic neuroblastoma" J Clin Oncol. 22(17):3549-57 (Sep. 2004).
Sims et al., "A Humanized CD18 Antibody Can Block Function Without Cell Destruction" J Immunol 151(4):2296-2308 (Aug. 15, 1993).
Sondermann et al., "Crystal structure of the soluble form of the human Fcγ-receptor IIb: a new member of the immunoglobulin superfamily at 1.7 A resolution" Embo J 18(5):1095-1103 (1999).
Sondermann et al., "The 3.2-A crystal structure of the human IgG1 Fc fragment-Fc gammaRIII complex" Nature 406(6793):267-273 (2000).
Song et al., "Influence of Tumor pH on Therapeutic Response" Cancer Drug Discovery and Development: Cancer Drug Resistance (2007).
Stankova and Rola-Pleszczynski et al., "Fucose-Activated Killer (FAK) Cells: Anomalous Killers with Augmented Cytotoxic Activity" J Immunol 135(6):3719-3728 (Dec. 1985).
Steeg et al., "Brain Metastases as Preventive and Therapeutic Targets" Nature Review Cancer 11:352-363 (May 2011).
Steplewski et al., "Biological activity of human-mouse IgG1, IgG2, IgG3, and IgG4 chimeric monoclonal antibodies with antitumor specificity" P Natl Acad Sci USA 85(13):4852-4856 (Jul. 1988).
Streit et al., "Angiogenesis, lymphangiogenesis, and melanoma metastasis" Oncogene 22(20):3172-3179 (May 19, 2003).
Strohmeier et al., "Neutrophil functional responses depend on immune complex valency" J Leukocyte Biol 58(4):403-414 (Oct. 1995).
Strohmeier et al., "Role of the FcγR subclasses FcγRII and FcγRIII in the activation of human neutrophils by low and high valency immune complexes" J Leukocyte Biol 58(4):415-422 (Oct. 1995).

(56) References Cited

OTHER PUBLICATIONS

Stubenrauch et al., "Impact of molecular processing in the hinge region of therapeutic IgG4 antibodies on disposition profiles in cynomolgus monkeys" Drug Metab Dispos. 38(1):84-91 (Jan. 2010).
Suzuki et al., "Distinct contribution of Fc receptors and angiotensin II-dependent pathways in anti-GBM glomerulonephritis" Kidney Int 54(4):1166-1174 (Oct. 1998).
Sylvestre and Ravetch, "A dominant role for mast cell Fc receptors in the Arthus reaction" Immunity 5(4):387-390 (Oct. 1996).
Sylvestre et al., "Fc receptors initiate the Arthus reaction: redefining the inflammatory cascade" Science 265(5175):1095-1098 (Aug. 19, 1994).
Sylvestre et al., "Immunoglobulin G-mediated inflammatory responses develop normally in complement-deficient mice" J Exp Med 184(6):2385-2392 (Dec. 1, 1996).
Takahashi et al., "Comparative Structural Study of the N-Linked Oligosaccharides of Human Normal and Pathological Immunoglobulin G" Biochemistry 26(4):1137-1144 (1987).
Takai et al., "Augmented humoral and anaphylactic responses in FcγRII-deficient mice" Nature 379(6563):346-349 (Jan. 25, 1996).
Takai et al., "FcR γ chain deletion results in pleiotrophic effector cell defects" Cell 76(3):519-529 (Feb. 11, 1994).
Tamm et al., "The IgG binding site of human FcγRIIIB receptor involves CC' and FG loops of the membrane-proximal domain" J Biol Chem 271(7):3659-3666 (Feb. 16, 1996).
Tamura, "Human Immunoadhesin A New Ligand Antagonist (English Translation)" Pharmaceutical Society of Japan 33(1):46-50 (1997).
Tao et al., "Structural Features of Human Immunoglobulin G That Determine Isotype-Specific Differences in Complement Activation." J Exp Med 178(2):661-667 (Aug. 1, 1993).
Tao et al., "Studies of Aglycosylated Chimeric Mouse-Human IgG: Role of Carbohydrate in the Structure and Effector Functions Mediated by the Human IgG Constant Region." J Immunol. 143(8):2595-2601 (Oct. 15, 1989).
Tao et al., "The differential ability of human IgG1 and IgG4 to activate complement is determined by the COOH-terminal sequence of the $C_H2$ domain" J Exp Med 173(4):1025-1028 (Apr. 1991).
Tax et al., "Fc receptors for mouse IgG1 on human monocytes: polymorphism and role in antibody-induced T cell proliferation" J Immunol 133(3):1185-1189 (Sep. 1984).
Taylor et al., "In vitro and in vivo activities of OX40 (CD134)-IgG fusion protein isoforms with different levels of immune-effector functions" J Leukoc Biol. 72(3):522-9 (Sep. 2002).
Taylor et al., "Thrombosis and shock induced by activating antiplatelet antibodies in human FcγRIIA transgenic mice: the interplay among antibody, spleen, and Fc receptor" Blood 96(13):4254-4260 (Dec. 2000).
Tejada et al., "Tumor-driven paracrine platelet-derived growth factor receptor alpha signaling is a key determinant of stromal cell recruitment in a model of human lung carcinoma" Clin Cancer Res 12(9):2676-88 (May 2006).
Tesar et al., "Ligand valency affects transcytosis, recycling and intracellular trafficking mediated by the neonatal Fc receptor" Traffic 7(9):1127-42 (Sep. 2006).
Thommesen et al., "Lysine 322 in the human IgG3 C(H)2 domain is crucial for antibody dependent complement activation" Mol Immunol 37(16):995-1004 (Nov. 2000).
Ting et al., "Fcγ receptor activation induces the tyrosine phosphorylation of both phospholipase C (PLC)-γ1 and Plc-γ2 in natural killer cells" J Exp Med 176(6):1751-1755 (Dec. 1, 1992).
Tomiyama et al., "Response of human platelets to activating monoclonal antibodies: Importance of FcγRII (CD32) phenotype and level of expression" Blood 80(9):2261-2268 (1992).
Tonini et al., "Molecular basis of angiogenesis and cancer" Oncogene 22(42):6549-6556 (Sep. 29, 2003).
Torgov et al., "Generation of an intensely potent anthracycline by a monoclonal antibody—β-galactosidase conjugate" Bioconjugate Chem 16:717-21 (2005).

Traunecker et al., "Bispecific Single Chain Molecules (Janusins) Target Cytotoxic Lymphocytes on HIV Infected Cells" Embo J 10(12):3655-3659 (1991).
Tsuchiya et al., "Effects of Falactose Depletion from Oligosaccharide Chains on Immunological Activities of Human IgG" J Rheumatol 16:285-290 (1989).
Tutt et al., "Monoclonal antibody therapy of B cell lymphoma: signaling activity on tumor cells appears more important than recruitment of effectors" Journal of Immunology 161(6):3176-3185 (Sep. 15, 1998).
Tutt et al., "Trispecific F(ab')₃ derivatives that use cooperative signaling via the TCR/CD3 complex and CD2 to activate and redirect resting cytotoxic T cells" J Immunol 147(1):60-69 (Jul. 1991).
Umana et al., "Engineered Glycoforms of an Antineuroblastoma IgG1 with Optimized Antibody-Dependent Cellular Cytotoxic Activity" Nat Biotechnol 17(2):176-180 (Feb. 1999).
Urfer et al., "High resolution mapping of the binding site of TrkA for nerve growth factor and TrkC for neurotrophin-3 on the second immunoglobulin-like domain of the Trk receptors" J Biol Chem 273(10):5829-5840 (Mar. 6, 1998).
Urlaub et al., "Isolation of Chinese hamster cell mutants deficient in dihydrofolate reductase activity" P Natl Acad Sci USA 77(7):4216-4220 (Jul. 1980).
Vallette et al., "Construction of mutant and chimeric genes using the polymerase chain reaction" Nucl Acids Res 17(2):723-733 (1989).
van de Winkel et al., "Biology of human immunoglobulin G Fc receptors" J Leukocyte Biol 49(5):511-524 (May 1991).
Vance et al., "Binding of monomeric human IgG defines an expression polymorphism of FcγRIII on large granular lymphocyte/natural killer cells" J Immunol 151(11):6429-6439 (Dec. 1, 1993).
Vaswani and Hamilton, "Humanized Antibodies as Potential Therapeutic Drugs" Ann. Allergy Asthma Immunol. 81:105-119 (Aug. 1998).
Vitetta et al., "Considering Therapeutic Antibodies" Science 313:308-309 (Jul. 21, 2006).
Vitetta et al., "Redesigning nature's poisons to create anti-tumor reagents" Science 238:1098-1104 (1987).
Vollmers and Brandlein, "Death by stress: natural IgM-induced apoptosis" Methods Find Exp Clin Pharmacol 27(3):185-191 (2005).
Vollmers and Brandlein, "The 'early birds': Natural IgM antibodies and immune surveillance" Histol Histopathol 20:927-937 (2005).
Walker et al. et al., "Aglycosylation of Human IgG1 and IgG3 Monoclonal Antibodies Can Eliminate Recognition by Human Cells Expressing FcγRI and/or FcγRII Receptors." Biochem J 259:347-353 (1989).
Wang and Schultz, "Expanding the genetic code" Chem Commun:1-10 (2002).
Ward et al., "The Effector Functions of Immunoglobulins: Implications for Therapy." Therapeutic Immunology 2(2):77-94 (1995).
Warmerdam et al., "A Single Amino Acid in the Second Ig-Like Domain of the Human Fcγ Receptor II is Critical for Human IgG2 Binding" J Immunol 147(4):1338-1343 (Aug. 15, 1991).
Waterhouse et al., "Combinatorial infection and in vivo recombination: a strategy for making large phage antibody repertoires" Nucl Acids Res 21(9):2265-2266 (1993).
Watt et al., "Site-specific glycosylation of an aglycosylated human IgG1-Fc antibody protein generates neoglycoproteins with enhanced function" Chem Biol. 10(9):807-14 (Sep. 2003).
Wawrzynczak et al. et al., "Blood Clearance in the Mouse of an Aglycosyl Recombinant Monoclonal Antibody" Biochem Soc T 17:1061-1062 (1989).
Wawrzynczak et al. et al., "Blood Clearance in the Rat of a Recombinant Mouse Monoclonal Antibody Lacking the N-Linked Oligosaccharide Side Chains of the $C_H2$ Domains" Mol Immunol 29(2):213-220 (1992).
Wawrzynczak et al., "Recombinant Mouse Monoclonal Antibodies with single Amino Acid Substitutions Affecting C1q and High Affinity Fc Receptor Binding Have Identical Serum Half-lives in the BALB/c Mouse" Molecular Immunology 29(2):221-227 (1992).
Weis et al. et al., "The C-Type Lectin Superfamily in the Immune System" Immunol Rev 163:19-34 (1998).

(56) References Cited

OTHER PUBLICATIONS

Wells et al., "Cassette mutagenesis: An efficient method for generation of multiple mutations at defined sites" Gene 34:315-323 (1985).
Weng et al., "Computational determination of the structure of rat Fc bound to the neonatal Fc receptor" J Mol Biol 282(2):217-225 (Sep. 18, 1998).
Werther et al., "Humanization of an Anti-Lymphocyte Function-Associated (LFA)-1 Monoclonal Antibody and Reengineering of the Humanized Antibody for Binding to Rhesus LFA-1" J Immunol 157:4986-4995 (1996).
Williams et al., "Heteroclitic polyclonal and monoclonal anti-Gm(a) and anti-Gm(g) human rheumatoid factors react with epitopes induced in Gm(a−), Gm(g−) IgG by interaction with antigen or by nonspecific aggregation" J Immunol 149(5):1817-1824 (Sep. 1, 1992).
Winter et al., "Making antibodies by phage display technology" Annu Rev Immunol 12:433-455 (1994).
Woof et al., "Localisation of the Monocyte-Binding Region on Human Immunoglobulin G." Mol Immunol 23(3):319-330 (Mar. 1986).
Wright and Morrison et al., "Effect of altered $C_H2$-associated carbohydrate structure on the functional properties and in vivo fate of chimeric mouse-human immunoglobulin G1" J Exp Med 180(3):1087-1096 (Sep. 1, 1994).
Wright and Morrison, "Effect of C2-associated carbohydrate structure on Ig effector function: Studies with chimeric mouse-human IgG1 antibodies in glycosylation mutants of Chinese Hamster Ovary cells" J Immunol 160:3393-3402 (1998).
Wright and Morrison, "Effect of glycosylation on antibody function: Implications for genetic engineering" Trends Biotechnol 15:26-32 (1997).
Wu et al., "A Novel Polymorphism of FcγRIIIa (CD16) Alters Receptor Function and Predisposes to Autoimmune Disease." J Clin Invest 100(5):1059-1070 (Sep. 1, 1997).
Xie et al. et al., "Direct demonstration of MuSK involvement in acetylcholine receptor clustering through identification of agonist scFv." Nat Biotechnol 15:768-771 (Aug. 1997).
Xu et al., "In vitro characterization of five humanized OKT3 effector function variant antibodies" Cell Immunol 200:16-26 (2000).
Xu et al., "Residue at position 331 in the IgG1 and IgG4 CH2 domains contributes to their differential ability to bind and activate complement" J Biol Chem 269(5):3469-3474 (Feb. 4, 1994).
Xu et al., "The N-Terminal Sequence of the $C_H2$ Domain Controls the Differential Ability of Human IgG1 and IgG2 to Activate Complement." J Immunol (abstract No. 862), 150(8):152A (Apr. 15, 1993).
Yap et al., "Human Fc Gamma Receptor IIA (FcγRIIA) Genotyping and Association with Systemic Lupus Erthematosus (SLE) in Chinese and Malays in Malaysia." Lupus 8(4):305-310 (1999).
Yazaki et al., "Expression of recombinant antibodies in mammalian cell lines" Methods Molec Biol 248:255-268 (2004).
Yeung et al. et al., "A Therapeutic Anti-VEGF Antibody with Increased Potency Independent of Pharmacokinetic Half-life" Cancer Res 70(8):3269-3277 (2010).
Yeung et al., "Engineering Human IgG1 Affinity to Human Neonatal Fc Receptor: Impact of Affinity Improvement on Pharmacokinetics in Primates" Journal of Immunology 182:7663-7671 (2009).
Yuan et al., "Antibody-mediated modulation of Cryptococcus neoformans infection is dependent on distinct Fc receptor functions and IgG subclasses" J Exp Med 187(4):641-648 (Feb. 16, 1998).
Zheng et al., "Administratin of noncytolytic IL-10/Fc in murine models of lipopolysaccharide-induced septic shock and allogeneic islet transplantation" J Immunol 154(10):5590-600 (May 1995).
Zola Monoclonal Antibodies: A Manual of Techniques "Chapter 6 Using Monoclonal Antibodies: soluble Antigens"CRC Press,:147-158 (1987).
Jackson et al., "Human retinal molecular weight exclusion limit and estimate of species variation" Investigative Ophthalmology & Visual Science 44(5):2141-2146 (2003).
Zhang et al., "Ophthalmic drug discovery: novel targets and mechanisms for retinal diseases and glaucoma" Nature Reviews|Drug Discovery 11:541-559 (Jul. 2012).
Yadav, S. et al., "Establishing a Link Between Amino Acid Sequences and Self-Associating and Viscoelastic Behavior of Two Closely Related Monoclonal Antibodies" Pharmaceutical Research 28:1750-1764 (Apr. 6, 2011).
Burvenich et al., "Homology modeling based site-directed mutagenesis of anti-Le$^y$antibody hu3S193 Fc:FcRn interactions", Abstract #1240, AACR Annual Meeting, Denver, CO (Apr. 18-22, 2009), in 1 page.
Sinapis et al., "Pharmacokinetics of Intravitreal Bevacizumab (Avastin) in Rabbits", Investigative Ophthalmology & Visual Science, 51:2440 (Apr. 2010), Abstract only (in 2 pages).

\* cited by examiner

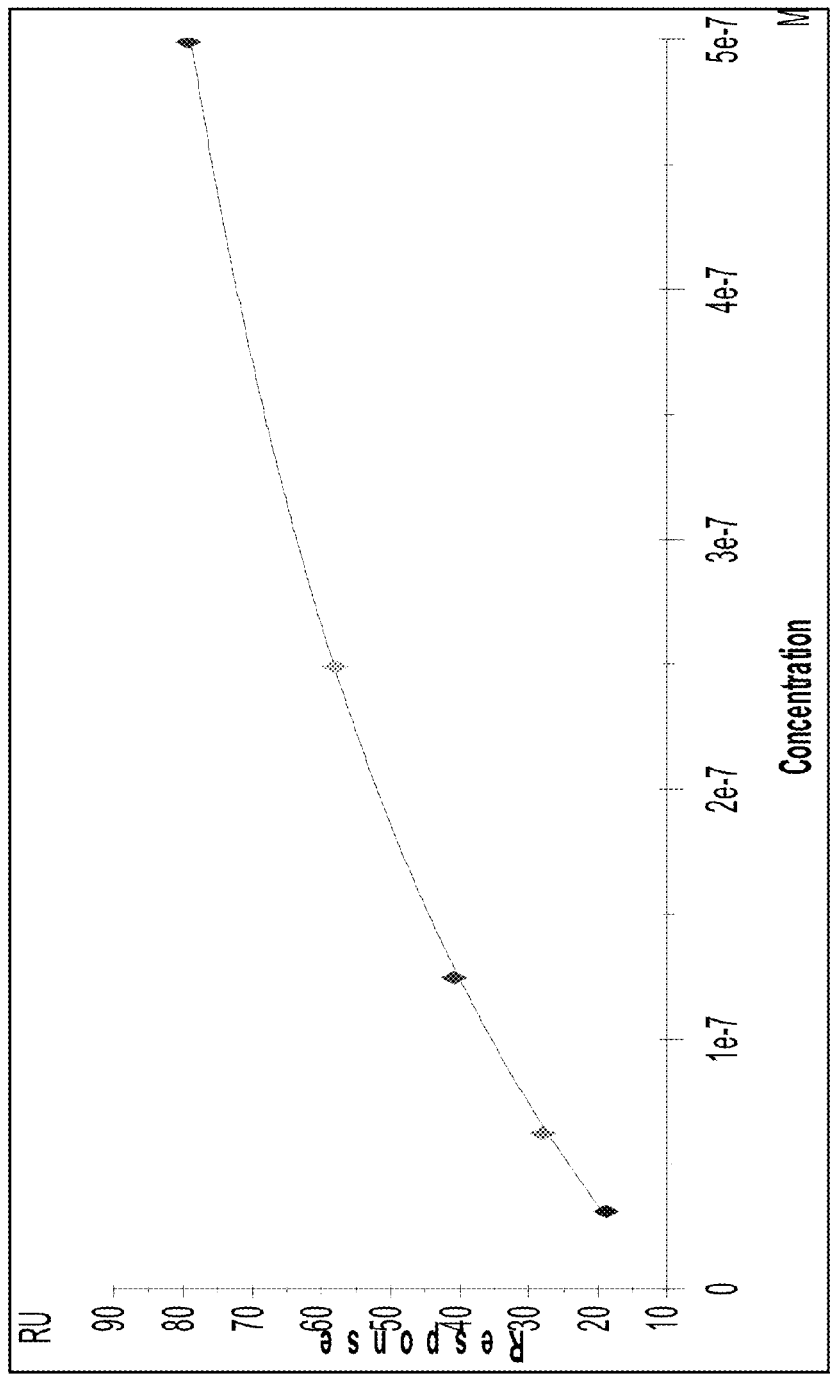

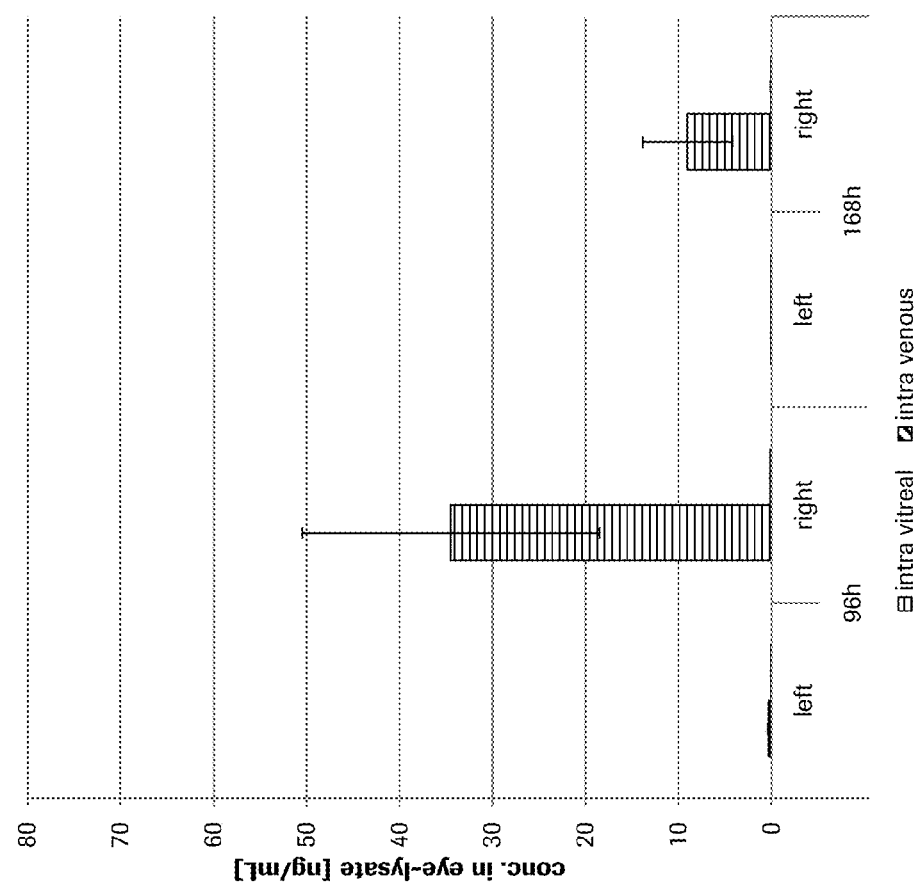

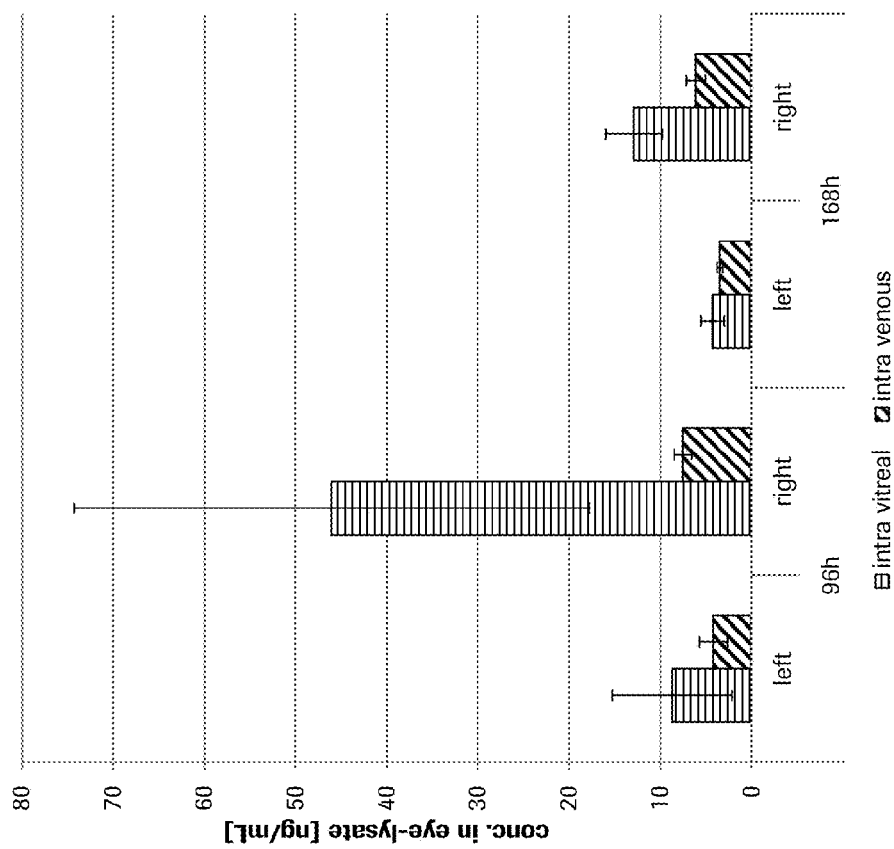

SEQUENCE LISTING

```
<160> NUMBER OF SEQ ID NOS: 50

<210> SEQ ID NO 1
<211> LENGTH: 14
<212> TYPE: PRT
<213> ORGANISM: Artificial
<220> FEATURE:
<223> OTHER INFORMATION: heavy chain CDR3H, <VEGF>ranibizumab

<400> SEQUENCE: 1

Tyr Pro Tyr Tyr Tyr Gly Thr Ser His Trp Tyr Phe Asp Val
1               5                   10

<210> SEQ ID NO 2
<211> LENGTH: 17
<212> TYPE: PRT
<213> ORGANISM: Artificial
<220> FEATURE:
<223> OTHER INFORMATION: heavy chain CDR2H, <VEGF>ranibizumab

<400> SEQUENCE: 2

Trp Ile Asn Thr Tyr Thr Gly Glu Pro Thr Tyr Ala Ala Asp Phe Lys
1               5                   10                  15

Arg

<210> SEQ ID NO 3
<211> LENGTH: 5
<212> TYPE: PRT
<213> ORGANISM: Artificial
<220> FEATURE:
<223> OTHER INFORMATION: heavy chain CDR1H, <VEGF>ranibizumab

<400> SEQUENCE: 3

His Tyr Gly Met Asn
1               5

<210> SEQ ID NO 4
<211> LENGTH: 9
<212> TYPE: PRT
<213> ORGANISM: Artificial
<220> FEATURE:
<223> OTHER INFORMATION: light chain CDR3L, <VEGF>ranibizumab

<400> SEQUENCE: 4

Gln Gln Tyr Ser Thr Val Pro Trp Thr
1               5

<210> SEQ ID NO 5
<211> LENGTH: 7
<212> TYPE: PRT
<213> ORGANISM: Artificial
```

```
<220> FEATURE:
<223> OTHER INFORMATION: light chain CDR2L, <VEGF>ranibizumab

<400> SEQUENCE: 5

Phe Thr Ser Ser Leu His Ser
1               5

<210> SEQ ID NO 6
<211> LENGTH: 11
<212> TYPE: PRT
<213> ORGANISM: Artificial
<220> FEATURE:
<223> OTHER INFORMATION: light chain CDR1L, <VEGF>ranibizumab

<400> SEQUENCE: 6

Ser Ala Ser Gln Asp Ile Ser Asn Tyr Leu Asn
1               5                   10

<210> SEQ ID NO 7
<211> LENGTH: 123
<212> TYPE: PRT
<213> ORGANISM: Artificial
<220> FEATURE:
<223> OTHER INFORMATION: heavy chain variable domain VH,
      <VEGF>ranibizumab

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser
        115                 120

<210> SEQ ID NO 8
<211> LENGTH: 107
<212> TYPE: PRT
<213> ORGANISM: Artificial
<220> FEATURE:
<223> OTHER INFORMATION: light chain variable domain VL,
      <VEGF>ranibizumab

<400> SEQUENCE: 8

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys
            100                 105

<210> SEQ ID NO 9
<211> LENGTH: 20
<212> TYPE: PRT
<213> ORGANISM: Artificial
<220> FEATURE:
<223> OTHER INFORMATION: heavy chain CDR3H, <ANG-2> Ang2i_LC10 variant

<400> SEQUENCE: 9

Ser Pro Asn Pro Tyr Tyr Tyr Asp Ser Ser Gly Tyr Tyr Tyr Pro Gly
 1               5                  10                  15

Ala Phe Asp Ile
            20

<210> SEQ ID NO 10
<211> LENGTH: 17
<212> TYPE: PRT
<213> ORGANISM: Artificial
<220> FEATURE:
<223> OTHER INFORMATION: heavy chain CDR2H, <ANG-2> Ang2i_LC10 variant

<400> SEQUENCE: 10

Trp Ile Asn Pro Asn Ser Gly Gly Thr Asn Tyr Ala Gln Lys Phe Gln
 1               5                  10                  15

Gly

<210> SEQ ID NO 11
<211> LENGTH: 5
<212> TYPE: PRT
<213> ORGANISM: Artificial
<220> FEATURE:
<223> OTHER INFORMATION: heavy chain CDR1H, <ANG-2> Ang2i_LC10 variant

<400> SEQUENCE: 11

Gly Tyr Tyr Met His
 1               5

<210> SEQ ID NO 12
<211> LENGTH: 11
<212> TYPE: PRT
<213> ORGANISM: Artificial
<220> FEATURE:
<223> OTHER INFORMATION: light chain CDR3L, <ANG-2> Ang2i_LC10 variant

<400> SEQUENCE: 12

Gln Val Trp Asp Ser Ser Ser Asp His Trp Val
 1               5                  10

<210> SEQ ID NO 13
<211> LENGTH: 7
<212> TYPE: PRT
<213> ORGANISM: Artificial
<220> FEATURE:
<223> OTHER INFORMATION: light chain CDR2L, <ANG-2> Ang2i_LC10 variant

<400> SEQUENCE: 13

Asp Asp Ser Asp Arg Pro Ser
 1               5
```

<210> SEQ ID NO 14
<211> LENGTH: 11
<212> TYPE: PRT
<213> ORGANISM: Artificial
<220> FEATURE:
<223> OTHER INFORMATION: light chain CDR1L, <ANG-2> Ang2i_LC10 variant

<400> SEQUENCE: 14

Gly Gly Asn Asn Ile Gly Ser Lys Ser Val His
1               5                   10

<210> SEQ ID NO 15
<211> LENGTH: 129
<212> TYPE: PRT
<213> ORGANISM: Artificial
<220> FEATURE:
<223> OTHER INFORMATION: heavy chain variable domain VH, <ANG-2>
      Ang2i_LC10 variant

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser

<210> SEQ ID NO 16
<211> LENGTH: 110
<212> TYPE: PRT
<213> ORGANISM: Artificial
<220> FEATURE:
<223> OTHER INFORMATION: light chain variable domain VL, <ANG-2>
      Ang2i_LC10 variant

<400> SEQUENCE: 16

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Thr Lys Leu Thr Val Leu Gly Gln
            100                 105                 110

<210> SEQ ID NO 17
<211> LENGTH: 191
<212> TYPE: PRT
<213> ORGANISM: Homo sapiens

<400> SEQUENCE: 17

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

<210> SEQ ID NO 18
<211> LENGTH: 496
<212> TYPE: PRT
<213> ORGANISM: Homo sapiens

<400> SEQUENCE: 18

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
210                 215                 220

Ser Ile Ile Glu Glu Leu Glu Lys Lys Ile Val Thr Ala Thr Val Asn
225                 230                 235                 240

Asn Ser Val Leu Gln Lys Gln His Asp Leu Met Glu Thr Val Asn
            245                 250                 255

Asn Leu Leu Thr Met Met Ser Thr Ser Asn Ser Ala Lys Asp Pro Thr
                260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Glu Gly Asn Glu Ala Tyr
370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 19
<211> LENGTH: 498
<212> TYPE: PRT
<213> ORGANISM: Homo sapiens

<400> SEQUENCE: 19

Met Thr Val Phe Leu Ser Phe Ala Phe Leu Ala Ala Ile Leu Thr His
1               5                   10                  15

```
Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45

Glu His Asp Gly Asn Cys Arg Glu Ser Thr Thr Asp Gln Tyr Asn Thr
50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
            260                 265                 270

Lys Gly Gly Lys Arg Glu Glu Lys Pro Phe Arg Asp Cys Ala Asp
        275                 280                 285

Val Tyr Gln Ala Gly Phe Asn Lys Ser Gly Ile Tyr Thr Ile Tyr Ile
    290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
        355                 360                 365

Arg Gln Tyr Met Leu Arg Ile Glu Leu Met Asp Trp Glu Gly Asn Arg
    370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
            420                 425                 430
```

```
Asp Asn Cys Met Cys Lys Cys Ala Leu Met Leu Thr Gly Gly Trp Trp
            435                 440                 445
Phe Asp Ala Cys Gly Pro Ser Asn Leu Asn Gly Met Phe Tyr Thr Ala
450                 455                 460
Gly Gln Asn His Gly Lys Leu Asn Gly Ile Lys Trp His Tyr Phe Lys
465                 470                 475                 480
Gly Pro Ser Tyr Ser Leu Arg Ser Thr Thr Met Met Ile Arg Pro Leu
                485                 490                 495
Asp Phe

<210> SEQ ID NO 20
<211> LENGTH: 1124
<212> TYPE: PRT
<213> ORGANISM: Homo sapiens

<400> SEQUENCE: 20

Met Asp Ser Leu Ala Ser Leu Val Leu Cys Gly Val Ser Leu Leu Leu
1               5                   10                  15
Ser Gly Thr Val Glu Gly Ala Met Asp Leu Ile Leu Ile Asn Ser Leu
                20                  25                  30
Pro Leu Val Ser Asp Ala Glu Thr Ser Leu Thr Cys Ile Ala Ser Gly
            35                  40                  45
Trp Arg Pro His Glu Pro Ile Thr Ile Gly Arg Asp Phe Glu Ala Leu
50                  55                  60
Met Asn Gln His Gln Asp Pro Leu Glu Val Thr Gln Asp Val Thr Arg
65                  70                  75                  80
Glu Trp Ala Lys Lys Val Val Trp Lys Arg Gly Lys Ala Ser Lys Ile
                85                  90                  95
Asn Gly Ala Tyr Phe Cys Glu Gly Arg Val Arg Gly Glu Ala Ile Arg
            100                 105                 110
Ile Arg Thr Met Lys Met Arg Gln Gln Ala Ser Phe Leu Pro Ala Thr
        115                 120                 125
Leu Thr Met Thr Val Asp Lys Gly Asp Asn Val Asn Ile Ser Phe Lys
130                 135                 140
Lys Val Leu Ile Lys Glu Glu Asp Ala Val Ile Tyr Lys Asn Gly Ser
145                 150                 155                 160
Phe Ile His Ser Val Pro Arg His Glu Val Pro Asp Ile Leu Glu Val
                165                 170                 175
His Leu Pro His Ala Gln Pro Gln Asp Ala Gly Val Tyr Ser Ala Arg
            180                 185                 190
Tyr Ile Gly Gly Asn Leu Phe Thr Ser Ala Phe Thr Arg Leu Ile Val
        195                 200                 205
Arg Arg Cys Glu Ala Gln Lys Trp Gly Pro Glu Cys Asn His Leu Cys
210                 215                 220
Thr Ala Cys Met Asn Asn Gly Val Cys His Glu Asp Thr Gly Glu Cys
225                 230                 235                 240
Ile Cys Pro Pro Gly Phe Met Gly Arg Thr Cys Glu Lys Ala Cys Glu
                245                 250                 255
Leu His Thr Phe Gly Arg Thr Cys Lys Glu Arg Cys Ser Gly Gln Glu
            260                 265                 270
Gly Cys Lys Ser Tyr Val Phe Cys Leu Pro Asp Pro Tyr Gly Cys Ser
        275                 280                 285
Cys Ala Thr Gly Trp Lys Gly Leu Gln Cys Asn Glu Ala Cys His Pro
290                 295                 300
```

```
Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
            325                 330                 335

Gly Leu Gln Cys Glu Arg Glu Gly Ile Pro Arg Met Thr Pro Lys Ile
        340                 345                 350

Val Asp Leu Pro Asp His Ile Glu Val Asn Ser Gly Lys Phe Asn Pro
    355                 360                 365

Ile Cys Lys Ala Ser Gly Trp Pro Leu Pro Thr Asn Glu Glu Met Thr
370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
        435                 440                 445

Asn Ala Pro Asn Val Ile Asp Thr Gly His Asn Phe Ala Val Ile Asn
450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
            500                 505                 510

Tyr Glu Leu Cys Val Gln Leu Val Arg Arg Gly Glu Gly Gly Glu Gly
        515                 520                 525

His Pro Gly Pro Val Arg Arg Phe Thr Thr Ala Ser Ile Gly Leu Pro
    530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Gln Asn Ile Lys
            580                 585                 590

Val Pro Gly Asn Leu Thr Ser Val Leu Leu Asn Asn Leu His Pro Arg
        595                 600                 605

Glu Gln Tyr Val Val Arg Ala Arg Val Asn Thr Lys Ala Gln Gly Glu
    610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
                645                 650                 655

Ile Ser Trp Thr Ile Leu Asp Gly Tyr Ser Ile Ser Ile Thr Ile
            660                 665                 670

Arg Tyr Lys Val Gln Gly Lys Asn Glu Asp Gln His Val Asp Val Lys
        675                 680                 685

Ile Lys Asn Ala Thr Ile Thr Gln Tyr Gln Leu Lys Gly Leu Glu Pro
    690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
```

```
                          725                 730                 735
Ala Pro Ala Asp Leu Gly Gly Gly Lys Met Leu Leu Ile Ala Ile Leu
            740                 745                 750

Gly Ser Ala Gly Met Thr Cys Leu Thr Val Leu Leu Ala Phe Leu Ile
            755                 760                 765

Ile Leu Gln Leu Lys Arg Ala Asn Val Gln Arg Arg Met Ala Gln Ala
            770                 775                 780

Phe Gln Asn Val Arg Glu Glu Pro Ala Val Gln Phe Asn Ser Gly Thr
785                 790                 795                 800

Leu Ala Leu Asn Arg Lys Val Lys Asn Pro Asp Pro Thr Ile Tyr
                805                 810                 815

Pro Val Leu Asp Trp Asn Asp Ile Lys Phe Gln Asp Val Ile Gly Glu
                820                 825                 830

Gly Asn Phe Gly Gln Val Leu Lys Ala Arg Ile Lys Lys Asp Gly Leu
                835                 840                 845

Arg Met Asp Ala Ala Ile Lys Arg Met Lys Glu Tyr Ala Ser Lys Asp
850                 855                 860

Asp His Arg Asp Phe Ala Gly Glu Leu Glu Val Leu Cys Lys Leu Gly
865                 870                 875                 880

His His Pro Asn Ile Ile Asn Leu Leu Gly Ala Cys Glu His Arg Gly
                885                 890                 895

Tyr Leu Tyr Leu Ala Ile Glu Tyr Ala Pro His Gly Asn Leu Leu Asp
                900                 905                 910

Phe Leu Arg Lys Ser Arg Val Leu Glu Thr Asp Pro Ala Phe Ala Ile
                915                 920                 925

Ala Asn Ser Thr Ala Ser Thr Leu Ser Ser Gln Gln Leu Leu His Phe
                930                 935                 940

Ala Ala Asp Val Ala Arg Gly Met Asp Tyr Leu Ser Gln Lys Gln Phe
945                 950                 955                 960

Ile His Arg Asp Leu Ala Ala Arg Asn Ile Leu Val Gly Glu Asn Tyr
                965                 970                 975

Val Ala Lys Ile Ala Asp Phe Gly Leu Ser Arg Gly Gln Glu Val Tyr
                980                 985                 990

Val Lys Lys Thr Met Gly Arg Leu Pro Val Arg Trp Met Ala Ile Glu
                995                 1000                1005

Ser Leu Asn Tyr Ser Val Tyr Thr Thr Asn Ser Asp Val Trp Ser
                1010                1015                1020

Tyr Gly Val Leu Leu Trp Glu Ile Val Ser Leu Gly Gly Thr Pro
                1025                1030                1035

Tyr Cys Gly Met Thr Cys Ala Glu Leu Tyr Glu Lys Leu Pro Gln
                1040                1045                1050

Gly Tyr Arg Leu Glu Lys Pro Leu Asn Cys Asp Asp Glu Val Tyr
                1055                1060                1065

Asp Leu Met Arg Gln Cys Trp Arg Glu Lys Pro Tyr Glu Arg Pro
                1070                1075                1080

Ser Phe Ala Gln Ile Leu Val Ser Leu Asn Arg Met Leu Glu Glu
                1085                1090                1095

Arg Lys Thr Tyr Val Asn Thr Thr Leu Tyr Glu Lys Phe Thr Tyr
                1100                1105                1110

Ala Gly Ile Asp Cys Ser Ala Glu Glu Ala Ala
                1115                1120

<210> SEQ ID NO 21
```

<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1
      with AAA mutations(VEGFang2-0012)

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Lys Pro Lys Asp Thr
                245                 250                 255

Leu Met Ala Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu Ala Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
        355                 360                 365

Val Ser Leu Trp Cys Leu Val Lys Gly Phe Tyr Pro Ser Asp Ile Ala
```

```
            370                 375                 380
Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn Ala Tyr Thr Gln Lys Ser Leu Ser
                435                 440                 445

Leu Ser Pro Gly Lys
            450

<210> SEQ ID NO 22
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      with AAA mutations (VEGFang2-0012)

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
                100                 105                 110

Pro Gly Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ala Ser Arg Thr
            260                 265                 270
```

```
Pro Glu Val Thr Cys Val Val Asp Val Ser His Glu Asp Pro Glu
            275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Cys Thr Leu Pro
    355                 360                 365

Pro Ser Arg Asp Glu Leu Thr Lys Asn Gln Val Ser Leu Ser Cys Ala
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
    435                 440                 445

His Asn Ala Tyr Thr Gln Lys Ser Leu Ser Leu Ser Pro Gly Lys
        450                 455                 460

<210> SEQ ID NO 23
<211> LENGTH: 214
<212> TYPE: PRT
<213> ORGANISM: Artificial
<220> FEATURE:
<223> OTHER INFORMATION: Light chain 1 of <VEGF-ANG-2> CrossMAb IgG1
      with AAA mutations (VEGFang2-0012)

<400> SEQUENCE: 23

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 24
<211> LENGTH: 213
<212> TYPE: PRT
<213> ORGANISM: Artificial
<220> FEATURE:
<223> OTHER INFORMATION: Light chain 2 of <VEGF-ANG-2> CrossMAb IgG1
      with AAA mutations (VEGF-Ang2-0012)

<400> SEQUENCE: 24

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210
```

<210> SEQ ID NO 25
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1
      with AAA mutations and P329G LALA mutations (VEGFang2-0016)

<400> SEQUENCE: 25

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30
```

-continued

```
Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ala Ser Arg Thr Pro Glu Val Thr Cys Val Val Val Asp Val
            260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu Ala Gln Asp Trp Leu
305                 310                 315                 320

Asn Gly Lys Glu Tyr Lys Cys Lys Val Ser Asn Lys Ala Leu Gly Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
            355                 360                 365

Val Ser Leu Trp Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn Ala Tyr Thr Gln Lys Ser Leu Ser
            435                 440                 445
```

-continued

Leu Ser Pro Gly Lys
    450

<210> SEQ ID NO 26
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      with AAA mutations and P329G LALA mutations (VEGFang2-0016)

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ala Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
                325                 330                 335

Cys Lys Val Ser Asn Lys Ala Leu Gly Ala Pro Ile Glu Lys Thr Ile
            340                 345                 350

Ser Lys Ala Lys Gly Gln Pro Arg Glu Pro Gln Val Cys Thr Leu Pro
355                 360                 365

Pro Ser Arg Asp Glu Leu Thr Lys Asn Gln Val Ser Leu Ser Cys Ala
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
                435                 440                 445

His Asn Ala Tyr Thr Gln Lys Ser Leu Ser Leu Ser Pro Gly Lys
        450                 455                 460

<210> SEQ ID NO 27
<211> LENGTH: 214
<212> TYPE: PRT
<213> ORGANISM: Artificial
<220> FEATURE:
<223> OTHER INFORMATION: Light chain 1 of  <VEGF-ANG-2> CrossMAb IgG1
      with AAA mutations and P329G LALA mutations (VEGFang2-0016)

<400> SEQUENCE: 27

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 28
<211> LENGTH: 213
<212> TYPE: PRT

<213> ORGANISM: Artificial
<220> FEATURE:
<223> OTHER INFORMATION: Light chain 2 of <VEGF-ANG-2> CrossMAb IgG1
      with AAA mutations and P329G LALA mutations (VEGFang2-0016)

<400> SEQUENCE: 28

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Trp Val Phe Gly Gly Gly Thr Lys Leu Thr Val Leu Ser Ser Ala Ser
                100                 105                 110

Thr Lys Gly Pro Ser Val Phe Pro Leu Ala Pro Ser Ser Lys Ser Thr
            115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210

<210> SEQ ID NO 29
<211> LENGTH: 450
<212> TYPE: PRT
<213> ORGANISM: Artificial
<220> FEATURE:
<223> OTHER INFORMATION: Heavy chain 1 of <VEGF-ANG-2> CrossMAb IgG4
      with AAA mutations and with SPLE mutations

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val

```
            100                 105                 110
Trp Gly Gln Gly Thr Leu Val Thr Val Ser Ser Ala Ser Thr Lys Gly
            115                 120                 125
Pro Ser Val Phe Pro Leu Ala Pro Cys Ser Arg Ser Thr Ser Glu Ser
        130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Lys Thr Tyr Thr Cys Asn Val
        195                 200                 205
Asp His Lys Pro Ser Asn Thr Lys Val Asp Lys Arg Val Glu Ser Lys
    210                 215                 220
Tyr Gly Pro Pro Cys Pro Pro Cys Pro Ala Pro Glu Phe Glu Gly Gly
225                 230                 235                 240
Pro Ser Val Phe Leu Phe Pro Pro Lys Pro Lys Asp Thr Leu Met Ala
                245                 250                 255
Ser Arg Thr Pro Glu Val Thr Cys Val Val Val Asp Val Ser Gln Glu
            260                 265                 270
Asp Pro Glu Val Gln Phe Asn Trp Tyr Val Asp Gly Val Glu Val His
        275                 280                 285
Asn Ala Lys Thr Lys Pro Arg Glu Glu Gln Phe Asn Ser Thr Tyr Arg
    290                 295                 300
Val Val Ser Val Leu Thr Val Leu Ala Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Cys
            340                 345                 350
Thr Leu Pro Pro Ser Gln Glu Glu Met Thr Lys Asn Gln Val Ser Leu
        355                 360                 365
Ser Cys Ala Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Val Ser Arg Leu Thr Val Asp
                405                 410                 415
Lys Ser Arg Trp Gln Glu Gly Asn Val Phe Ser Cys Ser Val Met His
            420                 425                 430
Glu Ala Leu His Asn Ala Tyr Thr Gln Lys Ser Leu Ser Leu Ser Leu
        435                 440                 445
Gly Lys
    450

<210> SEQ ID NO 30
<211> LENGTH: 460
<212> TYPE: PRT
<213> ORGANISM: Artificial
<220> FEATURE:
<223> OTHER INFORMATION: Heavy chain 2 of <VEGF-ANG-2> CrossMAb IgG4
      with AAA mutations and with SPLE mutations

<400> SEQUENCE: 30
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Ser Gly Tyr Tyr Tyr
            100                 105                 110

Pro Gly Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Pro Pro Cys Pro
225                 230                 235                 240

Pro Cys Pro Ala Pro Glu Phe Glu Gly Gly Pro Ser Val Phe Leu Phe
                245                 250                 255

Pro Pro Lys Pro Lys Asp Thr Leu Met Ala Ser Arg Thr Pro Glu Val
            260                 265                 270

Thr Cys Val Val Val Asp Val Ser Gln Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Tyr Arg Val Val Ser Val Leu Thr
305                 310                 315                 320

Val Leu Ala Gln Asp Trp Leu Asn Gly Lys Glu Tyr Lys Cys Lys Val
                325                 330                 335

Ser Asn Lys Gly Leu Pro Ser Ser Ile Glu Lys Thr Ile Ser Lys Ala
            340                 345                 350

Lys Gly Gln Pro Arg Glu Pro Gln Val Tyr Thr Leu Pro Pro Cys Gln
        355                 360                 365

Glu Glu Met Thr Lys Asn Gln Val Ser Leu Trp Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Arg Leu Thr Val Asp Lys Ser Arg Trp Gln Glu

```
                420             425             430
Gly Asn Val Phe Ser Cys Ser Val Met His Glu Ala Leu His Asn Ala
            435             440             445

Tyr Thr Gln Lys Ser Leu Ser Leu Ser Leu Gly Lys
        450             455             460

<210> SEQ ID NO 31
<211> LENGTH: 214
<212> TYPE: PRT
<213> ORGANISM: Artificial
<220> FEATURE:
<223> OTHER INFORMATION: Light chain 1 of <VEGF-ANG-2> CrossMAb IgG4
      with AAA mutations and with SPLE mutations

<400> SEQUENCE: 31

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 32
<211> LENGTH: 213
<212> TYPE: PRT
<213> ORGANISM: Artificial
<220> FEATURE:
<223> OTHER INFORMATION: Light chain 2 of <VEGF-ANG-2> CrossMAb IgG4
      with AAA mutations and with SPLE mutations

<400> SEQUENCE: 32

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
```

```
                35                  40                  45
Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Trp Val Phe Gly Gly Gly Thr Lys Leu Thr Val Leu Ser Ser Ala Ser
                100                 105                 110

Thr Lys Gly Pro Ser Val Phe Pro Leu Ala Pro Cys Ser Arg Ser Thr
            115                 120                 125

Ser Glu Ser Thr Ala Ala Leu Gly Cys Leu Val Lys Asp Tyr Phe Pro
130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Lys Thr Tyr Thr
                180                 185                 190

Cys Asn Val Asp His Lys Pro Ser Asn Thr Lys Val Asp Lys Arg Val
                195                 200                 205

Glu Ser Lys Tyr Gly
            210

<210> SEQ ID NO 33
<211> LENGTH: 453
<212> TYPE: PRT
<213> ORGANISM: Artificial
<220> FEATURE:
<223> OTHER INFORMATION: Heavy chain 1 of <VEGF-ANG-2> OAscFab IgG1
      with AAA mutations

<400> SEQUENCE: 33

Glu Val Gln Leu Val Glu Ser Gly Gly Gly Leu Val Gln Pro Gly Gly
1               5                  10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro Tyr Tyr Gly Thr Ser His Trp Tyr Phe Asp Val
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ala Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu Ala Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn Ala Tyr Thr Gln Lys Ser Leu Ser
        435                 440                 445

Leu Ser Pro Gly Lys
    450

<210> SEQ ID NO 34
<211> LENGTH: 705
<212> TYPE: PRT
<213> ORGANISM: Artificial
<220> FEATURE:
<223> OTHER INFORMATION: Heavy chain 2 of <VEGF-ANG-2> OAscFab IgG1
      with AAA mutations

<400> SEQUENCE: 34

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80
```

```
Asp Glu Ala Asp Tyr Tyr Cys Gln Val Trp Asp Ser Ser Asp His
                85                  90                  95

Trp Val Phe Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Gly Gly Gly Ser Gly Gly Gly Ser
    210                 215                 220

Gly Gly Gly Gly Ser Gly Gly Gly Ser Gly Gly Gly Ser Gly
225                 230                 235                 240

Gly Gly Ser Gly Gly Gln Val Gln Leu Val Glu Ser Gly Ala Glu
            245                 250                 255

Val Lys Lys Pro Gly Ala Ser Val Lys Val Ser Cys Lys Ala Ser Gly
                260                 265                 270

Tyr Thr Phe Thr Gly Tyr Tyr Met His Trp Val Arg Gln Ala Pro Gly
            275                 280                 285

Gln Gly Leu Glu Trp Met Gly Trp Ile Asn Pro Asn Ser Gly Gly Thr
    290                 295                 300

Asn Tyr Ala Gln Lys Phe Gln Gly Arg Val Thr Met Thr Arg Asp Thr
305                 310                 315                 320

Ser Ile Ser Thr Ala Tyr Met Glu Leu Ser Arg Leu Arg Ser Asp Asp
                325                 330                 335

Thr Ala Val Tyr Tyr Cys Ala Arg Ser Pro Asn Pro Tyr Tyr Tyr Asp
            340                 345                 350

Ser Ser Gly Tyr Tyr Tyr Pro Gly Ala Phe Asp Ile Trp Gly Gln Gly
        355                 360                 365

Thr Met Val Thr Val Ser Ser Ala Ser Thr Lys Gly Pro Ser Val Phe
370                 375                 380

Pro Leu Ala Pro Ser Ser Lys Ser Thr Ser Gly Gly Thr Ala Ala Leu
385                 390                 395                 400

Gly Cys Leu Val Lys Asp Tyr Phe Pro Glu Pro Val Thr Val Ser Trp
            405                 410                 415

Asn Ser Gly Ala Leu Thr Ser Gly Val His Thr Phe Pro Ala Val Leu
        420                 425                 430

Gln Ser Ser Gly Leu Tyr Ser Leu Ser Ser Val Val Thr Val Pro Ser
    435                 440                 445

Ser Ser Leu Gly Thr Gln Thr Tyr Ile Cys Asn Val Asn His Lys Pro
450                 455                 460

Ser Asn Thr Lys Val Asp Lys Lys Val Glu Pro Lys Ser Cys Asp Lys
465                 470                 475                 480

Thr His Thr Cys Pro Pro Cys Pro Ala Pro Glu Leu Leu Gly Gly Pro
                485                 490                 495
```

```
Ser Val Phe Leu Phe Pro Pro Lys Pro Lys Asp Thr Leu Met Ala Ser
            500                 505                 510

Arg Thr Pro Glu Val Thr Cys Val Val Val Asp Val Ser His Glu Asp
        515                 520                 525

Pro Glu Val Lys Phe Asn Trp Tyr Val Asp Gly Val Glu Val His Asn
    530                 535                 540

Ala Lys Thr Lys Pro Arg Glu Glu Gln Tyr Asn Ser Thr Tyr Arg Val
545                 550                 555                 560

Val Ser Val Leu Thr Val Leu Ala Gln Asp Trp Leu Asn Gly Lys Glu
                565                 570                 575

Tyr Lys Cys Lys Val Ser Asn Lys Ala Leu Pro Ala Pro Ile Glu Lys
            580                 585                 590

Thr Ile Ser Lys Ala Lys Gly Gln Pro Arg Glu Pro Gln Val Tyr Thr
        595                 600                 605

Leu Pro Pro Cys Arg Asp Glu Leu Thr Lys Asn Gln Val Ser Leu Trp
    610                 615                 620

Cys Leu Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
                645                 650                 655

Asp Ser Asp Gly Ser Phe Phe Leu Tyr Ser Lys Leu Thr Val Asp Lys
            660                 665                 670

Ser Arg Trp Gln Gln Gly Asn Val Phe Ser Cys Ser Val Met His Glu
        675                 680                 685

Ala Leu His Asn Ala Tyr Thr Gln Lys Ser Leu Ser Leu Ser Pro Gly
    690                 695                 700

Lys
705

<210> SEQ ID NO 35
<211> LENGTH: 214
<212> TYPE: PRT
<213> ORGANISM: Artificial
<220> FEATURE:
<223> OTHER INFORMATION: Light chain 1 of <VEGF-ANG-2> OAscFab IgG1 with
      AAA mutations

<400> SEQUENCE: 35

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 36
<211> LENGTH: 450
<212> TYPE: PRT
<213> ORGANISM: Artificial
<220> FEATURE:
<223> OTHER INFORMATION: Heavy chain 1 of <VEGF-ANG-2> OAscFab IgG4 with
      AAA mutations and with SPLE mutations

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
            85                  90                  95

Ala Lys Tyr Pro Tyr Tyr Tyr Gly Thr Ser His Trp Tyr Phe Asp Val
        100                 105                 110

Trp Gly Gln Gly Thr Leu Val Thr Val Ser Ser Ala Ser Thr Lys Gly
    115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ala
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His

```
                    275                 280                 285
Asn Ala Lys Thr Lys Pro Arg Glu Glu Gln Phe Asn Ser Thr Tyr Arg
    290                 295                 300

Val Val Ser Val Leu Thr Val Leu Ala Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Cys
            340                 345                 350

Thr Leu Pro Pro Ser Gln Glu Glu Met Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn Ala Tyr Thr Gln Lys Ser Leu Ser Leu Ser Leu
        435                 440                 445

Gly Lys
    450

<210> SEQ ID NO 37
<211> LENGTH: 702
<212> TYPE: PRT
<213> ORGANISM: Artificial
<220> FEATURE:
<223> OTHER INFORMATION: Heavy chain 2 of <VEGF-ANG-2> OAscFab IgG4 with
      AAA mutations and with SPLE mutations

<400> SEQUENCE: 37

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175
```

```
Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Gly Gly Gly Ser Gly Gly Gly Gly Ser
    210                 215                 220

Gly Gly Gly Gly Ser Gly Gly Gly Ser Gly Gly Gly Ser Gly
225                 230                 235                 240

Gly Gly Gly Ser Gly Gly Gln Val Gln Leu Val Glu Ser Gly Ala Glu
                245                 250                 255

Val Lys Lys Pro Gly Ala Ser Val Lys Val Ser Cys Lys Ala Ser Gly
        260                 265                 270

Tyr Thr Phe Thr Gly Tyr Tyr Met His Trp Val Arg Gln Ala Pro Gly
        275                 280                 285

Gln Gly Leu Glu Trp Met Gly Trp Ile Asn Pro Asn Ser Gly Gly Thr
        290                 295                 300

Asn Tyr Ala Gln Lys Phe Gln Gly Arg Val Thr Met Thr Arg Asp Thr
305                 310                 315                 320

Ser Ile Ser Thr Ala Tyr Met Glu Leu Ser Arg Leu Arg Ser Asp Asp
                325                 330                 335

Thr Ala Val Tyr Tyr Cys Ala Arg Ser Pro Asn Pro Tyr Tyr Tyr Asp
                340                 345                 350

Ser Ser Gly Tyr Tyr Pro Gly Ala Phe Asp Ile Trp Gly Gln Gly
                355                 360                 365

Thr Met Val Thr Val Ser Ser Ala Ser Thr Lys Gly Pro Ser Val Phe
    370                 375                 380

Pro Leu Ala Pro Cys Ser Arg Ser Thr Ser Glu Ser Thr Ala Ala Leu
385                 390                 395                 400

Gly Cys Leu Val Lys Asp Tyr Phe Pro Glu Pro Val Thr Val Ser Trp
                405                 410                 415

Asn Ser Gly Ala Leu Thr Ser Gly Val His Thr Phe Pro Ala Val Leu
                420                 425                 430

Gln Ser Ser Gly Leu Tyr Ser Leu Ser Ser Val Val Thr Val Pro Ser
        435                 440                 445

Ser Ser Leu Gly Thr Lys Thr Tyr Thr Cys Asn Val Asp His Lys Pro
450                 455                 460

Ser Asn Thr Lys Val Asp Lys Arg Val Glu Ser Lys Tyr Gly Pro Pro
465                 470                 475                 480

Cys Pro Pro Cys Pro Ala Pro Glu Phe Glu Gly Gly Pro Ser Val Phe
                485                 490                 495

Leu Phe Pro Pro Lys Pro Lys Asp Thr Leu Met Ala Ser Arg Thr Pro
                500                 505                 510

Glu Val Thr Cys Val Val Val Asp Val Ser Gln Glu Asp Pro Glu Val
        515                 520                 525

Gln Phe Asn Trp Tyr Val Asp Gly Val Glu Val His Asn Ala Lys Thr
        530                 535                 540

Lys Pro Arg Glu Glu Gln Phe Asn Ser Thr Tyr Arg Val Val Ser Val
545                 550                 555                 560

Leu Thr Val Leu Ala Gln Asp Trp Leu Asn Gly Lys Glu Tyr Lys Cys
                565                 570                 575

Lys Val Ser Asn Lys Gly Leu Pro Ser Ser Ile Glu Lys Thr Ile Ser
                580                 585                 590

Lys Ala Lys Gly Gln Pro Arg Glu Pro Gln Val Tyr Thr Leu Pro Pro
```

595                 600                 605
Cys Gln Glu Glu Met Thr Lys Asn Gln Val Ser Leu Trp Cys Leu Val
    610                 615                 620

Lys Gly Phe Tyr Pro Ser Asp Ile Ala Val Glu Trp Glu Ser Asn Gly
625                 630                 635                 640

Gln Pro Glu Asn Asn Tyr Lys Thr Thr Pro Val Leu Asp Ser Asp
                    645                 650                 655

Gly Ser Phe Phe Leu Tyr Ser Arg Leu Thr Val Asp Lys Ser Arg Trp
                660                 665                 670

Gln Glu Gly Asn Val Phe Ser Cys Ser Val Met His Glu Ala Leu His
                675                 680                 685

Asn Ala Tyr Thr Gln Lys Ser Leu Ser Leu Ser Leu Gly Lys
690                 695                 700

<210> SEQ ID NO 38
<211> LENGTH: 214
<212> TYPE: PRT
<213> ORGANISM: Artificial
<220> FEATURE:
<223> OTHER INFORMATION: Light chain 1 of <VEGF-ANG-2> OAscFab IgG4 with
      AAA mutations and with SPLE mutations

<400> SEQUENCE: 38

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 39
<211> LENGTH: 453
<212> TYPE: PRT
<213> ORGANISM: Artificial
<220> FEATURE:

<223> OTHER INFORMATION: Heavy chain 1 of <VEGF-ANG-2> CrossMAb IgG1
wild type (without AAA mutations) (VEGFang2-0201)

<400> SEQUENCE: 39

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
        355                 360                 365

Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400
```

```
Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 40
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      wild type (without AAA mutations) (VEGFang2-0201)

<400> SEQUENCE: 40

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
```

```
                290                 295                 300
Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
                340                 345                 350

Ser Lys Ala Lys Gly Gln Pro Arg Glu Pro Gln Val Cys Thr Leu Pro
                355                 360                 365

Pro Ser Arg Asp Glu Leu Thr Lys Asn Gln Val Ser Leu Ser Cys Ala
        370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
                420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
        450                 455                 460

<210> SEQ ID NO 41
<211> LENGTH: 214
<212> TYPE: PRT
<213> ORGANISM: Artificial
<220> FEATURE:
<223> OTHER INFORMATION: Light chain 1 of <VEGF-ANG-2> CrossMAb IgG1
      wild type ( without AAA mutations) (VEGFang2-0201)

<400> SEQUENCE: 41

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
    210

<210> SEQ ID NO 42
<211> LENGTH: 213
<212> TYPE: PRT
<213> ORGANISM: Artificial
<220> FEATURE:
<223> OTHER INFORMATION: Light chain 2 of <VEGF-ANG-2> CrossMAb IgG1
      wild type (without AAA mutations) (VEGFang2-0201)

<400> SEQUENCE: 42

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210

<210> SEQ ID NO 43
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1
      with P329G LALA mutations only (without AAA mutations)
      (VEGFang2-0015)

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

-continued

```
Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Gly Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Cys Arg Asp Glu Leu Thr Lys Asn Gln
            355                 360                 365

Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
    450
```

<210> SEQ ID NO 44
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      with P329G LALA mutations only (without AAA mutations)
      (VEGFang2-0015)

<400> SEQUENCE: 44

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Gly Ala Pro Ile Glu Lys Thr Ile
            340                 345                 350

Ser Lys Ala Lys Gly Gln Pro Arg Glu Pro Gln Val Cys Thr Leu Pro
```

355                 360                 365
Pro Ser Arg Asp Glu Leu Thr Lys Asn Gln Val Ser Leu Ser Cys Ala
        370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
                420                 425                 430

Trp Gln Gln Gly Asn Val Phe Ser Cys Ser Val Met His Glu Ala Leu
                435                 440                 445

His Asn His Tyr Thr Gln Lys Ser Leu Ser Leu Ser Pro Gly Lys
                450                 455                 460

<210> SEQ ID NO 45
<211> LENGTH: 214
<212> TYPE: PRT
<213> ORGANISM: Artificial
<220> FEATURE:
<223> OTHER INFORMATION: Light chain 1 of <VEGF-ANG-2> CrossMAb IgG1
      with P329G LALA mutations only (without AAA mutations)
      (VEGFang2-0015)

<400> SEQUENCE: 45

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 46
<211> LENGTH: 213
<212> TYPE: PRT
<213> ORGANISM: Artificial

<220> FEATURE:
<223> OTHER INFORMATION: Light chain 2 of <VEGF-ANG-2> CrossMAb IgG1
      with P329G LALA mutations only (without AAA mutations)
      (VEGFang2-0015)

<400> SEQUENCE: 46

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210
```

<210> SEQ ID NO 47
<211> LENGTH: 107
<212> TYPE: PRT
<213> ORGANISM: Homo sapiens

<400> SEQUENCE: 47

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

-continued

```
<210> SEQ ID NO 48
<211> LENGTH: 105
<212> TYPE: PRT
<213> ORGANISM: homo sapiens

<400> SEQUENCE: 48

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 49
<211> LENGTH: 330
<212> TYPE: PRT
<213> ORGANISM: Homo sapiens

<400> SEQUENCE: 49

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
```

```
                225                 230                 235                 240
Leu Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                    260                 265                 270

Asn Tyr Lys Thr Thr Pro Pro Val Leu Asp Ser Asp Gly Ser Phe Phe
                    275                 280                 285

Leu Tyr Ser Lys Leu Thr Val Asp Lys Ser Arg Trp Gln Gln Gly Asn
                    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                    325                 330

<210> SEQ ID NO 50
<211> LENGTH: 327
<212> TYPE: PRT
<213> ORGANISM: Homo sapiens

<400> SEQUENCE: 50

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270
```

-continued

```
Thr Thr Pro Pro Val Leu Asp Ser Asp Gly Ser Phe Phe Leu Tyr Ser
        275             280             285

Arg Leu Thr Val Asp Lys Ser Arg Trp Gln Glu Gly Asn Val Phe Ser
    290             295             300

Cys Ser Val Met His Glu Ala Leu His Asn His Tyr Thr Gln Lys Ser
305             310             315             320

Leu Ser Leu Ser Leu Gly Lys
                325
```

BISPECIFIC ANTI-VEGF/ANTI-ANG-2 ANTIBODIES AND THEIR USE IN THE TREATMENT OF OCULAR VASCULAR DISEASES

CROSS REFERENCE TO RELATED APPLICATIONS

This application claims the benefit of priority under 35 USC 119(a) to European patent application number 12 176299.1, filed 13 Jul. 2012, the disclosure of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jul. 10, 2013, is named P4996_Sequence_listing.txt and is 120,465 bytes in size.

FIELD OF THE INVENTION

The present invention relates a method for the reduction of the viscosity of an antibody (including a bispecific antibody) of human IgG1 or human IgG4 subclass, to bispecific antibodies against human vascular endothelial growth factor (VEGF/VEGF-A) and against human angiopoietin-2 (ANG-2), methods for their production, pharmaceutical compositions containing said antibodies, and uses thereof.

BACKGROUND OF THE INVENTION

Angiogenesis is implicated in the pathogenesis of a variety of disorders which include solid tumors, intraocular neovascular syndromes such as proliferative retinopathies or age-related macular degeneration (AMD), rheumatoid arthritis, and psoriasis (Folkman, J., et al., J. Biol. Chem. 267 (1992) 10931-10934; Klagsbrun, M., et al., Annu Rev. Physiol. 53 (1991) 217-239; and Garner, A., Vascular diseases, in: Pathobiology of ocular disease, A dynamic approach, Garner, A., and Klintworth, G.K. (eds.), 2nd edition, Marcel Dekker, New York (1994), pp. 1625-1710).

Ranibizumab (trade name Lucentis®) is a monoclonal antibody fragment derived from the same parent murine antibody as bevacizumab (Avastin®). However, it has been affinity matured to provide stronger binding to VEGF-A (WO 98/45331). It is known that VEGF-A blocking may be related to some systemic toxicities, therefore ranibizumab is missing an Fc part to reduce the serum half live and consequently systemic toxicities. It is an anti-angiogenic agent that has been approved to treat the "wet" type of age-related macular degeneration (ARMD), a common form of age-related vision loss.

Corneal angiogenesis assays have shown that both ANG-1 and ANG-2 had similar effects, acting synergistically with VEGF to promote growth of new blood vessels. Asahara, T., et al., Circ. Res. 83 (1998) 233-40. The possibility that there was a dose-dependent endothelial response was raised by the observation that in vitro at high concentration, ANG-2 can also be pro-angiogenic (Kim, I., et al., Oncogene 19 (2000) 4549-52). At high concentration, ANG-2 acts as an apoptosis survival factor for endothelial cells during serum deprivation apoptosis through activation of Tie2 via PI-3 Kinase and Akt pathway (Kim, I., et al., Oncogene 19 (2000) 4549-52).

WO 2010/040508 A9 and WO 2011/117329 relate to bispecific anti-VEGF/anti-ANG-2 antibodies. WO 2008/132568 relates to fusion proteins binding to growth factors. WO 2009/136352 relates to anti-angiogenic compounds. WO 2009/080253 and WO 2011/117330 relates to bispecific bivalent antibody formats. WO 2010/069532 relates to Ang2 antibodies.

Ocular vascular diseases such as age related macular degeneration (ARMD) and diabetic retinopathy (DR) are due to abnormal choroidal or retinal neovascularization respectively. They are the leading causes of visual loss in industrialized nations. Since the retina consists of well-defined layers of neuronal, glial, and vascular elements, relatively small disturbances such as those seen in vascular proliferation or edema can lead to significant loss of visual function. Inherited retinal degenerations, such as Retinitis Pigmentosa (RP), are also associated with vascular abnormalities, such as arteriolar narrowing and vascular atrophy. They affect as many as 1 in 3500 individuals and are characterized by progressive night blindness, visual field loss, optic nerve atrophy, arteriolar attenuation, and central loss of vision often progressing to complete blindness.

Ischemic retinopathies are characterized by loss or dysfunction of the retinal vasculature which results in a reduction of blood flow and hypoxia. The retina responds to hypoxia by generating signals to grow new blood vessels, but these new vessels are usually fragile and disorganized. It is the growth of these abnormal new vessels that creates most of the threat to vision since they can leak, hemorrhage or lead to scarring that may end in retinal detachment. Current treatments for ischemic retinopathies seek to halt the growth of the pathological vessels but do not address the underlying ischemia that drives their growth. Furthermore, standard treatment for diabetic retinopathy, an ischemic retinopathy that affects millions, involves destruction of a portion of the retina with a laser in an attempt to stop new vessel growth and preserve central vision. Strategies have been employed to block the function of vascular endothelial growth factor (VEGF), a major promoter of vessel growth. In the short term, anti-VEGF therapy can improve vision, but it does not address the underlying ischemia and in fact may exacerbate this condition as it inhibits all vessel growth, including beneficial collaterals. There is also the serious concern of systemic exposure of these drugs in elderly and/or diabetic patients where new vessel growth may be required in ischemic brains, hearts or limbs.

Typically for ocular diseases via intravitreal application smaller antibody fragments like Fab or Fab(2) are often used as they have a low serum half-life and the risk of systemic toxicities is lower. However this smaller fragments typically have also lower intravitreal half-lives (e.g. due to the faster diffusion into serum) and have to be dosed typically more often.

Kim et al, Molecular Vision, 15 (2009) 2803-2812 relates to full length antibodies administered intravitreally in the eye, wherein an IgG with FcRn binding was eliminated into the blood in wild-type mice, whereas an IgY with no FcRn binding was not eliminated into the blood system. Furthermore the IgG with FcRn binding was not eliminated into the blood system in FcRn knockdown-mice.

There is a need in the art for better means for treating and preventing various ocular vascular diseases such as ischemic retinopathies.

SUMMARY OF THE INVENTION

One aspect of the invention is method for the reduction of the viscosity of an antibody wherein the antibody comprises a constant heavy chain region of human IgG1 or human IgG4 subclass (derived from human origin and) wherein the method comprises the modification of the antibody constant heavy chain region of human IgG1 or human IgG4 subclass with the mutations I253A, H310A, and H435A (numbering according to EU Index of Kabat).

In one embodiment of the invention said method is characterized in that the antibody is a bispecific antibody comprising a first antigen-binding site that specifically binds to human VEGF and a second antigen-binding site that specifically binds to human ANG-2, wherein
  i) said first antigen-binding site specifically binding to VEGF comprises in the heavy chain variable domain a CDR3H region of SEQ ID NO: 1, a CDR2H region of SEQ ID NO: 2, and a CDR1H region of SEQ ID NO:3, and in the light chain variable domain a CDR3L region of SEQ ID NO: 4, a CDR2L region of SEQ ID NO:5, and a CDR1L region of SEQ ID NO:6; and
  ii) said second antigen-binding site specifically binding to ANG-2 comprises in the heavy chain variable domain a CDR3H region of SEQ ID NO: 9, a CDR2H region of, SEQ ID NO: 10, and a CDR1H region of SEQ ID NO: 11, and in the light chain variable domain a CDR3L region of SEQ ID NO: 12, a CDR2L region of SEQ ID NO: 13, and a CDR1L region of SEQ ID NO: 14, and wherein
  iii) the bispecific antibody comprises a constant heavy chain region of human IgG1 or human IgG4 subclass (derived from human origin and) comprising the mutations I253A, H310A, and H435A (numbering according to EU Index of Kabat).

In one embodiment of the invention such method is characterized in that said bispecific antibody described above comprises a constant heavy chain region of human IgG1 subclass (derived from human origin and) comprising the mutations I253A, H310A, and H435A (numbering according to EU Index of Kabat) and further comprising the mutations L234A, L235A and P329G (numbering according to EU Index of Kabat).

One embodiment of the invention is an antibody obtained by such method.

One embodiment of the invention is the use of the mutations I253A, H310A, and H435A (numbering according to EU Index of Kabat) for the reduction of the viscosity of an antibody wherein the antibody comprises a constant heavy chain region of human IgG1 or human IgG4 subclass (derived from human origin).

In one embodiment of the invention said use is characterized in that the antibody is a bispecific antibody comprising a first antigen-binding site that specifically binds to human VEGF and a second antigen-binding site that specifically binds to human ANG-2, wherein
  i) said first antigen-binding site specifically binding to VEGF comprises in the heavy chain variable domain a CDR3H region of SEQ ID NO: 1, a CDR2H region of SEQ ID NO: 2, and a CDR1H region of SEQ ID NO:3, and in the light chain variable domain a CDR3L region of SEQ ID NO: 4, a CDR2L region of SEQ ID NO:5, and a CDR1L region of SEQ ID NO:6; and
  ii) said second antigen-binding site specifically binding to ANG-2 comprises in the heavy chain variable domain a CDR3H region of SEQ ID NO: 9, a CDR2H region of, SEQ ID NO: 10, and a CDR1H region of SEQ ID NO: 11, and in the light chain variable domain a CDR3L region of SEQ ID NO: 12, a CDR2L region of SEQ ID NO: 13, and a CDR1L region of SEQ ID NO: 14, and wherein
  iii) the bispecific antibody comprises a constant heavy chain region of human IgG1 or human IgG4 subclass (derived from human origin and) comprising the mutations I253A, H310A, and H435A (numbering according to EU Index of Kabat).

In one embodiment of the invention said specific use is characterized in that the bispecific antibody comprises a constant heavy chain region of human IgG1 subclass (derived from human origin and) comprising the mutations I253A, H310A, and H435A (numbering according to EU Index of Kabat) and further comprising the mutations L234A, L235A and P329G (numbering according to EU Index of Kabat).

The invention is further directed to a bispecific, bivalent antibody comprising a first antigen-binding site that specifically binds to human VEGF and a second antigen-binding site that specifically binds to human ANG-2, wherein
  i) said first antigen-binding site specifically binding to VEGF comprises in the heavy chain variable domain a CDR3H region of SEQ ID NO: 1, a CDR2H region of SEQ ID NO: 2, and a CDR1H region of SEQ ID NO:3, and in the light chain variable domain a CDR3L region of SEQ ID NO: 4, a CDR2L region of SEQ ID NO:5, and a CDR1L region of SEQ ID NO:6; and
  ii) said second antigen-binding site specifically binding to ANG-2 comprises in the heavy chain variable domain a CDR3H region of SEQ ID NO: 9, a CDR2H region of, SEQ ID NO: 10, and a CDR1H region of SEQ ID NO: 11, and in the light chain variable domain a CDR3L region of SEQ ID NO: 12, a CDR2L region of SEQ ID NO: 13, and a CDR1L region of SEQ ID NO: 14,
  and wherein
  iii) the bispecific antibody comprises a constant heavy chain region of human IgG1 or human IgG4 subclass (derived from human origin and) comprising the mutations I253A, H310A, and H435A (numbering according to EU Index of Kabat)

In one embodiment said bispecific antibody is characterized in that
  i) said first antigen-binding site specifically binding to VEGF comprises as heavy chain variable domain VH an amino acid sequence of SEQ ID NO: 7, and as light chain variable domain VL an amino acid sequence of SEQ ID NO: 8, and
  ii) said second antigen-binding site specifically binding to ANG-2 comprises as heavy chain variable domain VH an amino acid sequence of SEQ ID NO: 15, and as light chain variable domain VL an amino acid sequence of SEQ ID NO: 16.

In one embodiment said bispecific antibody is characterized in that the constant heavy chain region under iii) is of human IgG1 subclass. In one embodiment said bispecific antibody of IgG1 subclass is characterized in that the constant heavy chain region of IgG1 subclass further comprises the mutations L234A, L235A and P329G (numbering according to EU Index of Kabat)

In one embodiment said bispecific antibody is characterized in that the constant heavy chain region under iii) is of human IgG4 subclass. In one embodiment said bispecific antibody of IgG4 subclass is characterized in that the constant heavy chain region of IgG4 subclass further comprises the mutations S228P and L235E (numbering according to EU Index of Kabat). In one embodiment said bispecific antibody of IgG4 subclass is characterized in that the constant heavy chain region of IgG4 subclass further comprises the mutations S228P, L235E and P329G (numbering according to EU Index of Kabat)

Still further aspects of the invention are a pharmaceutical composition comprising said bispecific antibody, said pharmaceutical composition for use in the treatment of ocular vascular diseases, the use of said bispecific antibody for the manufacture of a medicament for the treatment of ocular vascular diseases, a method of treatment of patient suffering from ocular vascular diseases by administering said bispecific antibody to a patient in the need of such treatment. In one embodiment the bispecific antibody or the pharmaceutical composition comprising said bispecific antibody is administered via intravitreal application.

A further aspect of the invention is a nucleic acid molecule encoding a heavy and/or light chain of a bispecific antibody according to the invention.

The invention further provides expression vectors containing said nucleic acid according to the invention capable of expressing said nucleic acid in a prokaryotic or eukaryotic host cell, and host cells containing such vectors for the recombinant production of a bispecific antibody according to the invention.

The invention further comprises a prokaryotic or eukaryotic host cell comprising a vector according to the invention.

The invention further comprises a method for the production of a bispecific antibody according to the invention, characterized by expressing a nucleic acid according to the invention in a prokaryotic or eukaryotic host cell and recovering said bispecific antibody from said cell or the cell culture supernatant. One embodiment is a method for the preparation of a bispecific antibody according to the invention comprising the steps of
a) transforming a host cell with vectors comprising nucleic acid molecules encoding said antibody;
b) culturing the host cell under conditions that allow synthesis of said antibody molecule; and
c) recovering said antibody molecule from said culture The invention further comprises the antibody obtained by such method for the production of a bispecific antibody.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 21, of SEQ ID NO: 22, of SEQ ID NO: 23, and of SEQ ID NO: 24.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 25, of SEQ ID NO: 26, of SEQ ID NO: 27, and of SEQ ID NO: 28.

The antibodies according to the invention have highly valuable properties due to their specific modifications in the Fc part/constant region causing a benefit for a patient suffering from ocular vascular diseases. They show high stability in the intravitreal environment and slow diffusion from the eye (compared to smaller antibody fragments without a constant heavy chain region), where the actual disease is located and treated (so treatment schedule can potentially be improved compared to non-IgG like antibodies like e.g. Fab and (Fab)2 fragments). Surprisingly compared to unmodified IgG antibodies the half-life in the eye after intravitreal application of the antibodies with the mutations I253A, H310A, and H435A in the constant region (with no more FcRn binding) was similar (only slightly reduced) (Tables 17a and 18a and FIGS. 7D and 7E), whereas the diffusion from the eye into the blood serum was similar (Table 15 and FIG. 7B). This highly valuable as it is desired for the treatment of ocular vascular diseases related to ANG2 and/or VEGF it to eliminate VEGF and Ang2 from the eye (e. via the transportation into the blood serum as anti-ANG2/ANG2 antibody complex or anti-VEGF/VEGF antibody complex). The antibodies according to the invention are cleared on the other hand quite rapidly from serum when compared to unmodified IgG antibodies (which is highly desired to reduce potential side effects arising from systemic exposure).

Surprisingly they also show lower viscosity (see FIG. 2) (compared to versions without the mutations I253A, H310A, and H435A in the constant region) and are therefore especially useful for intravitreal application through thin needles during the treatment of eye diseases (for such application typically thin needles are used and high viscosity makes an appropriate application rather difficult). The lower viscosity also allows higher concentration formulations.

Also surprisingly the antibodies according to the invention show a lower aggregation tendency (FIG. 4) during storage (compared to versions without the mutations I253A, H310A, and H435A in the Fc part) which is critical for intravitreal application in the eye (as an aggregation in the eye can lead to complications during such treatment). The bispecific antibodies according to the invention show good efficacy in inhibition of vascular diseases.

In certain embodiments, the bispecific antibodies according to the invention due to their specific modifications in the constant region (e.g. P329G LALA) show valuable properties like no binding Fcgamma receptors which reduces the risk of side effects like thrombosis and/or unwanted cell death (due to e.g. ADCC)

DETAILED DESCRIPTION OF THE INVENTION

Figure 1:
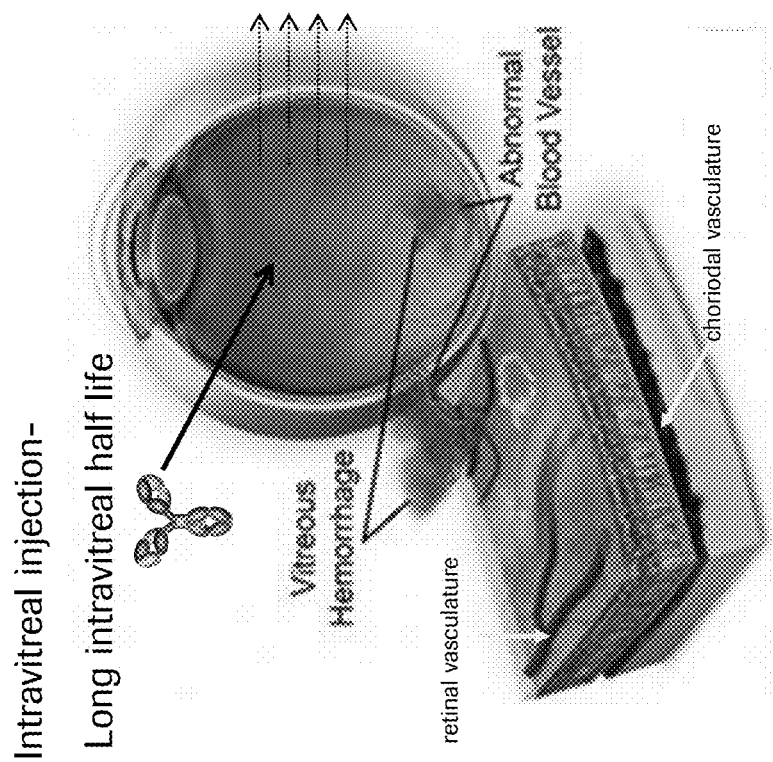
FIG. 1 Scheme of concept and advantages of <VEGF-ANG-2>IgG1 or IgG4 antibodies with AAA mutations (mutations I253A, H310A, and H435A—numbering according to EU Index of Kabat)

In one embodiment of the invention the bispecific antibody according to the invention is bivalent.

In one aspect of the invention such bispecific, bivalent antibody according to the invention is characterized in comprising
a) the heavy chain and the light chain of a first full length antibody that specifically binds to VEGF;
b) the modified heavy chain and modified light chain of a second full length antibody that specifically binds to ANG-2, wherein the constant domains CL and CH1 are replaced by each other.

This bispecific, bivalent antibody format for the bispecific antibody specifically binding to human vascular endothelial growth factor (VEGF) and human angiopoietin-2 (ANG-2) is described in WO 2009/080253 (including Knobs-into-Holes modified CH3 domains). The antibodies based on this bispecific, bivalent antibody format are named CrossMabs.

In one embodiment such bispecific, bivalent antibody is characterized in comprising
a) as heavy chain of the first full length antibody the amino acid sequence of SEQ ID NO: 25, and as light chain of the first full length antibody the amino acid sequence of SEQ ID NO: 27, and
b) as modified heavy chain of the second full length antibody the amino acid sequence of SEQ ID NO: 26, and as modified light chain of the second full length antibody the amino acid sequence of SEQ ID NO: 28.

In one embodiment such bispecific, bivalent antibody is characterized in comprising
a) as heavy chain of the first full length antibody the amino acid sequence of SEQ ID NO: 21, and as light chain of the first full length antibody the amino acid sequence of SEQ ID NO: 23, and
b) as modified heavy chain of the second full length antibody the amino acid sequence of SEQ ID NO: 22, and as modified light chain of the second full length antibody the amino acid sequence of SEQ ID NO: 24.

In one embodiment such bispecific, bivalent antibody is characterized in comprising
a) as heavy chain of the first full length antibody the amino acid sequence of SEQ ID NO: 29, and as light chain of the first full length antibody the amino acid sequence of SEQ ID NO: 31, and
b) as modified heavy chain of the second full length antibody the amino acid sequence of SEQ ID NO: 30, and as modified light chain of the second full length antibody the amino acid sequence of SEQ ID NO: 32.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 25, of SEQ ID NO: 26, of SEQ ID NO: 27, and of SEQ ID NO: 28.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 21, of SEQ ID NO: 22, of SEQ ID NO: 23, and of SEQ ID NO: 24.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 29, of SEQ ID NO: 30, of SEQ ID NO: 31, and of SEQ ID NO: 32.

In another aspect of the invention the bispecific antibody according to the invention is characterized in comprising
a) the heavy chain and the light chain of a first full length antibody that specifically binds to VEGF;
b) the heavy chain and the light chain of a second full length antibody that specifically binds to ANG-2, wherein the N-terminus of the heavy chain is connected to the C-terminus of the light chain via a peptide linker.

This bispecific, bivalent antibody format for this bispecific antibody specifically binding to human vascular endothelial growth factor (VEGF) and human angiopoietin-2 (ANG-2) is described in WO 2011/117330 including Knobs-into-Holes modified CH3 domains. The antibodies based on this bispecific, bivalent antibody format are named OAscFabs.

In one embodiment such bispecific, bivalent antibody is characterized in comprising
  a) as heavy chain of the first full length antibody the amino acid sequence of SEQ ID NO: 33, and as light chain of the first full length antibody the amino acid sequence of SEQ ID NO: 35, and
  b) as heavy chain of the second full length antibody connected to the light chain of the second full length antibody via a peptide linker the amino acid sequence of SEQ ID NO: 34.

In one embodiment such bispecific, bivalent antibody is characterized in comprising
  a) as heavy chain of the first full length antibody the amino acid sequence of SEQ ID NO: 36, and as light chain of the first full length antibody the amino acid sequence of SEQ ID NO: 38, and
  b) as heavy chain of the second full length antibody connected to the light chain of the second full length antibody via a peptide linker the amino acid sequence of SEQ ID NO: 37.

In one embodiment the antibody heavy chain variable domain (VH) and the antibody light chain variable domain (VL) of the heavy and light chain of the second full length antibody are disulfide stabilized by introduction of a disulfide bond between the following positions: heavy chain variable domain position 44 to light chain variable domain position 100 (numbering always according to EU index of Kabat (Kabat, E. A., et al., Sequences of Proteins of Immunological Interest, 5th ed., Public Health Service, National Institutes of Health, Bethesda, Md. (1991)). Such further disulfide stabilization is achieved by the introduction of a disulfide bond between the variable domains VH and VL of the second full length antibody heavy and light chain. Techniques to introduce unnatural disulfide bridges for stabilization are described e.g. in WO 94/029350, Rajagopal, V., et al, Prot. Engin. 10 (1997) 1453-59; Kobayashi et al., Nuclear Medicine & Biology 25 (1998) 387-393; or Schmidt, M., et al., Oncogene 18 (1999) 1711-1721.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 33, of SEQ ID NO: 34, and of SEQ ID NO: 35.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 36, of SEQ ID NO: 37, and of SEQ ID NO: 38.

In one embodiment the CH3 domains of the bispecific, bivalent antibody according to the invention is altered by the "knob-into-holes" technology which is described in detail with several examples in e.g. WO 96/027011, Ridgway J.B., et al., Protein Eng 9 (1996) 617-621; and Merchant, A.M., et al., Nat Biotechnol 16 (1998) 677-681. In this method the interaction surfaces of the two CH3 domains are altered to increase the heterodimerisation of both heavy chains containing these two CH3 domains. Each of the two CH3 domains (of the two heavy chains) can be the "knob", while the other is the "hole". The introduction of a disulfide bridge stabilizes the heterodimers (Merchant, A. M, et al., Nature Biotech 16 (1998) 677-681; Atwell, S., et al. J. Mol. Biol. 270 (1997) 26-35) and increases the yield.

In a preferred aspect of the invention all bispecific antibodies according to the invention are characterized in that
  the CH3 domain of one heavy chain and the CH3 domain of the other heavy chain each meet at an interface which comprises an original interface between the antibody CH3 domains;
  wherein said interface is altered to promote the formation of the bispecific antibody, wherein the alteration is characterized in that:
    a) the CH3 domain of one heavy chain is altered,
      so that within the original interface the CH3 domain of one heavy chain that meets the original interface of the CH3 domain of the other heavy chain within the bispecific antibody,
      an amino acid residue is replaced with an amino acid residue having a larger side chain volume, thereby generating a protuberance within the interface of the CH3 domain of one heavy chain which is positionable in a cavity within the interface of the CH3 domain of the other heavy chain
    and
    b) the CH3 domain of the other heavy chain is altered,
      so that within the original interface of the second CH3 domain that meets the original interface of the first CH3 domain within the bispecific antibody
      an amino acid residue is replaced with an amino acid residue having a smaller side chain volume, thereby generating a cavity within the interface of the second CH3 domain within which a protuberance within the interface of the first CH3 domain is positionable.

Thus the antibody according to invention is preferably characterized in that
  the CH3 domain of the heavy chain of the full length antibody of a) and the CH3 domain of the heavy chain of the full length antibody of b) each meet at an interface which comprises an alteration in the original interface between the antibody CH3 domains;
  wherein i) in the CH3 domain of one heavy chain
    an amino acid residue is replaced with an amino acid residue having a larger side chain volume, thereby generating a protuberance within the interface of the CH3 domain of one heavy chain which is positionable in a cavity within the interface of the CH3 domain of the other heavy chain
  and wherein
  ii) in the CH3 domain of the other heavy chain
    an amino acid residue is replaced with an amino acid residue having a smaller side chain volume, thereby generating a cavity within the interface of the second CH3 domain within which a protuberance within the interface of the first CH3 domain is positionable.

Preferably said amino acid residue having a larger side chain volume is selected from the group consisting of arginine (R), phenylalanine (F), tyrosine (Y), tryptophan (W).

Preferably said amino acid residue having a smaller side chain volume is selected from the group consisting of alanine (A), serine (S), threonine (T), valine (V).

In one aspect of the invention both CH3 domains are further altered by the introduction of cysteine (C) as amino acid in the corresponding positions of each CH3 domain such that a disulfide bridge between both CH3 domains can be formed.

In one embodiment, the bispecific antibody comprises a T366W mutation in the CH3 domain of the "knobs chain" and T366S, L368A, Y407V mutations in the CH3 domain of the "hole chain". An additional interchain disulfide bridge between the CH3 domains can also be used (Merchant, A. M, et al., Nature Biotech 16 (1998) 677-681) e.g. by introducing a Y349C mutation into the CH3 domain of the "knobs chain" and a E356C mutation or a S354C mutation into the CH3 domain of the "hole chain".

In another embodiment, the bispecific antibody according to the invention comprises Y349C, T366W mutations in one of the two CH3 domains and E356C, T366S, L368A, Y407V mutations in the other of the two CH3 domains. In a another preferred embodiment the bispecific antibody comprises Y349C, T366W mutations in one of the two CH3 domains and S354C, T366S, L368A, Y407V mutations in the other of the two CH3 domains (the additional Y349C mutation in one CH3 domain and the additional E356C or S354C mutation in the other CH3 domain forming a interchain disulfide bridge) (numbering always according to EU index of Kabat (Kabat, E.A., et al., Sequences of Proteins of Immunological Interest, 5th ed., Public Health Service, National Institutes of Health, Bethesda, Md. (1991)). But also other knobs-in-holes technologies as described by EP 1 870 459 A1, can be used alternatively or additionally. Thus another example for the bispecific antibody are R409D; K370E mutations in the CH3 domain of the "knobs chain" and D399K; E357K mutations in the CH3 domain of the "hole chain" (numbering always according to EU index of Kabat (Kabat, E.A., et al., Sequences of Proteins of Immunological Interest, 5th ed., Public Health Service, National Institutes of Health, Bethesda, Md. (1991)).

In another embodiment the bispecific antibody comprises a T366W mutation in the CH3 domain of the "knobs chain" and T366S, L368A, Y407V mutations in the CH3 domain of the "hole chain" and additionally R409D; K370E mutations in the CH3 domain of the "knobs chain" and D399K; E357K mutations in the CH3 domain of the "hole chain".

In another embodiment the bispecific antibody comprises Y349C, T366W mutations in one of the two CH3 domains and S354C, T366S, L368A, Y407V mutations in the other of the two CH3 domains or said trivalent, bispecific antibody comprises Y349C, T366W mutations in one of the two CH3 domains and S354C, T366S, L368A, Y407V mutations in the other of the two CH3 domains and additionally R409D; K370E mutations in the CH3 domain of the "knobs chain" and D399K; E357K mutations in the CH3 domain of the "hole chain".

In one embodiment of the invention the bispecific antibody according to the invention is characterized in having one or more of the following properties (determined in assays as described in Example 6
  shows a lower serum concentration compared to corresponding bispecific antibody without the mutations described under iii) (96 hours after intravitreal application in mice, which are mouse FcRn deficient, but hemizygous transgenic for human FcRn);
  shows a similar (factor 0.8 to 1.2) concentration in whole right eye lysates compared to corresponding bispecific antibody without the mutations described under iii) (in mice, which are mouse FcRn deficient, but hemizygous transgenic for human FcRn, 96 hours after intravitreal application in the right eye).

In one embodiment the bispecific, bivalent antibody is characterized in comprising
  a first antigen-binding site that specifically binds to human VEGF and a second antigen-binding site that specifically binds to human ANG-2, characterized in that i) said first antigen-binding site comprises as heavy chain variable domain (VH) the SEQ ID NO: 7, and as light chain variable domain (VL) the SEQ ID NO: 8; and
ii) said second antigen-binding site comprises as heavy chain variable domain (VH) the SEQ ID NO: 15, and as light chain variable domain (VL) the SEQ ID NO: 16; and
iii) the bispecific antibody comprises a constant heavy chain region of IgG1 or IgG4 subclass (derived from human origin and) comprising the mutations I253A, H310A, and H435A (numbering according to EU Index of Kabat)
  and having one or more of the following properties (determined in assays as described in Example 6
  shows a lower serum concentration compared to corresponding bispecific antibody without the mutations described under iii) (96 hours after intravitreal application in mice, which are mouse FcRn deficient, but hemizygous transgenic for human FcRn);
  shows a similar (factor 0.8 to 1.2) concentration in whole right eye lysates compared to corresponding bispecific antibody without the mutations described under iii) (in mice, which are mouse FcRn deficient, but hemizygous transgenic for human FcRn, 96 hours after intravitreal application in the right eye).

In one embodiment the bispecific antibody is characterized in comprising a first antigen-binding site that specifically binds to human VEGF and a second antigen-binding site that specifically binds to human ANG-2, characterized in that
i) said first antigen-binding site comprises as heavy chain variable domain (VH) the SEQ ID NO: 7 with 1, 2 or 3 amino acid residue substitutions, and as light chain variable domain (VL) the SEQ ID NO: 8 with 1, 2 or 3 amino acid residue substitutions; and
ii) said second antigen-binding site comprises as heavy chain variable domain (VH) the SEQ ID NO: 15 with 1, 2 or 3 amino acid residue substitutions, and as light chain variable domain (VL) the SEQ ID NO: with 1, 2 or 3 amino acid residue substitutions; and
iii) the bispecific antibody comprises a constant heavy chain region of IgG1 or IgG4 subclass (derived from human origin and) comprising the mutations I253A, H310A, and H435A (numbering according to EU Index of Kabat)
  and having one or more of the following properties (determined in assays as described in Example 6
  shows a lower serum concentration compared to corresponding bispecific antibody without the mutations described under iii) (96 hours after intravitreal application in mice, which are mouse FcRn deficient, but hemizygous transgenic for human FcRn);
  shows a similar (factor 0.8 to 1.2) concentration in whole right eye lysates compared to corresponding bispecific antibody without the mutations described under iii) (in mice, which are mouse FcRn deficient, but hemizygous transgenic for human FcRn, 96 hours after intravitreal application in the right eye).

As used herein, "antibody" refers to a binding protein that comprises antigen-binding sites. The terms "binding site" or "antigen-binding site" as used herein denotes the region(s) of an antibody molecule to which a ligand actually binds. The term "antigen-binding site" comprises an antibody heavy chain variable domains (VH) and an antibody light chain variable domains (VL) (pair of VH/VL)).

Antibody specificity refers to selective recognition of the antibody for a particular epitope of an antigen. Natural antibodies, for example, are monospecific.

"Bispecific antibodies" according to the invention are antibodies which have two different antigen-binding specificities. Antibodies of the present invention are specific for two different antigens, VEGF as first antigen and ANG-2 as second antigen.

The term "monospecific" antibody as used herein denotes an antibody that has one or more binding sites each of which bind to the same epitope of the same antigen.

The term "valent" as used within the current application denotes the presence of a specified number of binding sites in an antibody molecule. As such, the terms "bivalent", "tetravalent", and "hexavalent" denote the presence of two binding site, four binding sites, and six binding sites, respectively, in an antibody molecule. The bispecific antibodies according to the invention are preferably "bivalent".

The term "VEGF" as used herein refers to human vascular endothelial growth factor (VEGF/VEGF-A,) the 165-amino acid human vascular endothelial cell growth factor (amino acid 27-191 of precursor sequence of human VEGF165: SEQ ID NO: 17; amino acids 1-26 represent the signal peptide), and related 121, 189, and 206 vascular endothelial cell growth factor isoforms, as described by Leung, D.W., et al., Science 246 (1989) 1306-9; Houck et al., Mol. Endocrin. 5 (1991) 1806-1814; Keck, P.J., et al., Science 246 (1989) 1309-12 and Connolly, D.T., et al., J. Biol. Chem. 264 (1989) 20017-24; together with the naturally occurring allelic and processed forms of those growth factors. VEGF is involved in the regulation of normal and abnormal angiogenesis and neovascularization associated with tumors and intraocular disorders (Ferrara, N., et al., Endocr. Rev. 18 (1997) 4-25; Berkman, R.A., et al., J. Clin. Invest. 91 (1993) 153-159; Brown, L.F., et al., Human Pathol. 26 (1995) 86-91; Brown, L.F., et al., Cancer Res. 53 (1993) 4727-4735; Mattern, J., et al., Brit. J. Cancer. 73 (1996) 931-934; and Dvorak, H.F., et al., Am. J. Pathol. 146 (1995) 1029-1039). VEGF is a homodimeric glycoprotein that has been isolated from several sources and includes several isoforms. VEGF shows highly specific mitogenic activity for endothelial cells.

The term "ANG-2" as used herein refers to human angiopoietin-2 (ANG-2) (alternatively abbreviated with ANGPT2 or ANG2) (SEQ ID NO: 18) which is described e.g. in Maisonpierre, P. C., et al, Science 277 (1997) 55-60 and Cheung, A. H., et al., Genomics 48 (1998) 389-91. The angiopoietins-1 (SEQ ID NO: 19) and -2 were discovered as ligands for the Ties, a family of tyrosine kinases that is selectively expressed within the vascular endothelium (Yancopoulos, G. D., et al., Nature 407 (2000) 242-48). There are now four definitive members of the angiopoietin family. Angiopoietin-3 and -4 (Ang-3 and Ang-4) may represent widely diverged counterparts of the same gene locus in mouse and man (Kim, I., et al., FEBS Let, 443 (1999) 353-56; Kim, I., et al., J Biol Chem 274 (1999) 26523-28). ANG-1 and ANG-2 were originally identified in tissue culture experiments as agonist and antagonist, respectively (see for ANG-1: Davis, S., et al., Cell 87 (1996) 1161-69; and for ANG-2: Maisonpierre, P.C., et al., Science 277 (1997) 55-60). All of the known angiopoietins bind primarily to Tie2 (SEQ ID NO: 20), and both Ang-1 and -2 bind to Tie2 with an affinity of 3 nM (Kd) (Maisonpierre, P.C., et al., Science 277 (1997) 55-60).

An antigen-binding sites of the bispecific antibody of the invention contain six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences.

The antibodies of the invention comprise immunoglobulin constant regions derived from human origin of one or more immunoglobulin classes, wherein such immunoglobulin classes include IgG, IgM, IgA, IgD, and IgE classes and, in the case of IgG and IgA, their subclasses, especially IgG1 and IgG4.

The terms "monoclonal antibody" or "monoclonal antibody composition" as used herein refer to a preparation of antibody molecules of a single amino acid composition.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies.". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S.L., et al., Proc. Natl. Acad. Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M.S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M.A., and van de Winkel, J.G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Brueggemann, M., et al., Year Immunol. 7 (1993) 33-40). Human antibodies can also be produced in phage display libraries (Hoogenboom, H.R., and Winter, G., J. Mol. Biol. 227 (1992) 381-388; Marks, J.D., et al., J. Mol. Biol. 222 (1991) 581-597). The techniques of Cole, A., et al. and Boerner, P., et al. are also available for the preparation of human monoclonal antibodies (Cole, A., et al., Monoclonal Antibodies and Cancer Therapy, Liss, A.L., p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "recombinant antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant antibodies have variable and constant regions in a rearranged form. The recombinant antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable domain of a heavy chain (VH) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat, E.A., et al., Sequences of Proteins of Immunological Interest, 5th ed., Public Health Service, National Institutes of Health, Bethesda, Md. (1991).

As used herein, the term "binding" or "specifically binding" refers to the binding of the antibody to an epitope of the antigen (either human VEGF or human ANG-2) in an in vitro assay, preferably in an plasmon resonance assay (BIAcore, GE-Healthcare Uppsala, Sweden with purified wild-type antigen. The affinity of the binding is defined by the terms ka (rate constant for the association of the antibody from the antibody/antigen complex), $k_D$ (dissociation constant), and $K_D$ ($k_D$/ka). In one embodiment binding or specifically binding means a binding affinity ($K_D$) of $10^{-8}$ mol/l or less, in one embodiment $10^{-9}$ M to $10^{-13}$ mol/l.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

In certain embodiments, an antibody is said to specifically bind an antigen when it preferentially recognizes its target antigen in a complex mixture of proteins and/or macromolecules.

The term "full length antibody" denotes an antibody consisting of two "full length antibody heavy chains" and two "full length antibody light chains". A "full length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in case of an antibody of the subclass IgE. Preferably the "full length antibody heavy chain" is a polypeptide consisting in N-terminal to C-terminal direction of VH, CH1, HR, CH2 and CH3. A "full length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The two full length antibody chains are linked together via inter-polypeptide disulfide bonds between the CL domain and the CH1 domain and between the hinge regions of the full length antibody heavy chains. Examples of typical full length antibodies are natural antibodies like IgG (e.g. IgG1 and IgG2), IgM, IgA, IgD, and IgE. The full length antibodies according to the invention can be from a single species e.g. human, or they can be chimerized or humanized antibodies. The full length antibodies according to the invention comprise two antigen binding sites each formed by a pair of VH and VL, which both specifically bind to the same antigen. The C-terminus of the heavy or light chain of said full length antibody denotes the last amino acid at the C-terminus of said heavy or light chain. The N-terminus of the heavy or light chain of said full length antibody denotes the last amino acid at the N-terminus of said heavy or light chain.

The term "peptide linker" as used within the invention denotes a peptide with amino acid sequences, which is preferably of synthetic origin. These peptides according to invention are used to connect the C-terminus of the light chain to the N-terminus of heavy chain of the second full length antibody (that specifically binds to a second antigen) via a peptide linker. The peptide linker within the second full length antibody heavy and light chain is a peptide with an amino acid sequence with a length of at least 30 amino acids, preferably with a length of 32 to 50 amino acids. In one the peptide linker is a peptide with an amino acid sequence with a length of 32 to 40 amino acids. In one embodiment said linker is (GxS)n with G=glycine, S=serine, (x=3, n=8, 9 or 10 and m=0, 1, 2 or 3) or (x=4 and n=6, 7 or 8 and m=0, 1, 2 or 3), preferably with x=4, n=6 or 7 and m=0, 1, 2 or 3, more preferably with x=4, n=7 and m=2. In one embodiment said linker is $(G_4S)_6G_2$.

The term "constant region" as used within the current applications denotes the sum of the domains of an antibody other than the variable region. The constant region is not involved directly in binding of an antigen, but exhibits various effector functions. Depending on the amino acid sequence of the constant region of their heavy chains, antibodies are divided in the classes: IgA, IgD, IgE, IgG and IgM, and several of these may be further divided into subclasses, such as IgG1, IgG2, IgG3, and IgG4, IgA1 and IgA2. The heavy chain constant regions that correspond to the different classes of antibodies are called α, δ, ε, γ, and μ, respectively. The light chain constant regions which can be found in all five antibody classes are called κ (kappa) and λ (lambda).

The terms "constant region derived from human origin" or "human constant region" as used in the current application denotes a constant heavy chain region of a human antibody of the subclass IgG1, IgG2, IgG3, or IgG4 and/or a constant light chain kappa or lambda region. Such constant regions are well known in the state of the art and e.g. described by Kabat, E.A., et al., Sequences of Proteins of Immunological Interest, 5th ed., Public Health Service, National Institutes of Health, Bethesda, Md. (1991) (see also e.g. Johnson, G., and Wu, T.T., Nucleic Acids Res. 28 (2000) 214-218; Kabat, E.A., et al., Proc. Natl. Acad. Sci. USA 72 (1975) 2785-2788). Within the application for the numbering of positions and mutations the EU numbering system (EU Index) according to Kabat, E. A., et al., Sequences of Proteins of Immunological Interest, 5th ed., Public Health Service, National Institutes of Health, Bethesda, Md. (1991) is used and referred to as "numbering according to EU Index of Kabat".

In one embodiment the bispecific antibodies according to the invention have a constant region of human IgG1 subclass (derived from human IgG1 subclass).

In one embodiment the bispecific antibodies according to the invention have a constant region of human IgG4 subclass (derived from human IgG1 subclass).

In one embodiment the bispecific antibody according to the invention is of human IgG1 subclass with mutations L234A (Leu235Ala), L235A (Leu234Ala) and P329G (Pro329Gly). Such antibody has a reduced FcR binding (especially they show no more binding to FcRgammaI, FcRgammaII and FcRgammaIII). This especially useful to reduce potential side effects like e.g. thrombosis (Meyer, T., et al., J. Thromb. Haemost. 7 (2009) 171-81). In one embodiment the bispecific antibody according to the invention is of human IgG4 subclass with mutations S228P (Ser228Pro), L235E (Leu235Glu) and P329G (Pro329Gly). Such antibody shows reduced FcR binding as indicated above. While Pro329Ala mutation which was described already removes only two third of the FcgammaRIIIa sandwich interaction, the Pro329Gly in the antibodies according to the invention fully imparts binding of the Fc part to FcgammaRIII. This is especially useful as the binding to FcgammaRIII is involved in ADCC (antibody-dependent cellular toxicity) which leads to cell death, which may be helpful in the treatment of cancer diseases, but which can cause serious side effect in the antibody based treatment of other vascular or immunological diseases. So the antibodies according to the invention of IgG1 subclass with mutations L234A, L235A and P329G and IgG4 subclass with mutations S228P, L235E and P329G are especially useful, as they both show no more binding to FcRgammaI, FcRgammaII and FcRgammaIII.

The term "with (the) mutations AAA" as used herein refers the mutations I253A (Ile253Ala), H310A (His310Ala), and H435A (His435Ala) in the constant heavy chain region of IgG1 or IgG4, wherein the numbering is according to the EU Index of Kabat.

The term "with (the) mutations P329G LALA" as used herein refers to the mutations L234A (Leu235Ala), L235A (Leu234Ala) and P329G (Pro329Gly) in the constant heavy chain region of IgG1 subclass, wherein the numbering is according to the EU Index of Kabat. The term "with (the) mutations SPLE" as used herein refers to the S228P (Ser228Pro) and L235E (Leu235Glu) the constant heavy chain region of IgG4 subclass, wherein the numbering is according to the EU Index of Kabat. The term "with (the) mutations SPLE and P239G" as used herein refers to the S228P (Ser228Pro), L235E (Leu235Glu) and P329G (Pro329Gly) the constant heavy chain region of IgG4 subclass, wherein the numbering is according to the EU Index of Kabat.

The antibody according to the invention is produced by recombinant means. Thus, one aspect of the current invention is a nucleic acid encoding the antibody according to the invention and a further aspect is a cell comprising said nucleic acid encoding an antibody according to the invention. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective modified light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or *E. coli* cells, and the antibody is recovered from the cells (supernatant or cells after lysis). General methods for recombinant production of antibodies are well-known in the state of the art and described, for example, in the review articles of Makrides, S.C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160; Werner, R.G., Drug Res. 48 (1998) 870-880.

Accordingly one embodiment of the invention is a method for the preparation of a bispecific antibody according to the invention, comprising the steps of
  a) transforming a host cell with vectors comprising nucleic acid molecules encoding said antibody;
  b) culturing the host cell under conditions that allow synthesis of said antibody molecule; and
  c) recovering said antibody molecule from said culture.

In one embodiment the recovering step under c includes the use of a light chain constant domain specific capture reagent (which e.g. specific for the kappa or the lambda constant light chain, depending on whether a kappa or a lambda light chain in the bispecific antibody according to invention used). In one embodiment this light chain specific capture reagent is used in a bind-and-elute-mode). Examples of such light chain constant domain specific capture reagents are e.g. KappaSelect™ and LambdaFabSelect™ from GE Healthcare/BAC, which are based on a highly rigid agarose base matrix that allows high flow rates and low back pressure at large scale. They feature a ligand that binds to the constant region of the kappa or the lambda light chain respectively (i.e. fragments lacking the constant region of the light chain will not bind; FIG. 1). Both are therefore capable of binding other target molecules containing the constant region of the light chain, for example, IgG, IgA and IgM. The ligands are attached to the matrix via a long hydrophilic spacer arm to make it easily available for binding to the target molecule. They are based on a single-chain antibody fragment that is screened for either human Ig kappa or lambda.

The bispecific antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants (or mutants) of the bispecific antibody are prepared by introducing appropriate nucleotide changes into the antibody DNA, or by nucleotide synthesis. Such modifications can be performed, however, only in a very limited range. For example, the modifications do not alter the above mentioned antibody characteristics such as the IgG subclass and antigen binding, but may improve the yield of the recombinant production, protein stability or facilitate the purification.

The term "host cell" as used in the current application denotes any kind of cellular system which can be engineered to generate the antibodies according to the current invention. In one embodiment HEK293 cells and CHO cells are used as host cells. As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

Expression in NS0 cells is described by, e.g., Barnes, L.M., et al., Cytotechnology 32 (2000) 109-123; Barnes, L.M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M.A., Appl. Biochem. Biotech. 75 (1998) 93-102).

The bispecific, bivalent antibodies according to the invention show benefits for human patients in need of a VEGF and ANG-2 targeting therapy.

The bivalent bispecific against human VEGF and human ANG-2 according to the current invention may have a valuable efficacy/safety profile and may provide benefits for a patient in the need of an anti-VEGF and anti-ANG-2 therapy.

One aspect of the invention is a pharmaceutical composition comprising an antibody according to the invention. Another aspect of the invention is the use of an antibody according to the invention for the manufacture of a pharmaceutical composition. A further aspect of the invention is a method for the manufacture of a pharmaceutical composition comprising an antibody according to the invention. In another aspect, the present invention provides a composition, e.g. a pharmaceutical composition, containing an antibody according to the present invention, formulated together with a pharmaceutical carrier.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for administration administered to the subject via a local route. For example, the antibody or its composition can be administered to the subject by intraocular application e.g. by intraocular injection such as intravitreal injection. This can be performed in accordance with standard procedures known in the art. See, e.g., Ritter et al., J. Clin. Invest. 116 (2006) 3266-76; Russelakis-Carneiro et al., Neuropathol. Appl. Neurobiol. 25 (1999) 196-206; and Wray et al., Arch. Neurol. 33 (1976) 183-5.

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

Many possible modes of delivery can be used, including, but not limited to intraocular application or topical application. In one embodiment the application is intraocular and includes, but is not limited to, subconjunctval injection, intracanieral injection, injection into the anterior chamber via the termporal limbus, intrastromal injection, intracorneal injection, subretinal injection, aqueous humor injection, subtenon injection or sustained delivery device, intravitreal injection (e.g., front, mid or back vitreal injection). In one embodiment the application is topical and includes, but is not limited to eye drops to the cornea.

In one embodiment the bispecific antibody or pharmaceutical composition according to the invention is administered via intravitreal application, e.g. via intravitreal injection. This can be performed in accordance with standard procedures known in the art. See, e.g., Ritter et al., J. Clin. Invest. 116 (2006) 3266-76; Russelakis-Carneiro et al., Neuropathol. Appl. Neurobiol. 25 (1999) 196-206; and Wray et al., Arch. Neurol. 33 (1976) 183-5.

In some embodiments, therapeutic kits of the invention can contain one or more doses of a bispecific antibody present in a pharmaceutical composition described herein, a suitable device for intravitreal injection of the pharmaceutical composition, and an instruction detailing suitable subjects and protocols for carrying out the injection. In these embodiments, the compositions are typically administered to the subject in need of treatment via intravitreal injection. This can be performed in accordance with standard procedures known in the art. See, e.g., Ritter et al., J. Clin. Invest. 116 (2006) 3266-76; Russelakis-Carneiro et al., Neuropathol. Appl. Neurobiol. 25 (1999) 196-206; and Wray et al., Arch. Neurol. 33 (1976) 183-5.

The compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

The composition can comprise an ophthalmic depot formulation comprising an active agent for subconjunctival administration. The ophthalmic depot formulation comprises microparticles of essentially pure active agent, e.g., the bispecific antibody according to the invention. The microparticles comprising the bispecific antibody according to the invention can be embedded in a biocompatible pharmaceutically acceptable polymer or a lipid encapsulating agent. The depot formulations may be adapted to release all of substantially all the active material over an extended period of time. The polymer or lipid matrix, if present, may be adapted to degrade sufficiently to be transported from the site of administration after release of all or substantially all the active agent. The depot formulation can be liquid formulation, comprising a pharmaceutical acceptable polymer and a dissolved or dispersed active agent. Upon injection, the polymer forms a depot at the injections site, e.g. by gelifying or precipitating.

Another aspect of the invention is the bispecific antibody according to the invention for use in the treatment of ocular vascular diseases.

One embodiment of the invention is the bispecific antibody according to the invention for use in the treatment of ocular vascular diseases.

Another aspect of the invention is said pharmaceutical composition for use in the treatment of ocular vascular diseases.

Another aspect of the invention is the use of an antibody according to the invention for the manufacture of a medicament for the treatment of ocular vascular disease.

Another aspect of the invention is method of treatment of patient suffering from ocular vascular diseases by administering an antibody according to the invention to a patient in the need of such treatment.

The terms "ocular vascular disease" and "vascular eye disease" are use inter changeable herein and include, but are not limited to intraocular neovascular syndromes such as diabetic retinopathy, diabetic macular edema, retinopathy of prematurity, neovascular glaucoma, retinal vein occlusions, central retinal vein occlusions, macular degeneration, age-related macular degeneration, retinitis pigmentosa, retinal angiomatous proliferation, macular telangectasia, ischemic retinopathy, iris neovascularization, intraocular neovascularization, corneal neovascularization, retinal neovascularization, choroidal neovascularization, and retinal degeneration. (Garner, A., Vascular diseases, In: Pathobiology of ocular disease, A dynamic approach, Garner, A., and Klintworth, G.K., (eds.), 2nd edition, Marcel Dekker, New York (1994), pp. 1625-1710). As used herein, ocular vascular disorder refers to any pathological conditions characterized by altered or unregulated proliferation and invasion of new blood vessels into the structures of ocular tissues such as the retina or cornea. In one embodiment the ocular vascular disease is selected from the group consisting of: wet age-related macular degeneration (wet AMD), dry age-related macular degeneration (dry AMD), diabetic macular edema (DME), cystoid macular edema (CME), non-proliferative diabetic retinopathy (NPDR), proliferative diabetic retinopathy (PDR), cystoid macular edema, vasculitis (e.g. central retinal vein occlusion), papilloedema, retinitis, conjunctivitis, uveitis, choroiditis, multifocal choroiditis, ocular histoplasmosis, blepharitis, dry eye (Sjögren's disease) and other ophthalmic diseases wherein the eye disease or disorder is associated with ocular neovascularization, vascular leakage, and/or retinal edema. So the bispecific antibodies according to the invention are useful in the prevention and treatment of wet AMD, dry AMD, CME, DME, NPDR, PDR, blepharitis, dry eye and uveitis, also preferably wet AMD, dry AMD, blepharitis, and dry eye, also preferably CME, DME, NPDR and PDR, also preferably blepharitis, and dry eye, in particular wet AMD and dry AMD, and also particularly wet AMD. In some embodiments, the ocular disease is selected from the group consisting of wet age-related macular degeneration (wet AMD), macular edema, retinal vein occlusions, retinopathy of prematurity, and diabetic retinopathy.

Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, *Mycobacteria* infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, retinitis pigmentosa, retina edema (including macular edema), Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovascularization of the angle) and diseases caused by the abnormal proliferation of fibrovascular or fibrous tissue including all forms of proliferative vitreoretinopathy.

Retinopathy of prematurity (ROP) is a disease of the eye that affects prematurely born babies. It is thought to be caused by disorganized growth of retinal blood vessels which may result in scarring and retinal detachment. ROP can be mild and may resolve spontaneously, but may lead to blindness in serious cases. As such, all preterm babies are at risk for ROP, and very low birth weight is an additional risk factor. Both oxygen toxicity and relative hypoxia can contribute to the development of ROP.

Macular degeneration is a medical condition predominantly found in elderly adults in which the center of the inner lining of the eye, known as the macula area of the retina, suffers thinning, atrophy, and in some cases, bleeding. This can result in loss of central vision, which entails inability to see fine details, to read, or to recognize faces. According to the American Academy of Ophthalmology, it is the leading cause of central vision loss (blindness) in the United States today for those over the age of fifty years. Although some macular dystrophies that affect younger individuals are sometimes referred to as macular degeneration, the term generally refers to age-related macular degeneration (AMD or ARMD).

Age-related macular degeneration begins with characteristic yellow deposits in the macula (central area of the retina which provides detailed central vision, called fovea) called drusen between the retinal pigment epithelium and the underlying choroid. Most people with these early changes (referred to as age-related maculopathy) have good vision. People with drusen can go on to develop advanced AMD. The risk is considerably higher when the drusen are large and numerous and associated with disturbance in the pigmented cell layer under the macula. Large and soft drusen are related to elevated cholesterol deposits and may respond to cholesterol lowering agents or the Rheo Procedure.

Advanced AMD, which is responsible for profound vision loss, has two forms: dry and wet. Central geographic atrophy, the dry form of advanced AMD, results from atrophy to the retinal pigment epithelial layer below the retina, which causes vision loss through loss of photoreceptors (rods and cones) in the central part of the eye. While no treatment is available for this condition, vitamin supplements with high doses of antioxidants, lutein and zeaxanthin, have been demonstrated by the National Eye Institute and others to slow the progression of dry macular degeneration and in some patients, improve visual acuity.

Retinitis pigmentosa (RP) is a group of genetic eye conditions. In the progression of symptoms for RP, night blindness generally precedes tunnel vision by years or even decades. Many people with RP do not become legally blind until their 40s or 50s and retain some sight all their life. Others go completely blind from RP, in some cases as early as childhood. Progression of RP is different in each case. RP is a type of hereditary retinal dystrophy, a group of inherited disorders in which abnormalities of the photoreceptors (rods and cones) or the retinal pigment epithelium (RPE) of the retina lead to progressive visual loss. Affected individuals first experience defective dark adaptation or nyctalopia (night blindness), followed by reduction of the peripheral visual field (known as tunnel vision) and, sometimes, loss of central vision late in the course of the disease.

Macular edema occurs when fluid and protein deposits collect on or under the macula of the eye, a yellow central area of the retina, causing it to thicken and swell. The swelling may distort a person's central vision, as the macula is near the center of the retina at the back of the eyeball. This area holds tightly packed cones that provide sharp, clear central vision to enable a person to see form, color, and detail that is directly in the line of sight. Cystoid macular edema is a type of macular edema that includes cyst formation.

Combination Therapies: In certain embodiments the bispecific antibody or pharmaceutical composition according to the invention is administered alone (without an additional therapeutic agent) for the treatment of one or more ocular vascular diseases described herein.

In other embodiments the bispecific antibody or pharmaceutical composition according to the invention is administered in combination with one or more additional therapeutic agents or methods for the treatment of one or more ocular vascular diseases described herein.

In other embodiments, the bispecific antibody or pharmaceutical composition according to the invention is formulated in combination with one or more additional therapeutic agents and administered for the treatment of one or more ocular vascular diseases described herein.

In certain embodiments, the combination treatments provided herein include administration the bispecific antibody or pharmaceutical composition according to the invention is administered sequentially with one or more additional therapeutic agents for the treatment of one or more ocular vascular diseases described herein.

The additional therapeutic agents include, but are not limited to, Tryptophanyl-tRNA synthetase (TrpRS), EyeOO1 (Anti-VEGF Pegylated Aptamer), squalamine, RETAANE® (anecortave acetate for depot suspension; Alcon, Inc.), Combretastatin A4 Prodrug (CA4P), MACUGEN®, MIFEPREX® (mifepristone-ru486), subtenon triamcinolone acetonide, intravitreal crystalline triamcinolone acetonide, Prinomastat (AG3340—synthetic matrix metalloproteinase inhibitor, Pfizer), fluocinolone acetonide (including fluocinolone intraocular implant, Bausch & Lomb/Control Delivery Systems), VEGFR inhibitors (Sugen), VEGF-Trap (Regeneron/Aventis), VEGF receptor tyrosine kinase inhibitors such as 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787) and SU1 1248 (sunitinib), linomide, and inhibitors of integrin v.beta.3 function and angiostatin.

Other pharmaceutical therapies that can be sued used in combination the bispecific antibody or pharmaceutical composition according to the invention is administered, include, but are not limited to, VISUDYNE® with use of a non-thermal laser, PKC 412, Endovion (NeuroSearch A/S), neurotrophic factors, including by way of example Glial Derived Neurotrophic Factor and Ciliary Neurotrophic Factor, diatazem, dorzolamide, Phototrop, 9-cis-retinal, eye medication (including Echo Therapy) including phospholine iodide or echothiophate or carbonic anhydrase inhibitors, AE-941 (AEterna Laboratories, Inc.), Sirna-027 (Sima Therapeutics, Inc.), pegaptanib (NeXstar Pharmaceuticals/Gilead Sciences), neurotrophins (including, by way of example only, NT-4/5, Genentech), Cand5 (Acuity Pharmaceuticals), INS-37217 (Inspire Pharmaceuticals), integrin antagonists (including those from Jerini AG and Abbott Laboratories), EG-3306 (Ark Therapeutics Ltd.), BDM-E (BioDiem Ltd.), thalidomide (as used, for example, by EntreMed, Inc.), cardiotrophin-1 (Genentech), 2-methoxyestradiol (Allergan/Oculex), DL-8234 (Toray Industries), NTC-200 (Neurotech), tetrathiomolybdate (University of Michigan), LYN-002 (Lynkeus Biotech), microalgal compound (Aquasearch/Albany, Mera Pharmaceuticals), D-9120 (Celltech Group pic), ATX-S10 (Hamamatsu Photonics), TGF-beta 2 (Genzyme/Celtrix), tyrosine kinase inhibitors (Allergan, SUGEN, Pfizer), NX-278-L (NeXstar Pharmaceuticals/Gilead Sciences), Opt-24 (OPTIS France SA), retinal cell ganglion neuroprotectants (Cogent Neurosciences), N-nitropyrazole derivatives (Texas A&M University System), KP-102 (Krenitsky Pharmaceuticals), cyclosporin A, Timited retinal translocation", photodynamic therapy, (including, by way of example only, receptor-targeted PDT, Bristol-Myers Squibb, Co.; porfimer sodium for injection with PDT; verteporfin, QLT Inc.; rostaporfin with PDT, Miravent Medical Technologies; talaporfin sodium with PDT, Nippon Petroleum; motexafin lutetium, Pharmacyclics, Inc.), antisense oligonucleotides (including, by way of example, products tested by Novagali Pharma SA and ISIS-13650, Isis Pharmaceuticals), laser photocoagulation, drusen lasering, macular hole surgery, macular translocation surgery, implantable miniature telescopes, Phi-Motion Angiography (also known as Micro-Laser Therapy and Feeder Vessel Treatment), Proton Beam Therapy, microstimulation therapy, Retinal Detachment and Vitreous Surgery, Scleral Buckle, Submacular Surgery, Transpupillary Thermotherapy, Photosystem I therapy, use of RNA interference (RNAi), extracorporeal rheopheresis (also known as membrane differential filtration and Rheotherapy), microchip implantation, stem cell therapy, gene replacement therapy, ribozyme gene therapy (including gene therapy for hypoxia response element, Oxford Biomedica; Lentipak, Genetix; PDEF gene therapy, GenVec), photoreceptor/retinal cells transplantation (including transplantable retinal epithelial cells, Diacrin, Inc.; retinal cell transplant, Cell Genesys, Inc.), and acupuncture.

Any anti-angiogenic agent can be used in combination with the bispecific antibody or pharmaceutical composition according to the invention, including, but not limited to, those listed by Carmeliet and Jain, 2000, Nature 407:249-257. In certain embodiments, the anti-angiogenic agent is another VEGF antagonist or a VEGF receptor antagonist such as VEGF variants, soluble VEGF receptor fragments, aptamers capable of blocking VEGF or VEGFR, neutralizing anti-VEGFR antibodies, low molecule weight inhibitors of VEGFR tyrosine kinases and any combinations thereof and these include anti-VEGF aptamers (e.g. Pegaptanib), soluble recombinant decoy receptors (e.g. VEGF Trap). In certain embodiments, the anti-angiogenic agent is include corticosteroids, angiostatic steroids, anecortave acetate, angiostatin, endostatin, small interfering RNA's decreasing expression of VEGFR or VEGF ligand, post-VEGFR blockade with tyrosine kinase inhibitors, MMP inhibitors, IGFBP3, SDF-1 blockers, PEDF, gamma-secretase, Delta-like ligand 4, integrin antagonists, HIF-1 alpha blockade, protein kinase CK2 blockade, and inhibition of stem cell (i.e. endothelial progenitor cell) homing to the site of neovascularization using vascular endothelial cadherin (CD-144) and stromal derived factor (SDF)-I antibodies. Small molecule RTK inhibitors targeting VEGF receptors including PTK787 can also be used. Agents that have activity against neovascularization that are not necessarily anti-VEGF compounds can also be used and include anti-inflammatory drugs, m-Tor inhibitors, rapamycin, everolismus, temsirolismus, cyclospohne, anti-TNF agents, anti-complement agents, and nonsteroidal antiinflammatory agents. Agents that are neuroprotective and can potentially reduce the progression of dry macular degeneration can also be used, such as the class of drugs called the 'neurosteroids.' These include drugs such as dehydroepiandrosterone (DHEA) (Brand names: Prastera™ and Fidelin®), dehydroepiandrosterone sulfate, and pregnenolone sulfate. Any AMD (age-related macular degeneration) therapeutic agent can be used in combination with the bispecific antibody or pharmaceutical composition according to the invention, including but not limited to verteporfin in combination with PDT, pegaptanib sodium, zinc, or an antioxidant(s), alone or in any combination.

The terms "subject" and "patient" are used interchangeably and refer to mammals such as human patients and non-human primates, as well as experimental animals such as rabbits, rats, and mice, and other animals. Animals include all vertebrates, e.g., mammals and non-mammals, such as dogs, cats, sheeps, cows, pigs, rabbits, chickens, and etc. Preferred subjects for practicing the therapeutic methods of the present invention are human. Subjects in need of treatment include patients already suffering from an ocular vascular disease or disorder as well as those prone to developing the disorder.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham, F.L., van der Eb, A.J., Virology 52 (1973) 546-467. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, S.N., et al., PNAS. 69 (1972) 2110-2114.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The following examples, sequence listing and figures are provided to aid the understanding of the present invention, the true scope of which is set forth in the appended claims. It is understood that modifications can be made in the procedures set forth without departing from the spirit of the invention.

| Description of the Sequence Listing (Amino acid sequences) | | |
| --- | --- | --- |
| SEQ ID NO: | 1 | heavy chain CDR3H, <VEGF>ranibizumab |
| SEQ ID NO: | 2 | heavy chain CDR2H, <VEGF>ranibizumab |
| SEQ ID NO: | 3 | heavy chain CDR1H, <VEGF>ranibizumab |
| SEQ ID NO: | 4 | light chain CDR3L, <VEGF>ranibizumab |
| SEQ ID NO: | 5 | light chain CDR2L, <VEGF>ranibizumab |
| SEQ ID NO: | 6 | light chain CDR1L, <VEGF>ranibizumab |
| SEQ ID NO: | 7 | heavy chain variable domain VH, <VEGF>ranibizumab |
| SEQ ID NO: | 8 | light chain variable domain VL, <VEGF>ranibizumab |
| SEQ ID NO: | 9 | heavy chain CDR3H, <ANG-2> Ang2i_LC10 variant |
| SEQ ID NO: | 10 | heavy chain CDR2H, <ANG-2> Ang2i_LC10 variant |
| SEQ ID NO: | 11 | heavy chain CDR1H, <ANG-2> Ang2i_LC10 variant |
| SEQ ID NO: | 12 | light chain CDR3L, <ANG-2> Ang2i_LC10 variant |
| SEQ ID NO: | 13 | light chain CDR2L, <ANG-2> Ang2i_LC10 variant |
| SEQ ID NO: | 14 | light chain CDR1L, <ANG-2> Ang2i_LC10 variant |
| SEQ ID NO: | 15 | heavy chain variable domain VH, <ANG-2> Ang2i_LC10 variant |
| SEQ ID NO: | 16 | light chain variable domain VL, <ANG-2> Ang2i_LC10 variant |
| SEQ ID NO: | 17 | Human vascular endothelial growth factor (VEGF); precursor sequence of human VEGF165 |
| SEQ ID NO: | 18 | Human angiopoietin-2 (ANG-2) |
| SEQ ID NO: | 19 | Human angiopoietin-1 (ANG-1) |
| SEQ ID NO: | 20 | Human Tie-2 receptor |
| SEQ ID NO | 21 | Heavy chain 1 of <VEGF-ANG-2> CrossMAb IgG1 with AAA mutations (VEGFang2-0012) |
| SEQ ID NO | 22 | Heavy chain 2 of <VEGF-ANG-2> CrossMAb IgG1 with AAA mutations (VEGFang2-0012) |
| SEQ ID NO | 23 | Light chain 1 of <VEGF-ANG-2> CrossMAb IgG1 with AAA mutations (VEGFang2-0012) |
| SEQ ID NO | 24 | Light chain 2 of <VEGF-ANG-2> CrossMAb IgG1 with AAA mutations (VEGF-Ang2-0012) |
| SEQ ID NO: | 25 | Heavy chain 1 of <VEGF-ANG-2> CrossMAb IgG1 with AAA mutations and P329G LALA mutations (VEGFang2-0016) |
| SEQ ID NO: | 26 | Heavy chain 2 of <VEGF-ANG-2> CrossMAb IgG1 with AAA mutations and P329G LALA mutations (VEGFang2-0016) |
| SEQ ID NO: | 27 | Light chain 1 of <VEGF-ANG-2> CrossMAb IgG1 with AAA mutations and P329G LALA mutations (VEGFang2-0016) |
| SEQ ID NO: | 28 | Light chain 2 of <VEGF-ANG-2> CrossMAb IgG1 with AAA mutations and P329G LALA mutations (VEGFang2-0016) |
| SEQ ID NO: | 29 | Heavy chain 1 of <VEGF-ANG-2> CrossMAb IgG4 with AAA mutations and with SPLE mutations |
| SEQ ID NO: | 30 | Heavy chain 2 of <VEGF-ANG-2> CrossMAb IgG4 with AAA mutations and with SPLE mutations |
| SEQ ID NO: | 31 | Light chain 1 of <VEGF-ANG-2> CrossMAb IgG4 with AAA mutations and with SPLE mutations |
| SEQ ID NO: | 32 | Light chain 2 of <VEGF-ANG-2> CrossMAb IgG4 with AAA mutations and with SPLE mutations |
| SEQ ID NO: | 33 | Heavy chain 1 of <VEGF-ANG-2> OAscFab IgG1 with AAA mutations |
| SEQ ID NO: | 34 | Heavy chain 2 of <VEGF-ANG-2> OAscFab IgG1 with AAA mutations |
| SEQ ID NO: | 35 | Light chain 1 of <VEGF-ANG-2> OAscFab IgG1 with AAA mutations |
| SEQ ID NO: | 36 | Heavy chain 1 of <VEGF-ANG-2> OAscFab IgG4 with AAA mutations and with SPLE mutations |
| SEQ ID NO: | 37 | Heavy chain 2 of <VEGF-ANG-2> OAscFab IgG4 with AAA mutations and with SPLE mutations |
| SEQ ID NO: | 38 | Light chain 1 of <VEGF-ANG-2> OAscFab IgG4 with AAA mutations and with SPLE mutations |
| SEQ ID NO: | 39 | Heavy chain 1 of <VEGF-ANG-2> CrossMAb IgG1 wild type (without AAA mutations) (VEGFang2-0201) |

-continued

| Description of the Sequence Listing (Amino acid sequences) | | |
|---|---|---|
| SEQ ID NO: | 40 | Heavy chain 2 of <VEGF-ANG-2> CrossMAb IgG1 wild type (without AAA mutations) (VEGFang2-0201) |
| SEQ ID NO: | 41 | Light chain 1 of <VEGF-ANG-2> CrossMAb IgG1 wild type (without AAA mutations) (VEGFang2-0201) |
| SEQ ID NO: | 42 | Light chain 2 of <VEGF-ANG-2> CrossMAb IgG1 wild type (without AAA mutations) (VEGFang2-0201) |
| SEQ ID NO: | 43 | Heavy chain 1 of <VEGF-ANG-2> CrossMAb IgG1 with P329G LALA mutations only (without AAA mutations) (VEGFang2-0015) |
| SEQ ID NO: | 44 | Heavy chain 2 of <VEGF-ANG-2> CrossMAb IgG1 with P329G LALA mutations only (without AAA mutations) (VEGFang2-0015) |
| SEQ ID NO: | 45 | Light chain 1 of <VEGF-ANG-2> CrossMAb IgG1 with P329G LALA mutations only (without AAA mutations) (VEGFang2-0015) |
| SEQ ID NO: | 46 | Light chain 2 of <VEGF-ANG-2> CrossMAb IgG1 with P329G LALA mutations only (without AAA mutations) (VEGFang2-0015) |
| SEQ ID NO: | 47 | kappa light chain constant region |
| SEQ ID NO: | 48 | lambda light chain constant region |
| SEQ ID NO: | 49 | heavy chain constant region derived from human IgG1 |
| SEQ ID NO: | 50 | heavy chain constant region derived from human IgG4 |

In the Following, Embodiments of the Invention are Listed:

1. A bispecific antibody comprising a first antigen-binding site that specifically binds to human VEGF and a second antigen-binding site that specifically binds to human ANG-2,
   wherein
   i) said first antigen-binding site specifically binding to VEGF comprises in the heavy chain variable domain a CDR3H region of SEQ ID NO: 1, a CDR2H region of SEQ ID NO: 2, and a CDR1H region of SEQ ID NO:3, and in the light chain variable domain a CDR3L region of SEQ ID NO: 4, a CDR2L region of SEQ ID NO:5, and a CDR1L region of SEQ ID NO:6; and
   ii) said second antigen-binding site specifically binding to ANG-2 comprises in the heavy chain variable domain a CDR3H region of SEQ ID NO: 9, a CDR2H region of, SEQ ID NO: 10, and a CDR1H region of SEQ ID NO: 11, and in the light chain variable domain a CDR3L region of SEQ ID NO: 12, a CDR2L region of SEQ ID NO: 13, and a CDR1L region of SEQ ID NO: 14, and wherein
   iii) the bispecific antibody comprises a constant heavy chain region of human IgG1 or human IgG4 subclass (derived from human origin and) comprising the mutations I253A, H310A, and H435A (numbering according to EU Index of Kabat)

2. The bispecific antibody according to embodiment 1, wherein
   i) said first antigen-binding site specifically binding to VEGF comprises as heavy chain variable domain VH an amino acid sequence of SEQ ID NO: 7, and as light chain variable domain VL an amino acid sequence of SEQ ID NO: 8, and
   ii) said second antigen-binding site specifically binding to ANG-2 comprises as heavy chain variable domain VH an amino acid sequence of SEQ ID NO: 15, and as light chain variable domain VL an amino acid sequence of SEQ ID NO: 16.

3. The bispecific antibody according to any one of embodiments 1 to 2, wherein the constant heavy chain region under iii) is of IgG1 subclass 4. The bispecific antibody according to embodiment 3, wherein the constant heavy chain region of IgG1 subclass further comprises the mutations L234A, L235A and P329G (numbering according to EU Index of Kabat)

5. The bispecific antibody according to any one of embodiments 1 to 2, wherein the constant heavy chain region under iii) is of IgG4 subclass 6. The bispecific antibody according to embodiment 5, wherein the constant heavy chain region of IgG4 subclass further comprises the mutations S228P and L235E (numbering according to EU Index of Kabat)

7. The bispecific antibody according to embodiment 5, wherein the constant heavy chain region of IgG4 subclass further comprises the mutations S228P, L235E and P329G (numbering according to EU Index of Kabat)

8. A pharmaceutical composition comprising an antibody according to any one of embodiments 1 to 7.

9. The bispecific antibody according to any one of embodiments 1 to 7 for use in the treatment of ocular vascular diseases.

10. Use of the bispecific antibody according to any one of embodiments 1 to 7 for the manufacture of a medicament for the treatment of ocular vascular diseases.

11. The bispecific antibody according to any one of embodiments 9 or 10, wherein the antibody is administered via intravitreal application.

12. A method of treatment of patient suffering from ocular vascular diseases by administering an antibody according to any one of embodiments 1 to 7 to a patient in the need of such treatment.

13. A nucleic acid encoding a bispecific antibody according to any one of embodiments 1 to 7.

14. Expression vector containing said nucleic acid according embodiment 13 capable of expressing said nucleic acid in a prokaryotic or eukaryotic host cell.

15. A prokaryotic or eukaryotic host cell comprising a vector according to embodiment 14.

16. A method for the preparation of a bispecific antibody according to embodiments 1 to 7
   comprising the steps of
   a) transforming a host cell with vectors comprising nucleic acid molecules encoding said antibody;
   b) culturing the host cell under conditions that allow synthesis of said antibody molecule; and
   c) recovering said antibody molecule from said culture.

17. A bispecific antibody obtained by the method of embodiment 16.

18. A bispecific, bivalent antibody comprising a first antigen-binding site that specifically binds to human VEGF and a second antigen-binding site that specifically binds to human ANG-2, characterized in comprising the amino acid sequences of SEQ ID NO: 25, of SEQ ID NO: 26, of SEQ ID NO: 27, and of SEQ ID NO: 28.

19. A bispecific, bivalent antibody comprising a first antigen-binding site that specifically binds to human VEGF and a second antigen-binding site that specifically binds to human ANG-2, characterized in comprising the amino acid sequences of SEQ ID NO: 21, of SEQ ID NO: 22, of SEQ ID NO: 23, and of SEQ ID NO: 24.

20. A bispecific, bivalent antibody comprising a first antigen-binding site that specifically binds to human VEGF and a second antigen-binding site that specifically binds to human ANG-2, characterized in comprising the amino acid sequences of SEQ ID NO: 29, of SEQ ID NO: 30, of SEQ ID NO: 31, and of SEQ ID NO: 32.

Experimental Procedures

TABLE 1

Bispecific antibodies and their respective sequences

| Description | Short Name | Sequences |
|---|---|---|
| <VEGF-ANG-2> CrossMAb IgG1 with AAA mutations | VEGFang2-0012 | SEQ ID NO: 21, SEQ ID NO: 22, SEQ ID NO: 23, SEQ ID NO: 24 |
| <VEGF-ANG-2> CrossMAb IgG1 wild type (without AAA mutations) | VEGFang2-0201- | SEQ ID NO: 39, SEQ ID NO: 40, SEQ ID NO: 41, SEQ ID NO: 42 |
| <VEGF-ANG-2> CrossMAb IgG1 with AAA mutations and P329G LALA mutations | VEGFang2-0016 | SEQ ID NO: 25, SEQ ID NO: 26, SEQ ID NO: 27, SEQ ID NO: 28 |
| <VEGF-ANG-2> CrossMAb IgG1 with P329G LALA mutations only (without AAA mutations) | VEGFang2-0015 | SEQ ID NO: 43, SEQ ID NO: 44, SEQ ID NO: 45, SEQ ID NO: 46 |
| <VEGF-ANG-2> CrossMAb IgG4 with AAA mutations and with SPLE mutations | — | SEQ ID NO: 29, SEQ ID NO: 30, SEQ ID NO: 31, SEQ ID NO: 32 |
| <VEGF-ANG-2> OAscFab IgG1 with AAA mutations | — | SEQ ID NO: 33, SEQ ID NO: 34, SEQ ID NO: 35 |
| <VEGF-ANG-2> OAscFab IgG4 with AAA mutations and with SPLE mutations | — | SEQ ID NO: 36, SEQ ID NO: 37, SEQ ID NO: 38 |

Please note that the term "with (the) mutations AAA" as used herein refers the mutations I253A (Ile253Ala), H310A (His310Ala), and H435A (His435Ala) in the constant heavy chain region of IgG1 or IgG4 (numbering according to EU Index of Kabat), the term "with (the) mutations P329G LALA" as used herein refers to the mutations L234A (Leu235Ala), L235A (Leu234Ala) and P329G (Pro329Gly) in the constant heavy chain region of IgG1 subclass (numbering according to EU Index of Kabat), and the term "with (the) mutations SPLE" as used herein refers to the S228P (Ser228Pro) and L235E (Leu235Glu) the constant heavy chain region of IgG4 subclass (numbering according to EU Index of Kabat).

EXAMPLES

Materials & General Methods

General information regarding the nucleotide sequences of human immunoglobulin light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered and referred to according to EU numbering (Edelman, G. M., et al., Proc. Natl. Acad. Sci. USA 63 (1969) 78-85; Kabat, E. A., et al., Sequences of Proteins of Immunological Interest, 5th ed., Public Health Service, National Institutes of Health, Bethesda, Md. (1991)).

Recombinant DNA Techniques

Standard methods were used to manipulate DNA as described in Sambrook, J. et al., Molecular Cloning: A laboratory manual; Cold Spring Harbor Laboratory Press, Cold Spring Harbor, N.Y. (1989). The molecular biological reagents were used according to the manufacturer's instructions.

Gene Synthesis

Desired gene segments were ordered according to given specifications at Geneart (Regensburg, Germany).

DNA Sequence Determination

DNA sequences were determined by double strand sequencing performed at MediGenomix GmbH (Martinsried, Germany) or Sequiserve GmbH (Vaterstetten, Germany).

DNA and Protein Sequence Analysis and Sequence Data Management

The GCG's (Genetics Computer Group, Madison, Wis.) software package version 10.2 and Infomax's Vector NT1 Advance suite version 8.0 was used for sequence creation, mapping, analysis, annotation and illustration.

Expression Vectors

For the expression of the described antibodies, variants of expression plasmids for transient expression (e.g. in HEK293-F) cells based either on a cDNA organization with or without a CMV-Intron A promoter or on a genomic organization with a CMV promoter were applied.

Beside the antibody expression cassette the vectors contained:

an origin of replication which allows replication of this plasmid in *E. coli*, a β-lactamase gene which confers ampicillin resistance in *E. coli*, and the dihydrofolate reductase gene from *Mus musculus* as a selectable marker in eukaryotic cells The transcription unit of the antibody gene was composed of the following elements:

unique restriction site(s) at the 5' end the immediate early enhancer and promoter from the human cytomegalovirus, followed by the Intron A sequence in the case of the cDNA organization, a 5'-untranslated region of a human antibody gene, an immunoglobulin heavy chain signal sequence, the human antibody chain (wildtype or with domain exchange) either as cDNA or as genomic organization with the immunoglobulin exon-intron organization a 3' untranslated region with a polyadenylation signal sequence, and unique restriction site(s) at the 3' end.

The fusion genes comprising the antibody chains as described below were generated by PCR and/or gene synthesis and assembled by known recombinant methods and techniques by connection of the according nucleic acid segments e.g. using unique restriction sites in the respective vectors. The subcloned nucleic acid sequences were verified by DNA sequencing. For transient transfections larger quantities of the plasmids were prepared by plasmid preparation from transformed *E. coli* cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

The bispecific antibodies were expressed by transient co-transfection of the respective expression plasmids in in HEK29-F cells growing in suspension as described below.

Example 1

Expression and Purification

Transient Transfections in HEK293-F System

The bispecific antibodies were generated by transient transfection with the respective plasmids (e.g. encoding the heavy and modified heavy chain, as well as the corresponding light and modified light chain) using the HEK293-F system (Invitrogen) according to the manufacturer's instruction. Briefly, HEK293-F cells (Invitrogen) growing in suspension either in a shake flask or in a stirred fermenter in serum-free FreeStyle™ 293 expression medium (Invitrogen) were transfected with a mix of the four expression plasmids and 293Fectin™ or fectin (Invitrogen). For 2 L shake flask (Corning) HEK293-F cells were seeded at a density of 1.0E*6 cells/mL in 600 mL and incubated at 120 rpm, 8% $CO_2$. The day after the cells were transfected at a cell density of ca. 1.5E*6 cells/mL with ca. 42 mL mix of A) 20 mL Opti-MEM™ (Invitrogen) with 600 μg total plasmid DNA (1 μg/mL) encoding the heavy or modified heavy chain, respectively and the corresponding light chain in an equimolar ratio and B) 20 ml Opti-MEM™+1.2 mL 293 fectin or fectin (2 μl/mL). According to the glucose consumption glucose solution was added during the course of the fermentation. The supernatant containing the secreted antibody was harvested after 5-10 days and antibodies were either directly purified from the supernatant or the supernatant was frozen and stored.

Purification

Bispecific antibodies were purified from cell culture supernatants by affinity chromatography using MabSelect-Sure-Sepharose® (for non_AAA mutants) (GE Healthcare, Sweden) or kappaSelect-Agarose (for AAA mutants) (GE Healthcare, Sweden), hydrophobic interaction chromatography using butyl-Sepharose® (GE Healthcare, Sweden) and Superdex 200 size exclusion (GE Healthcare, Sweden) chromatography.

Briefly, sterile filtered cell culture supernatants were captured on a MabSelect SuRe™ resin equilibrated with PBS buffer (10 mM $Na_2HPO_4$, 1 mM $KH_2PO_4$, 137 mM NaCl and 2.7 mM KCl, pH 7.4), washed with equilibration buffer and eluted with 25 mM sodium citrate at pH 3.0. The AAA mutants were captured on a kappaSelect resin equilibrated with 25 mM Tris, 50 mM NaCl, pH 7.2, washed with equilibration buffer and eluted with 25 mM sodium citrate pH 2.9. The eluted protein fractions were pooled and neutralized with 2M Tris, pH 9.0. The antibody pools were prepared for hydrophobic interaction chromatography by adding 1.6 M ammonium sulfate solution to a final concentration of 0.8 M ammonium sulfate and the pH adjusted to pH 5.0 using acetic acid. After equilibration of the butyl-Sepharose®resin with 35 mM sodium acetate, 0.8 M ammonium sulfate, pH 5.0, the antibodies were applied to the resin, washed with equilibration buffer and eluted with a linear gradient to 35 mM sodium acetate pH 5.0. The bispecific antibody containing fractions were pooled and further purified by size exclusion chromatography using a Superdex 200 26/60 GL (GE Healthcare, Sweden) column equilibrated with 20 mM histidine, 140 mM NaCl, pH 6.0. The bispecific antibody containing fractions were pooled, concentrated to the required concentration using Vivaspin ultrafiltration devices (Sartorius Stedim Biotech S.A., France) and stored at −80° C.

TABLE 2

Yields of bispecific <VEGF-ANG-2> antibodies

|  | VEGFang2-0015 (without AAA mutation) | VEGFang2-0016 (with AAA mutation) |
|---|---|---|
| Titer supernatant | 64 μg/ml, (2 L = 128 mg) | n.a. (2 L scale) |
| Protein A (MabSelectSure) | 118 mg (~70% monomer) | n.a. |
| Kappa Select | n.a. | 117 mg (~83% monomer) |
| Butyl Sepharose | 60 mg | 57 mg |
| SEC | 35 mg (>95% monomer) | 38 mg (>95% monomer) |

Purity and antibody integrity were analyzed after each purification step by CE-SDS using microfluidic LabChip® technology (Caliper Life Science, USA). 5 μl of protein solution was prepared for CE-SDS analysis using the HT Protein Express Reagent Kit according manufacturer's instructions and analysed on LabChip® GXII system using a HT Protein Express Chip. Data were analyzed using LabChip® GX Software.

TABLE 3

Removal of typical side products by different sequential purification steps determined by CE-SDS.

| | VEGFang2-0015 | | | | | | VEGFang2-0016 | | | | | |
|---|---|---|---|---|---|---|---|---|---|---|---|---|
| | % peak area * * analysis: CE-SDS (Caliper Labchip GXII) | | | | | | | | | | | |
| Purification Step | mab | ¾ ab | (HC)2 | ½ ab | (LC)2 | LC | mab | ¾ ab | (HC)2 | ½ ab | (LC)2 | LC |
| Mab Select Sure | 55.7 | 19 | 10.6 | 9.8 | 3.5 | 0.9 | | | | — | | |
| Kappa Select | | | — | | | | 63 | 13.4 | 3.5 | 6.1 | 5.8 | 7.4 |
| Butyl-Sepharose | 81.4 | 1.9 | 2.3 | 8.2 | 3.6 | 1.8 | 76.2 | 1.3 | 0.7 | 8.3 | 7.7 | 5.8 |
| Superdex 200_SEC | 92.4 | 1.8 | 2.6 | 1.4 | 0.5 | 0.5 | 99 | 1.1 | n.d. | n.d. | n.d. | n.d. |

The aggregate content of antibody samples was analyzed by high-performance SEC using a Superdex 200 analytical size-exclusion column (GE Healthcare, Sweden) in 2×PBS (20 mM $Na_2HPO_4$, 2 mM $KH_2PO_4$, 274 mM NaCl and 5.4 mM KCl, pH 7.4) running buffer at 25° C. 25 μg protein were injected on the column at a flow rate of 0.75 ml/min and eluted isocratic over 50 minutes.

Analogously the <VEGF-ANG-2>bispecific antibodies VEGFang2-0012 and VEGFang2-0201 were prepared and purified with the following yields:

|  | VEGFang2-0012 (with AAA mutation) | VEGFang2-0201 (without AAA mutation) |
|---|---|---|
| Titer//amount | — | 36 µg/ml//72 mg |
| Scale | 2.1 L | 2 L |
| Protein A (MabSelectSure) | — | 66 mg (~95% monomer) |
| kappaSelect | 43 mg (~65% monomer) | — |
| Butyl Sepharose | — | 45 mg |
| SEC | 14 mg | 21 mg (>98% monomer) |
| Yield hydoxylapatite | 8.5 mg (>98% monomer) | |
| Totatl yield (recovery) | 8.5 mg (20%) | 21 mg (30%) |

Also the <VEGF-ANG-2>bispecific antibodies <VEGF-ANG-2>CrossMAb IgG4 with AAA mutations and with SPLE mutations (SEQ ID NO: 29, SEQ ID NO: 30, SEQ ID NO: 31, SEQ ID NO: 32), <VEGF-ANG-2>OAscFab IgG1 with AAA mutations (SEQ ID NO: 33, SEQ ID NO: 34, SEQ ID NO: 35) and <VEGF-ANG-2>OAscFab IgG4 with AAA mutations and with SPLE mutations (SEQ ID NO: 36, SEQ ID NO: 37, SEQ ID NO: 38) can be prepared and purified analogously.

Example 2

Analytics & Developability

Small-Scale DLS-Based Viscosity Measurement.

Viscosity measurement was essentially performed as described in (He, F. et al., Analytical Biochemistry 399 (2009) 141-3). Briefly, samples are concentrated to various protein concentrations in 200 mM arginine succinate, pH 5.5, before polystyrene latex beads (300 nm diameter) and Polysorbate 20 (0.02% v/v) are added. Samples are transferred into an optical 384-well plate by centrifugation through a 0.4 µm filter plate and covered with paraffine oil. The apparent diameter of the latex beads is determined by dynamic light scattering at 25° C. The viscosity of the solution can be calculated as $\eta=\eta0(rh/rh,0)$ ($\eta$: viscosity; $\eta0$: viscosity of water; rh: apparent hydrodynamic radius of the latex beads; rh,0: hydrodynamic radius of the latex beads in water.

To allow comparison of various samples at the same concentration, viscosity-concentration data were fitted with the Mooney equation (Equation 1) (Mooney, Colloid Sci, 1951; Monkos, Biochem. Biophys. Acta 1997) and data interpolated accordingly.

$$\eta = \eta_0 \exp\left(\frac{S\Phi}{1 - K\Phi}\right) \quad \text{Equation 1}$$

(S: hydrodynamic interaction parameter of the protein; K: self-crowding factor; $\Phi$: volume fraction of the dissolved protein)

Figure 2:
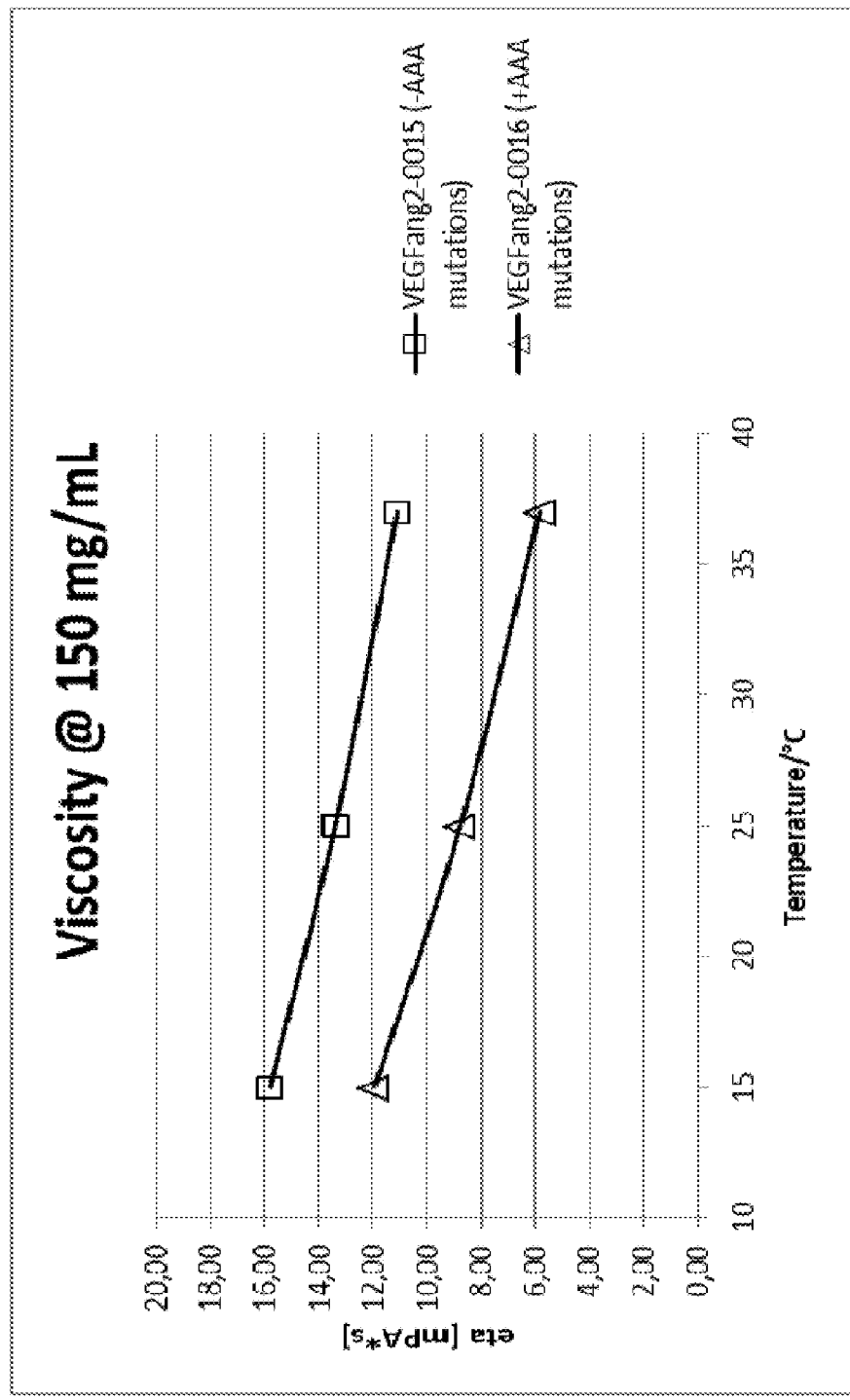
FIG. 2 Small-scale DLS-based viscosity measurement Extrapolated viscosity at 150 mg/mL in 200 mM Arginine/Succinate, pH 5.5 (comparison of <VEGF-ANG-2>antibodies according to the invention VEGFang2-0016 (with AAA mutations) with a reference VEGFang2-0015 (without such AAA mutations)

Results are shown in FIG. 2: VEGFang2-0016 with AAA mutations in the Fc part shows a lower viscosity at all measured temperatures compared to VEGFang2-0015 without the AAA mutations in the Fc part.

DLS Aggregation Onset Temperature

Figure 3:
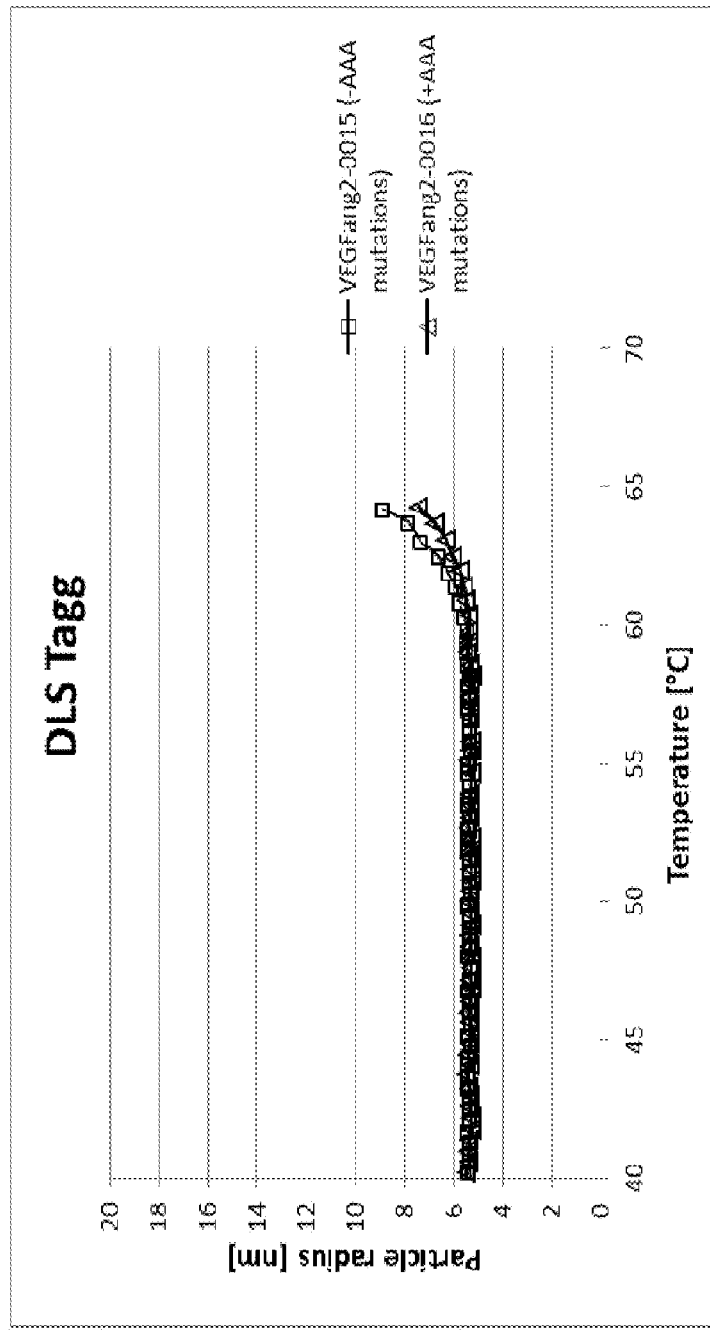
FIG. 3 DLS Aggregation depending on temperature (including DLS aggregation onset temperature) in 20 mM His, 140 mM NaCl, pH 6.0 5 (comparison of <VEGF-ANG-2>antibodies according to the invention VEGFang2-0016 (with AAA mutations) with a reference VEGFang2-0015 (without such AAA mutations)

Samples are prepared at a concentration of 1 mg/mL in 20 mM Histidine/Histidine chloride, 140 mM NaCl, pH 6.0, transferred into an optical 384-well plate by centrifugation through a 0.4 µm filter plate and covered with paraffine oil. The hydrodynamic radius is measured repeatedly by dynamic light scattering while the samples are heated with a rate of 0.05° C./min from 25° C. to 80° C. The aggregation onset temperature is defined as the temperature at which the hydrodynamic radius starts to increase. Results are shown in FIG. 3. In FIG. 3 the aggregation of VEGFang2-0015 without the AAA mutations versus VEGFang2-0016 with AAA mutations in the Fc part is shown. VEGFang2-0016 showed a aggregation onset temperature of 61° C. whereas VEGFang2-0015 without the AAA mutations showed a onset temperature of 60° C.

DLS Timecourse

Samples are prepared at a concentration of 1 mg/mL in 20 mM Histidine/Histidine chloride, 140 mM NaCl, pH 6.0, transferred into an optical 384-well plate by centrifugation through a 0.4 µm filter plate and covered with paraffine oil. The hydrodynamic radius is measured repeatedly by dynamic light scattering while the samples are kept at a constant temperature of 50° C. for up to 145 hours. In this experiment, aggregation tendencies of the native, unfolded protein at elevated temperature would lead to an increase of the average particle diameter over time. This DLS-based method is very sensitive for aggregates because these contribute over-proportionally to the scattered light intensity. Even after 145 hours at 50° C. (a temperature close to the aggregation-onset temperature, see above), an average particle diameter increase of only less than 0.5 nm was found for both VEGFang2-0015 and VEGFang2-0016

7 Day Storage at 40° C. at 100 Mg/Ml (HMW Increase)

Figure 4:
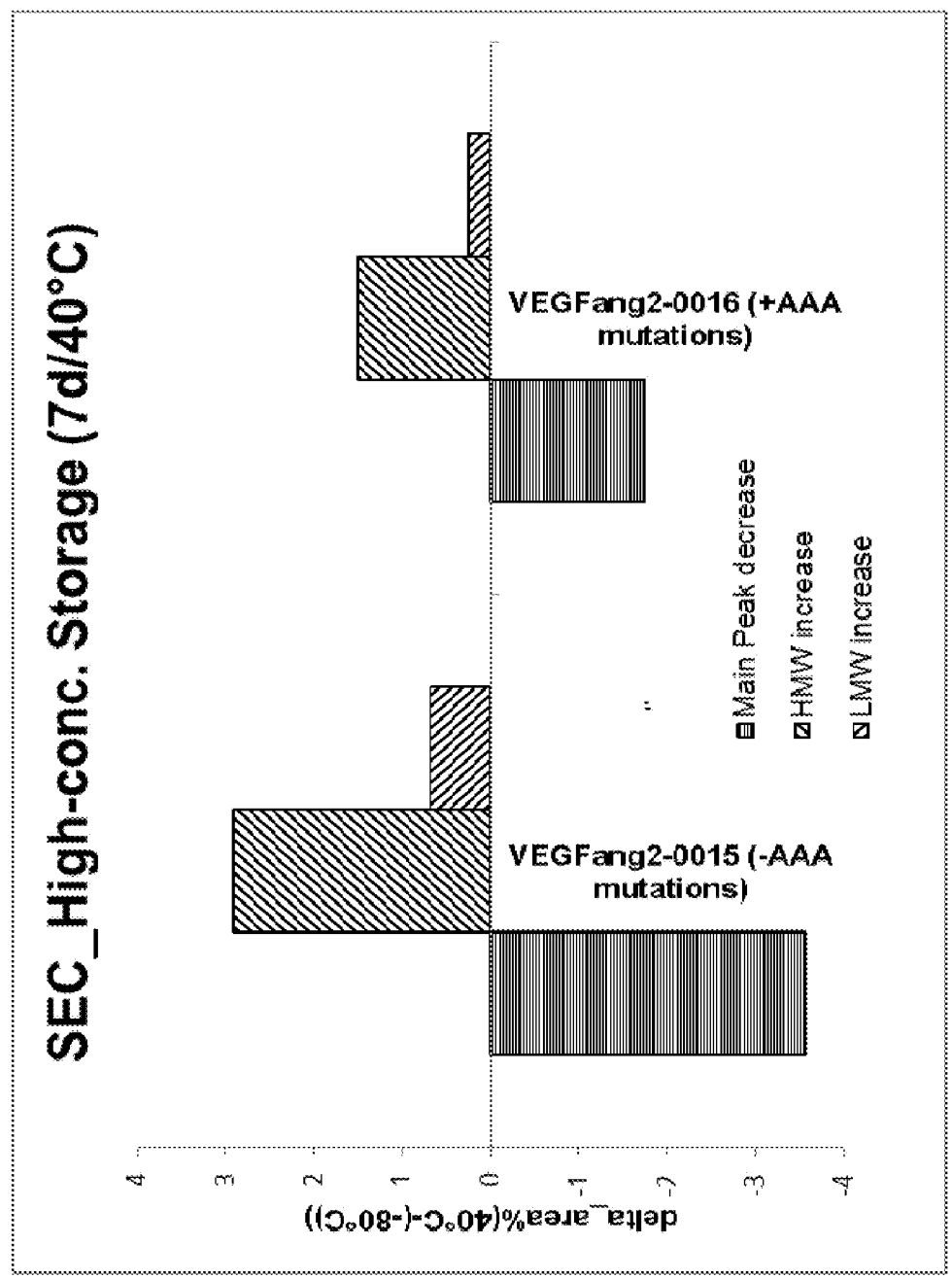
FIG. 4 7 day storage at 40° C. at 100 mg/ml (Decrease of Main and High Molecular Weight/HMW) increase) (comparison of <VEGF-ANG-2>antibodies according to the invention VEGFang2-0016 (with AAA mutations) which showed a lower aggregation with a reference VEGFang2-0015 (without such AAA mutations))
Figure 5A:
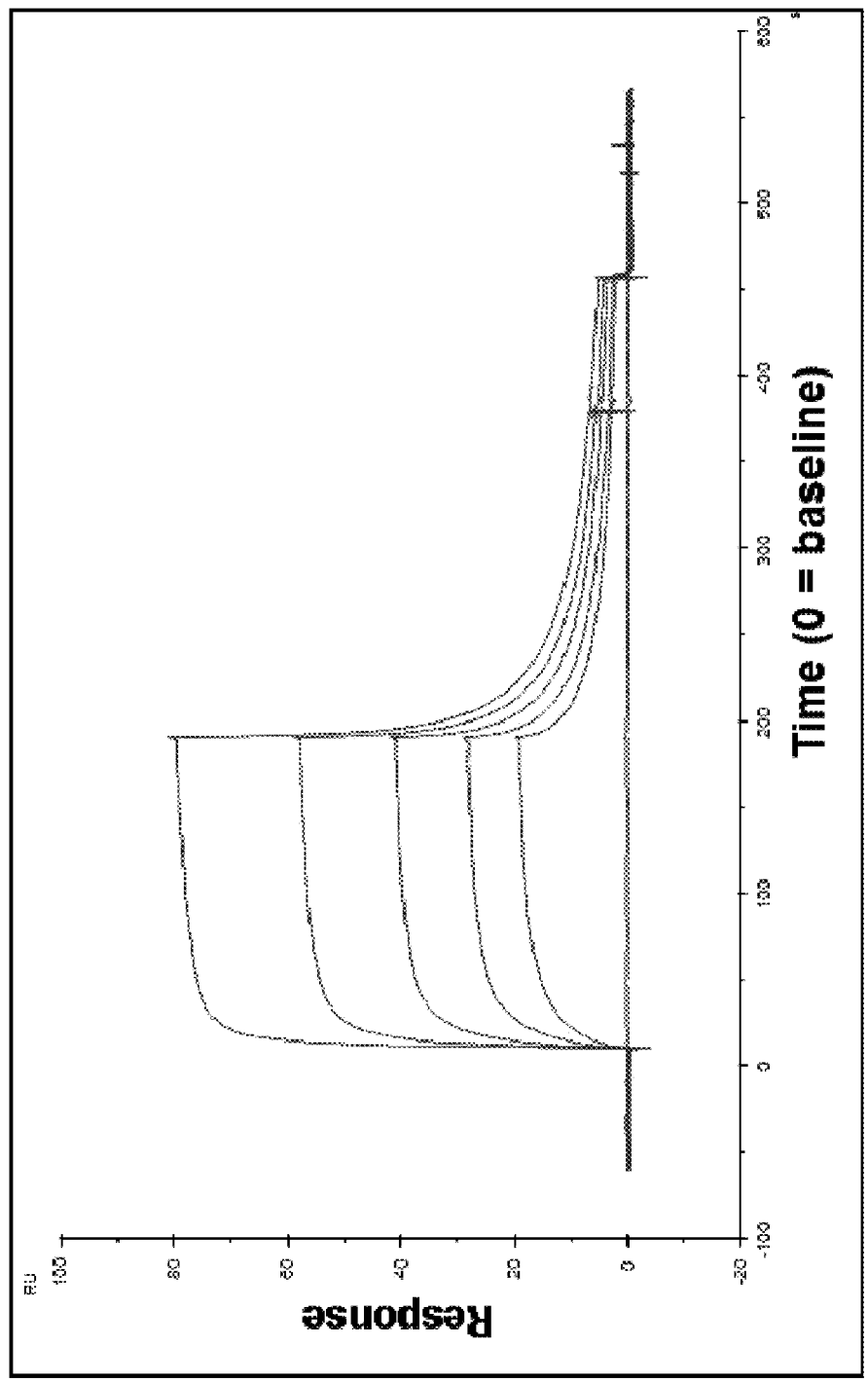
FIG. 5A FcRn steady state affinity of VEGFang2-0015 (without AAA mutations): overlay of Biacore sensogramms at different concentrations shows a concentration dependent binding of VEGFang2-0015 (without AAA mutations) to FcRn FIG. 5B FcRn steady state affinity of A: VEGFang2-0015 (without AAA mutations): the concentration dependent binding response curve of VEGFang2-0015 (without AAA mutations) shows binding to FcRn FIG. 5C FcRn steady state affinity of VEGFang2-0016 (with AAA mutations): overlay of Biacore sensogramms at different concentrations shows no binding to FcRn at all concentrations FIG. 5D FcRn steady state affinity of VEGFang2-0016 (with AAA mutations): the concentration dependent binding response curve of VEGFang2-0016 (with AAA mutations) shows no binding to FcRn FIG. 5E FcRn steady state affinity of VEGFang2-0016 (with AAA mutations): the concentration dependent binding response curve of VEGFang2-0016 (with AAA mutations) shows no binding to FcRn (Response range from −0.6 to 0.2 RU/ concentration scale ranges from 0 to 0.35 M)
Figure 5C:
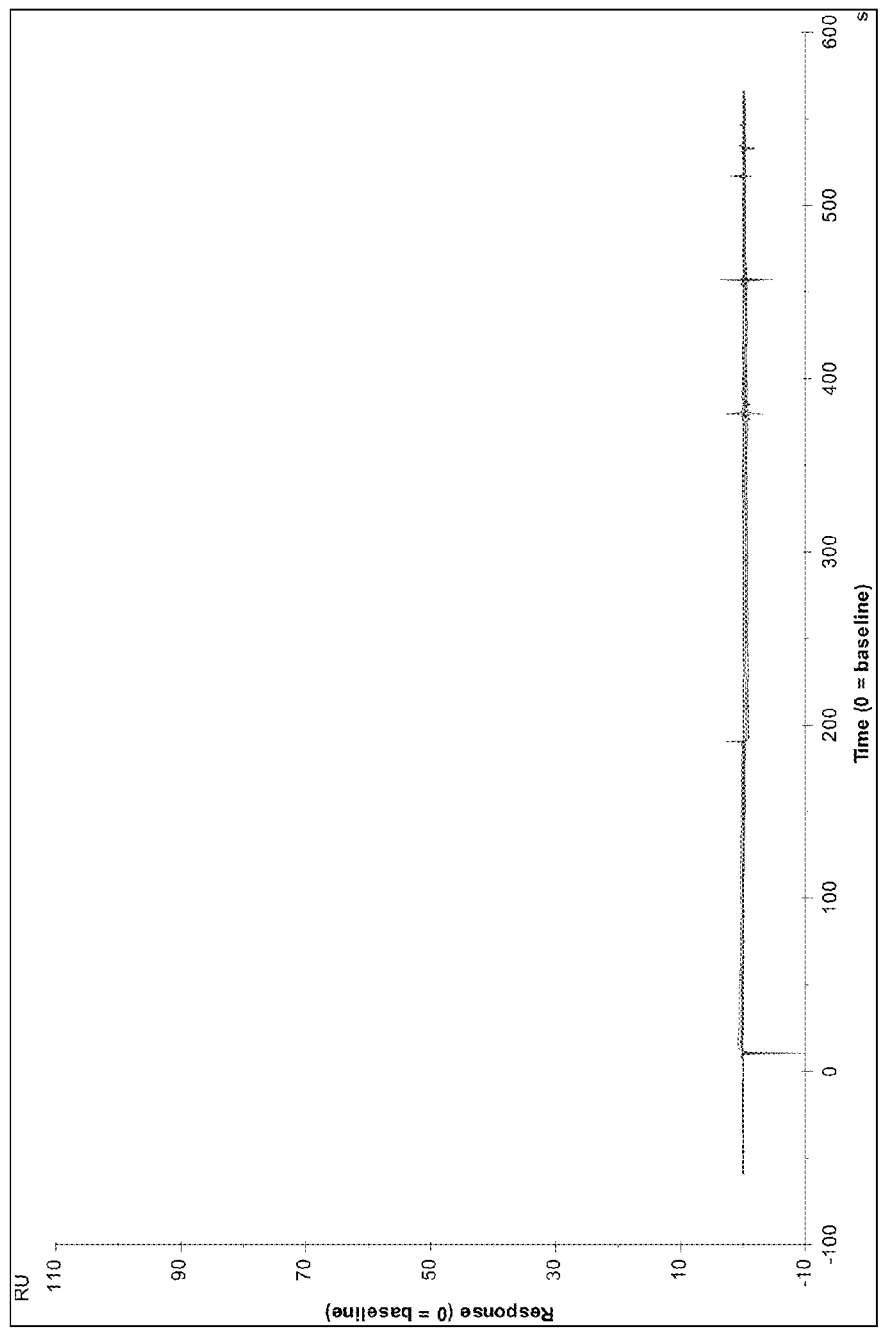
Figure 5D:
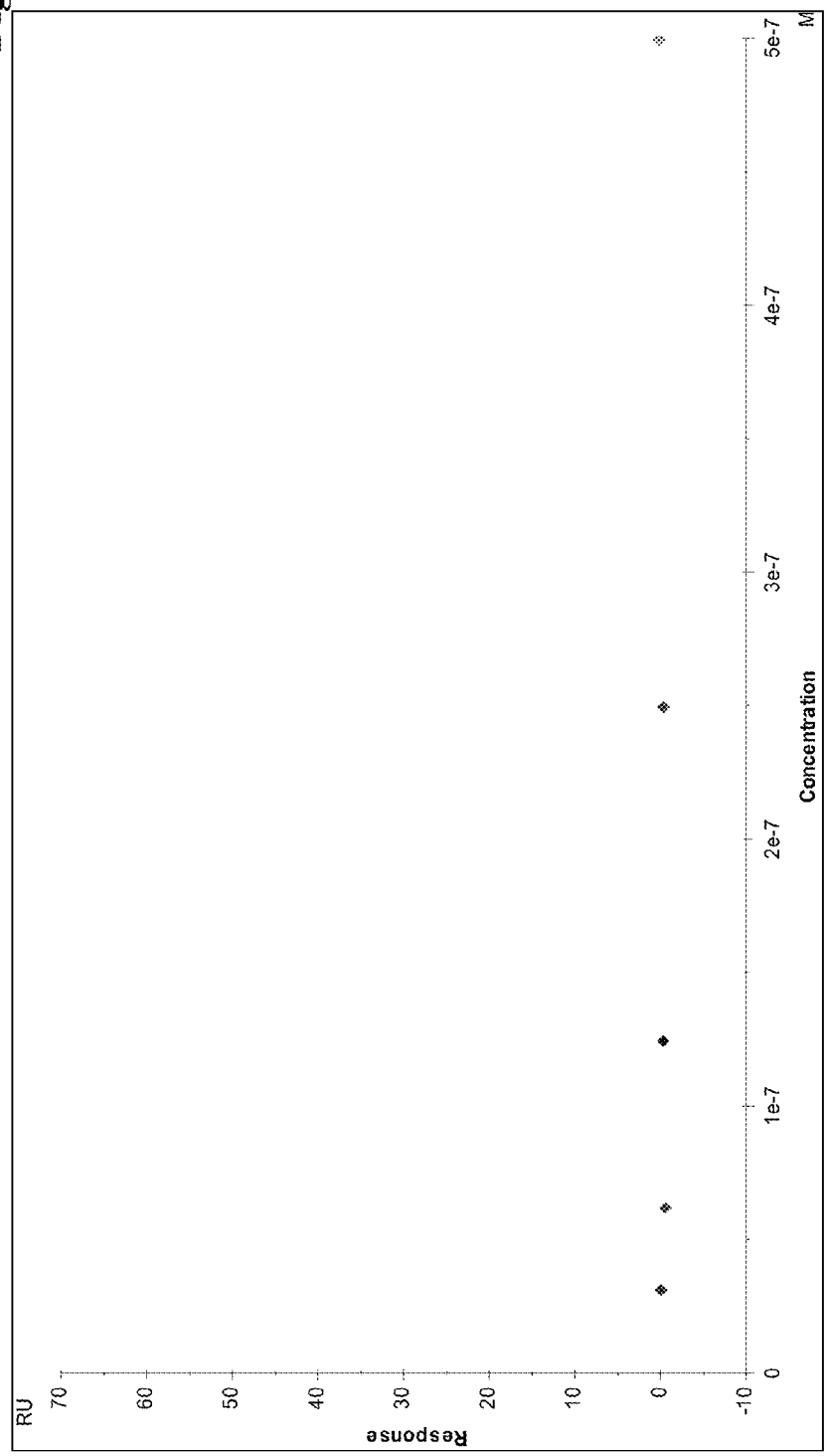
Figure 5E:
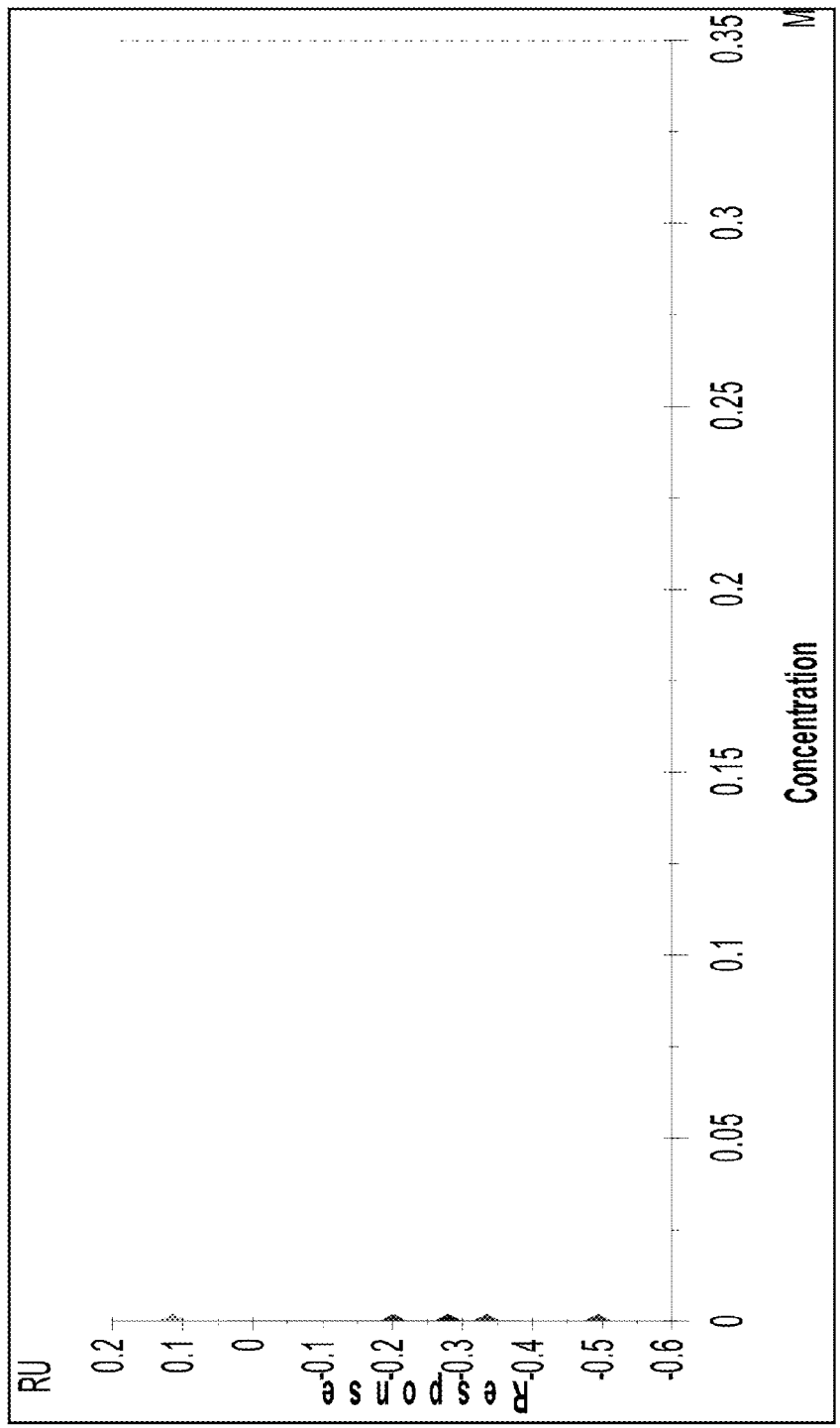

Samples are concentrated to a final concentration of 100 mg/mL in 200 mM arginine succinate, pH 5.5, sterile filtered and quiescently stored at 40° C. for 7 days. Before and after storage, the content of high and low molecular weight species (HMWs and LMWs, respectively) is determined by size-exclusion chromatography. The difference in HMW and LMW content between the stored sample and a sample measured immediately after preparation is reported as "HMW increase" and "LMW increase", respectively. Results are shown in Table 4 and FIG. 4, which show that VEGFang2-0015 (without AAA mutation) shows a higher reduction of the main peak and a higher HMW increase compared to VEGF Ang2-0016 (with AAA mutation). Surprisingly VEGF Ang2-0016 (with AAA mutation) showed a lower aggregation tendency compared to VEGFang2-0015 (without AAA mutation).

TABLE 4

Delta Main-, HMW and LMW peaks after 7 d at 40° C.

|  | delta_area %(40° C.-(−80° C.)) | | |
|---|---|---|---|
|  | Main Peak | HMW | LMW |
| VEGFang2-0015 (−AAA mutations) | −3.56 | 2.89 | 0.67 |
| VEGFang2-0016 (+AAA mutations) | −1.74 | 1.49 | 0.25 |

The functional analysis of anti-VEGF and anti-Ang2 bispecific antibodies was assessed by Surface Plasmon Resonance (SPR) using a BIAcore® T100 or T200 instrument (GE Healthcare) at 25° C. The BIAcore® system is well established for the study of molecule interactions. SPR-technology is based on the measurement of the refractive index close to the surface of a gold coated biosensor chip. Changes in the refractive index indicate mass changes on the surface caused by the interaction of immobilized ligand with analyte injected in solution. The mass increases if molecules bind immobilized ligands on the surface, and vice versa, the mass decreases in case of dissociation of the analyte from the immobilized ligand (reflecting complex dissociation). SPR allows a continuous real-time monitoring of ligand/analyte binding and thus the determination of the association rate constant (ka), the dissociation rate constant (kd), and of the equilibrium constant (KD).

Example 3

Binding to VEGF, Ang2, FcgammaR and FcRn

VEGF Isoforms Kinetic Affinity Including Assessment of Species-Crossreactivity

Around 12000 resonance units (RU) of the capturing system (10 µg/ml goat anti human F(ab)'$_2$; Order Code: 28958325; GE Healthcare Bio-Sciences AB, Sweden) were coupled on a CM5 chip (GE Healthcare BR-1005-30) at pH 5.0 by using an amine coupling kit supplied by the GE Healthcare. The sample and system buffer was PBS-T (10 mM phosphate buffered saline including 0.05% Tween20) pH 7.4. The flow cell was set to 25° C.—and the sample block set to 12° C.—and primed with running buffer twice. The bispecific antibody was captured by injecting a 50 nM solution for 30 sec at a flow of 5 µl/min. Association was measured by injection of human hVEGF121, mouse mVEGF120 or rat rVEGF164 in various concentrations in solution for 300 sec at a flow of 30 µl/min starting with 300 nM in 1:3 dilutions. The dissociation phase was monitored for up to 1200 sec and triggered by switching from the sample solution to running buffer. The surface was regenerated by 60 sec washing with a Glycine pH 2.1 solution at a flow rate of 30 µl/min. Bulk refractive index differences were corrected by subtracting the response obtained from a goat anti human F(ab')$_2$ surface. Blank injections are also subtracted (=double referencing). For calculation of apparent $K_D$ and other kinetic parameters the Langmuir 1:1 model was used. Results are shown in Table 5.

Ang2 Solution Affinity Including Assessment of Species-Crossreactivity

Solution affinity measures the affinity of an interaction by determining the concentration of free interaction partners in an equilibrium mixture. The solution affinity assay involves the mixing of an <VEGF-ANG-2>bispecific antibody, kept at a constant concentration, with a ligand (=Ang2) at varying concentrations. Maximum possible resonance units (e.g. 17000 resonance units (RU)) of an antibody was immobilized on the CM5 chip (GE Healthcare BR-1005-30) surface at pH 5.0 using an amine coupling kit supplied by the GE Healthcare. The sample and system buffer was HBS-P pH 7.4. Flow cell was set to 25° C. and sample block to 12° C. and primed with running buffer twice. To generate a calibration curve increasing concentrations of Ang2 were injected into a BIAcore flowcell containing the immobilized VEGF-ANG-2>bispecific antibody. The amount of bound Ang2 was determined as resonance units (RU) and plotted against the concentration. Solutions of each ligand (11 concentrations from 0 to 200 nM for the VEGF-ANG-2>bispecific antibody) were incubated with 10 nM Ang2 and allowed to reach equilibrium at room temperature. Free Ang2 concentrations were determined from calibration curve generated before and after measuring the response of solutions with known amounts of Ang2. A 4-parameter fit was set with XLfit4 (IDBS Software) using Model 201 using free Ang2 concentration as y-axis and used concentration of antibody for inhibition as x-axis. The affinity was calculated by determining the inflection point of this curve. The surface was regenerated by one time 30 sec washing with a 0.85% $H_3PO_4$ solution at a flow rate of 30 µl/min. Bulk refractive index differences were corrected by subtracting the response obtained from a blank-coupled surface. Results are shown in Table 6.

FcRn Steady State Affinity

For FcRn measurement a steady state affinity was used to compare bispecific antibodies against each other. Human FcRn was diluted into coupling buffer (10 µg/ml, Na-Acetate pH5.0) and immobilized on a C1-Chip (GE Healthcare BR-1005-35) by targeted immobilization procedure using a BIAcore wizard to a final response of 200 RU. Flow cell was set to 25° C. and sample block to 12° C. and primed with running buffer twice. The sample and system buffer was PBS-T (10 mM phosphate buffered saline including 0.05% Tween20) pH 6.0. To assess different IgG concentrations for each antibody, a concentration of 62.5 nM, 125 nM and 250 nM, 500 nM was prepared. Flow rate was set to 30 µl/min and the different samples were injected consecutively onto the chip surface choosing 180 sec association time. The surface was regenerated by injected PBS-T pH 8 for 60 sec at a flow rate of 30 µl/min. Bulk refractive index differences were corrected by subtracting the response obtained from a blank surface. Buffer injections are also subtracted (=double referencing). For calculation of steady state affinity the method from the Bia-Evaluation software was used. Briefly, the RU values (RU max) were plotted against the analysed concentrations, yielding a dose-response curve. Based on a 2-parametric fit, the upper asymptote is calculated, allowing the determination of the half-maximal RU value and hence the affinity. Results are shown in FIG. 5 and Table 7. Analogously the affinity to cyno, mouse and rabbit FcRn can be determined.

FcgammaRIIIa Measurement

Figure 6:
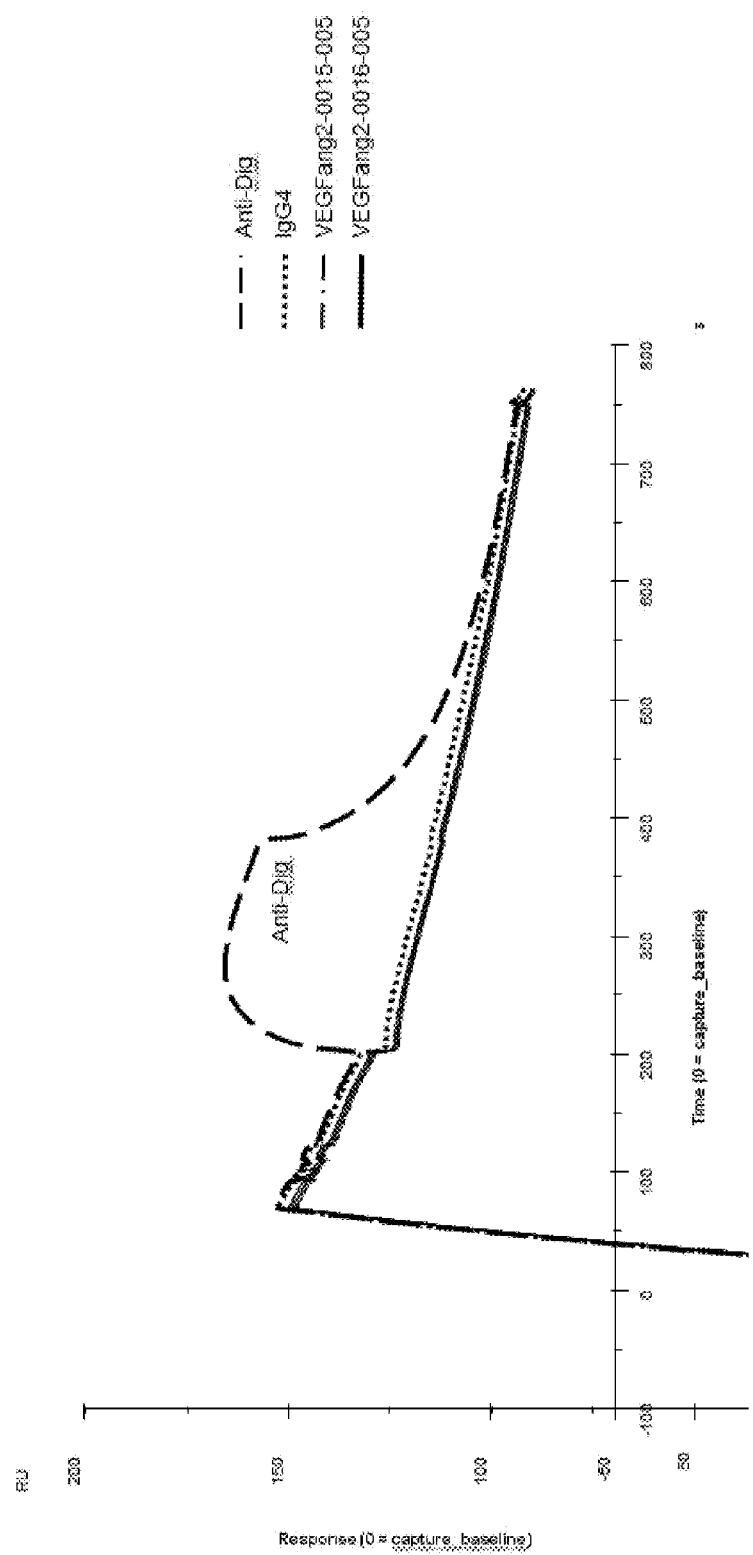
FIG. 6 FcgammaRIIIa interaction of VEGFang2-0015 without AAA mutations and VEGFang2-0016 with AAA mutations measurement (both are IgG1 subclass with P329G LALA mutations; as controls an Anti-Dig of IgG1 subclass and a IgG4 based antibody was used)

For FcgammaRIIIa measurement a direct binding assay was used. Around 3000 resonance units (RU) of the capturing system (1 µg/ml Penta-His; Quiagen) were coupled on a CM5 chip (GE Healthcare BR-1005-30) at pH 5.0 by using an amine coupling kit supplied by the GE Healthcare. The sample and system buffer was HBS-P+pH 7.4. The flow cell was set to 25° C.—and sample block to 12° C.—and primed with running buffer twice. The FcgammaRIIIa-His-receptor was captured by injecting a 100 nM solution for 60 sec at a flow of 5 µl/min. Binding was measured by injection of 100 nM of bispecific antibody or monospecific control antibodies (anti-Dig for IgG1 subclass and an IgG4 subclass antibody) for 180 sec at a flow of 30 µl/. The surface was regenerated by 120 sec washing with Glycine pH 2.5 solution at a flow rate of 30 µl/min. Because FcgammaRIIIa binding differs from the Langmuir 1:1 model, only binding/no binding was determined with this assay. In a similar manner FcgammaRIa, and FcgammaRIIa binding can be determined. Results are shown in FIG. 6, where it follows that by introduction of the mutations P329G LALA no more binding to FcgammaRIIIa could be detected.

Assessment of Independent VEGF- and Ang2-Binding to the <VEGF-ANG-2>Bispecific Antibodies Around 3500 resonance units (RU) of the capturing system (10 µg/ml goat anti human IgG; GE Healthcare Bio-Sciences AB, Sweden) were coupled on a CM4 chip (GE Healthcare BR-1005-34) at pH 5.0 by using an amine coupling kit supplied by the GE Healthcare. The sample and system buffer was PBS-T (10 mM phosphate buffered saline including 0.05% Tween20) pH 7.4. The temperature of the flow cell was set to 25° C. and of the sample block to 12° C. Before capturing, the flow cell was primed with running buffer twice.

The bispecific antibody was captured by injecting a 10 nM solution for 60 sec at a flow of 5 µl/min. Independent binding of each ligand to the bispecific antibody was analysed by determining the active binding capacity for each ligand, either added sequentially or simultaneously (flow of 30 µl/min):
1. Injection of human VEGF with a concentration of 200 nM for 180 sec (identifies the single binding of the antigen).
2. Injection of human Ang2 with a concentration of 100 nM for 180 sec (identifies single binding of the antigen).
3. Injection of human VEGF with a concentration of 200 nM for 180 sec followed by an additional injection of human Ang2 with a concentration of 100 nM for 180 sec (identifies binding of Ang2 in the presence of VEGF).
4. Injection of human Ang2 with a concentration of 100 nM for 180 sec followed by an additional injection of human VEGF with a concentration of 200 nM (identifies binding of VEGF in the presence of Ang2).
5. Co-Injection of human VEGF with a concentration of 200 nM and of human Ang2 with a concentration of 100 nM for 180 sec (identifies the binding of VEGF and of Ang2 at the same time).

The surface was regenerated by 60 sec washing with a 3m MgCl2 solution at a flow rate of 30 µl/min. Bulk refractive index differences were corrected by subtracting the response obtained from a goat anti human IgG surface.

The bispecific antibody is able to bind both antigens mutual independently if the resulting final signal of the approaches 3, 4 & 5 equals or is similar to the sum of the individual final signals of the approaches 1 and 2. Results are shown in Table 9, where both antibodies VEGFang2-0016, VEGFang2-0012 are shown to be able to bind mutual independently to VEGF and ANG2

Assessment of Simultaneous VEGF- and Ang2-Binding to the <VEGF-ANG-2>Bispecific Antibodies First, around 1600 resonance units (RU) of VEGF (20 µg/ml) were coupled on a CM4 chip (GE Healthcare BR-1005-34) at pH 5.0 by using an amine coupling kit supplied by the GE Healthcare. The sample and system buffer was PBS-T (10 mM phosphate buffered saline including 0.05% Tween 20) pH 7.4. Flow cell was set to 25° C. and sample block to 12° C. and primed with running buffer twice. Second, 50 nM solution of the bispecific antibody was injected for 180 sec at a flow of 30 µl/min. Third, hAng-2 was injected for 180 sec at a flow of 30 µl/min. The binding response of hAng-2 depends from the amount of the bispecific antibody bound to VEGF and shows simultaneous binding. The surface was regenerated by 60 sec washing with a 0.85% H3PO4 solution at a flow rate of 30 µl/min. Simultaneous binding is shown by an additional specific binding signal of hAng2 to the previous VEGF bound <VEGF-ANG-2>bispecific antibodies. For both bispecific antibodies VEGFang2-0015 and VEGFang2-0016 simultaneous VEGF- and Ang2-binding to the <VEGF-ANG-2>bispecific antibodies could be detected (data not shown).

TABLE 5

Results: Kinetic affinities to VEGF isoforms from different species

|  | VEGFang2-0015 - apparent affinity | VEGFang2-0016 - apparent affinity | VEGFang2-0012 - apparent affinity | VEGFang2-0201 - apparent affinity |
| --- | --- | --- | --- | --- |
| Human VEGF 121 | ≤1 pM (out of Biacore specification) | ≤1 pM (out of Biacore specification) | ≤1 pM (out of Biacore specification) | ≤1 pM (out of Biacore specification) |
| mouseVEGF 120 | no binding | no binding | no binding | no binding |
| Rat VEGF 164 | 13 nM | 14 nM | 24 nM | 35 nM |

TABLE 6

Results: Solution affinities to Ang2

|  | VEGFang2-0015 KD [nM] | VEGFang2-0016 KD [nM] | VEGFang2-0012 KD [nM] | VEGFang2-0201 KD [nM] |
| --- | --- | --- | --- | --- |
| humanAng2 | 8 | 20 | 20 | tbd |
| cynoAng2 | 5 | 13 | 10 | tbd |
| mouseAng2 | 8 | 13 | 8 | tbd |
| rabbitAng2 | 4 | 11 | 8 | tbd |

TABLE 7

Results: Affinity to FcRn of <VEGF-ANG-2> bispecific antibodies

|  | VEGFang2-0015 [affinity] | VEGFang2-0016 [affinity] | VEGFang2-0012 [affinity] | VEGFang2-0201 [affinity] |
| --- | --- | --- | --- | --- |
| Human FcRn | 0.8 µM | no binding | no binding | 0.8 µM |
| Cyno FcRn | 0.9 µM | no binding | no binding | 1.0 µM |
| Mouse FcRn | 0.2 µM | no binding | no binding | 0.2 µM |

TABLE 8

Results Binding to FcgammaRI - IIIa

|  | VEGFang2-0015 | VEGFang2-0016 | VEGFang2-0012 | VEGFang2-0201 |
| --- | --- | --- | --- | --- |
| FcγRIa | No binding | No binding | Binding | Binding |
| FcγRIIa | No binding | No binding | No binding | Binding |
| FcγRIIIa | No binding | No binding | No binding | Binding |

TABLE 9

Results: Independent binding of VEGF- and Ang2 to <VEGF-ANG-2> bispecific antibodies

|  | 1) Ang2 [RUmax] | 2) VEGF [RUmax] | 3) first VEGF then Ang2 [RUmax] | 4) first Ang2 then VEGF [RUmax] | 5) Coinjection Ang2 + VEGF [RUmax] |
| --- | --- | --- | --- | --- | --- |
| VEGFang2-0016 | 174 | 50 | 211 | 211 | 211 |
| VEGFang2-0012 | 143 | 43 | 178 | 177 | 178 |

Example 4

Mass Spectrometry

This section describes the characterization of <VEGF-ANG-2>bispecific antibodies with emphasis on the correct assembly. The expected primary structures were confirmed by electrospray ionization mass spectrometry (ESI-MS) of the deglycosylated, and intact or IdeS-digested (IgG-degrading enzyme of *S. pyogenes*)<VEGF-ANG-2>bispecific antibodies. The IdeS-digestion was performed with 100 μg purified antibody incubated with 2 μg IdeS protease (Roche) in 100 mmol/L $NaH_2PO_4/Na_2HPO_4$, pH 7.1 at 37° C. for 5 h. Subsequently, the antibodies were deglycosylated with N-Glycosidase F, Neuraminidase and O-glycosidase (Roche) in 100 mmol/L $NaH_2PO_4/Na_2HPO_4$, pH 7.1 at 37° C. for up to 16 h at a protein concentration of 1 mg/ml and subsequently desalted via HPLC on a Sephadex G25 column (GE Healthcare). The total mass was determined via ESI-MS on a maXis 4G UHR-QTOF MS system (Bruker Daltonik) equipped with a TriVersa NanoMate® source (Advion).

The masses obtained for the IdeS-digested, deglycosylated (Table 10), or intact, deglycosylated (Table 11) molecules correspond to the predicted masses deduced from the amino acid sequences for the <VEGF-ANG-2>bispecific antibodies consisting of two different light chains $LC_{Ang2}$ and $LC_{Lucentis}$, and two different heavy chains $HC_{Ang2}$ and $HC_{Lucentis}$.

TABLE 10

Masses of the deglycosylated and IdeS-digested bispecific <VEGF/ANG2> antibodies VEGFang2-0201 (without AAA mutation) and VEGFang2-0012 (with AAA mutation)

| Sample | F(ab')2 of the VEGF-ANG-2> bispecific antibody | | Deglycosylated Fc of the VEGF-ANG-2> bispecific antibody | |
|---|---|---|---|---|
| | Predicted Average Mass [Da] | Observed Average Mass [Da] | Predicted Average Mass [Da] | Observed Average Mass [Da] |
| VEGFang2-0201 | 99360.8 | 99360.7 | 47439.2 | 47430.1 |
| VEGFang2-0012 | 99360.8 | 99361.1 | 47087.7 | 47082.0 |

TABLE 11

Masses of the deglycosylated <VEGF/ANG2> antibodies VEGFang2-0016 (with AAA mutation) and VEGFang2-0015 (without AAA mutation)

| | Deglycosylated VEGF-ANG-2> bispecific antibody | |
|---|---|---|
| | Predicted Average Mass [Da] | Observed Average Mass [Da] |
| VEGFang2-0016 | 146156.9 | 146161.2 |
| VEGFang2-0015 | 146505.3 | 146509.4 |

Example 5

Fc-Rn Chromatography

Coupling to Streptavidin Sepharose:

One gram streptavidin Sepharose® (GE Healthcare) was added to the biotinylated and dialyzed receptor and incubated for two hours with shaking. The receptor derivatized sepharose was filled in a 1 ml XK column (GE Healthcare).

Chromatography Using the FcRn Affinity Column:

Conditions:

column dimensions: 50 mm×5 mm
bed height: 5 cm
loading: 50 μg sample
equilibration buffer: 20 mM MES, with 150 mM NaCl, adjusted to pH 5.5 elution buffer: 20 mM Tris/HCl, with 150 mM NaCl, adjusted to pH 8.8 elution: 7.5 CV equilibration buffer, in 30 CV to 100% elution buffer, 10 CV elution buffer Hu FcRn Affinity Column Chromatography In the following table retention times of <VEGF-ANG-2>bispecific antibodies on affinity columns comprising human FcRn are given. Data were obtained using the conditions above. In the following Table retention times of <VEGF-ANG-2>bispecific antibodies on human FcRn are given.

TABLE 12

Results: retention times of <VEGF-ANG-2> bispecific antibodies

| antibody | retention time [min] |
|---|---|
| VEGFAng2-0015 (without AAA mutation) | 78.5 |
| VEGFAng2-0201 (without AAA mutation) | 78.9 |
| VEGFAng2-0012 (with AAA mutation) | 2.7 (Void-peak) |
| VEGFAng2-0016 (with AAA mutation) | 2.7 (Void-peak) |

Example 6

Pharmacokinetic (PK) Properties

PK Data with Fc-Rn Mice Transgenic for Human FcRn

In Life Phase

The study included female C57BL/6J mice (background); mouse FcRn deficient, but hemizygous transgenic for human FcRn (huFcRn, line 276-/tg)

Part 1

All mice were injected once intravitreally into the right eye with 2 μL/animal of the appropriate solution (i.e. 21 μg compound/animal (VEGFAng2-0015 (without AAA mutation) or 23.6 μg compound/animal (VEGFAng2-0016 (with AAA mutation).

Mice were allocated to 2 groups with 6 animals each. Blood samples are taken from group 1 at 2, 24 and 96 hours and from group 2 at 7, 48 and 168 hours after dosing.

Injection into the vitreous of the right mouse eye was performed by using the NanoFil Microsyringe system for nanoliter injection from World Precision Instruments, Inc., Berlin, Germany. Mice were anesthetized with 2.5% Isoflurane and for visualization of the mouse eye a Leica MZFL 3 microscope with a 40 fold magnification and a ring-light with a Leica KL 2500 LCD lightning was used. Subsequently, 2 μL of the compound were injected using a 35-gauge needle.

Blood was collected via the retrobulbar venous plexus of the contralateral eye from each animal for the determination of the compound levels in serum.

Serum samples of at least 50 μl were obtained from blood after 1 hour at RT by centrifugation (9300×g) at 4° C. for 3 min. Serum samples were frozen directly after centrifugation and stored frozen at −80° C. until analysis. Treated eyes of the animals of group 1 were isolated 96 hours after treatment and of the animals of group 2 168 hours after treatment. Samples were stored frozen at −80° C. until analysis.

Part 2

All mice were injected once intravenously via the tail vein with 200 μL/animal of the appropriate solution (i.e. 21 μg compound/animal (VEGFAng2-0015 (without AAA mutation) or 23.6 μg compound/animal (VEGFAng2-0016 (with AAA mutation).

Mice were allocated to 2 groups with 5 animals each. Blood samples are taken from group 1 at 1, 24 and 96 hours and from group 2 at 7, 48 and 168 hours after dosing. Blood was collected via the retrobulbar venous plexus from each animal for the determination of the compound levels in serum.

Serum samples of at least 50 μl were obtained from blood after 1 hour at RT by centrifugation (9300×g) at 4° C. for 3 min. Serum samples were frozen directly after centrifugation and stored frozen at −80° C. until analysis.

Preparation of Whole Eye Lysates (Mice)

The eye lysates were gained by physico-chemical disintegration of the whole eye from laboratory animals. For mechanical disruption, each eye was transferred into a 1.5-mL micro vial with conical bottom. After freeze and thawing, the eyes were washed with 1 mL cell washing buffer once (Bio-Rad, Bio-Plex Cell Lysis Kit, Cat. No. 171-304011). In the following step, 500 μL of freshly prepared cell lysis buffer were added and the eyes were grinded using a 1.5 mL tissue grinding pestle (Kimble Chase, 1.5 mL pestle, Art. No. 749521-1500). The mixture was then frozen and thawed five times and grinded again. To separate lysate from remaining tissue the samples were centrifuged for 4 min at 4500 g. After centrifuging the supernatant was collected and stored at −20° C. until further analysis in the quantification ELISA.

Analysis

The concentrations of the <VEGF/ANG2>antibodies in mice serum and eye lysates were determined with an enzyme linked immunosorbent assay (ELISA)

For quantification of <VEGF/ANG2>antibodies in mouse serum samples and eye lysates, a standard solid-phase serial sandwich immunoassay with biotinylated and digoxigenated monoclonal antibodies used as capture and detection antibodies was performed. To verify the integrity of the bispecifity of the analyte the biotinylated capture antibody recognizes the anti-VEGF-binding site whereas the digoxigenated detection antibody will bind to the anti-Ang2 binding site of the analyte. The bound immune complex of capture antibody, analyte and detection antibody on the solid phase of the streptavidin coated micro titer plate (SA-MTP) is then detected with a horseradish-peroxidase coupled to an anti-digoxigenin antibody. After washing unbound material from the SA-MTP and addition of ABTS-substrate, the gained signal is proportional to the amount of analyte bound on the solid phase of the SA-MTP. Quantification is then done by converting the measured signals of the samples into concentrations referring to calibrators analyzed in parallel.

In a first step the SA-MTP was coated with 100 μL/well of biotinylated capture antibody solution (mAb<Id<VEGF>>M-2.45.51-IgG-Bi(DDS)) with a concentration of 1 μg/mL for one hour at 500 rpm on a MTP-shaker. Meanwhile calibrators, QC-samples and samples were prepared. Calibrators and QC-samples are diluted to 2% serum matrix; samples were diluted until the signals were within the linear range of the calibrators.

After coating the SA-MTP with capture antibody, the plate was washed three times with washing buffer and 300 μL/well. Subsequently 100 μl/well of the calibrators, QC-samples and samples were pipetted on the SA-MTP and incubated again for one hour at 500 rpm. The analyte was now bound with its anti-VEGF binding site via the capture antibody to the solid phase of the SA-MTP. After incubation and removal of unbound analyte by washing the plate 100 μL/well of the first detection antibody (mAb<Id-<Ang2>>M-2.6.81-IgG-Dig(XOSu)) with a concentration of 250 ng/mL was added to the SA-MTP. Again, the plate was incubated for one hour at 500 rpm on a shaker. After washing, 100 μL/well of the second detection antibody (pAb<Digoxigenin>S-Fab-POD (poly)) at a concentration of 50 mU/mL was added to the wells of the SA-MTP and the plate was incubated again for one hour at 500 rpm. After a final washing step to remove excess of detection antibody, 100 μL/well substrate (ABTS) is added. The antibody-enzyme conjugate catalyzes the color reaction of the ABTS® substrate. The signal was then measured by an ELISA reader at 405 nm wavelength (reference wavelength: 490 nm ([405/490] nm)).

Pharmacokinetic Evaluation

The pharmacokinetic parameters were calculated by non-compartmental analysis, using the pharmacokinetic evaluation program WinNonlin™ (Pharsight), version 5.2.1.

Results: A) Serum Concentrations

Figure 7A:
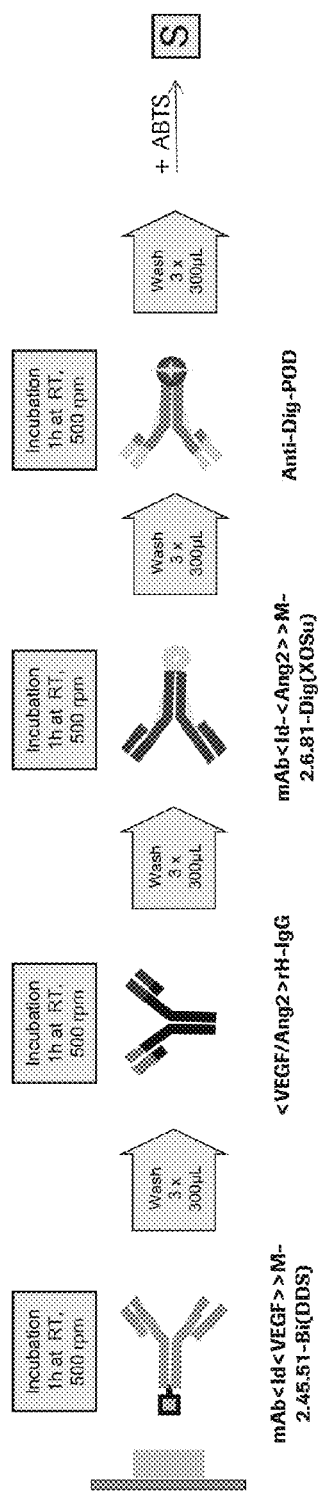
FIG. 7A Schematic Pk-ELISA Assay Principle for determination of concentrations of <VEGF/Ang2>bispecific antibodies in serum and whole eye lysates FIG. 7B Serum concentration after intravenous application: Comparison of compounds—VEGFang2-0015 without AAA mutations and VEGFang2-0016 with AAA mutations FIG. 7C Serum concentration after intravitreal application: Comparison of compounds—VEGFang2-0015 without AAA mutations and VEGFang2-0016 with AAA mutations FIG. 7D Eye lysates concentration of VEGFang2-0016 (with AAA mutation) in right and left eye (after intravitreal application only into the right eye in comparison to intravenous application): Significant concentrations could be detected only in the right eye after intravitreal application. After intravenous application no concentrations in eye lysates could be detected due to the low serum half-life of VEGFang2-0016 (with AAA mutation)
Figure 7B:
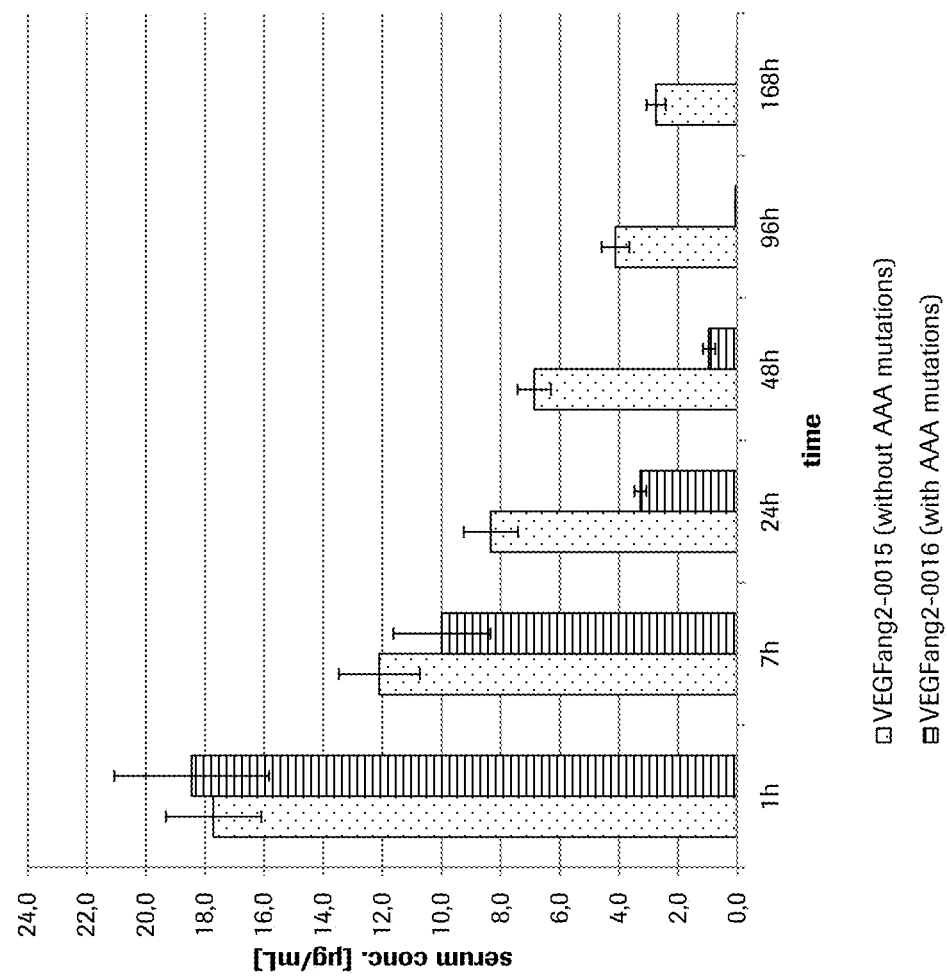
FIG. 7E Eye lysates concentration of VEGFang2-0015 (without AAA mutation) in right and left eye (after intravitreal application only into the right eye in comparison to intravenous application): In the right eye (and to some extent in the left eye) after intravitreal application concentrations of VEGFang2-0015 could be detected. This indicates the diffusion from the right eye into serum and from there into the left eye, which can be explained by the long half-life of VEGFang2-0015 (without AAA mutation). After intravenous application also significant concentrations in eye lysates of both eyes could be detected due to diffusion into the eyes of the serum-stable VEGFang2-0015 (without AAA mutation)
Figure 7C:
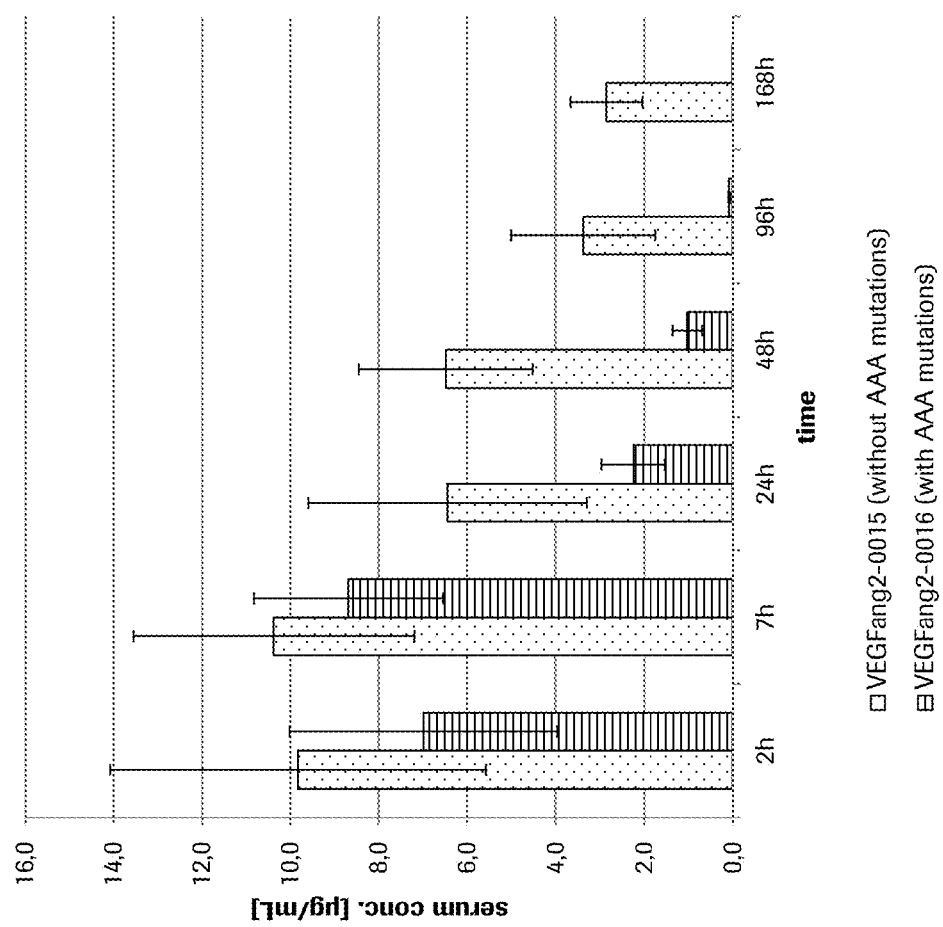

Results for serum concentrations are shown in Tables 13 to 16 and FIG. 7B to 7C

TABLE 13

VEGFAng2-0015 (without AAA mutation): Comparison of serum concentrations after intravitreal and intravenous application

| ID | Serum concentration after intravitreal application Average conc. [μg/mL] | Serum concentration after intravenous application Average conc. [μg/mL] |
|---|---|---|
| 1 h |  | 17.7 |
| 2 h | 9.8 |  |
| 7 h | 10.4 | 12.1 |
| 24 h | 6.4 | 8.3 |
| 48 h | 6.5 | 6.9 |
| 96 h | 3.4 | 4.1 |
| 168 h | 2.9 | 2.7 |

TABLE 14

VEGFAng2-0016 (with AAA mutation): Comparison of serum concentrations after intravitreal and intravenous application

| ID | Serum concentration after intravitreal application Average conc. [μg/mL] | Serum concentration after intravenous application Average conc. [μg/mL] |
|---|---|---|
| 1 h |  | 18.4 |
| 2 h | 7.0 |  |
| 7 h | 8.7 | 10.0 |
| 24 h | 2.2 | 3.3 |
| 48 h | 1.0 | 1.0 |

TABLE 14-continued

VEGFAng2-0016 (with AAA mutation): Comparison of serum concentrations after intravitreal and intravenous application

| ID | Serum concentration after intravitreal application Average conc. [µg/mL] | Serum concentration after intravenous application Average conc. [µg/mL] |
|---|---|---|
| 96 h | 0.1 | 0.1 |
| 168 h | 0.0 | 0.0 |

TABLE 15

VEGFang2-0015 (without AAA mutation) and VEGFang2-0016 (with AAA mutation): Comparison of serum concentrations after intravitreal application)

| ID | VEGFang2-0015 (without AAA mutation) Average conc. [µg/mL] | VEGFang2-0016 (with AAA mutation) Average conc. [µg/mL] |
|---|---|---|
| 2 h | 9.8 | 7.0 |
| 7 h | 10.4 | 8.7 |
| 24 h | 6.4 | 2.2 |
| 48 h | 6.5 | 1.0 |
| 96 h | 3.4 | 0.1 |
| 168 h | 2.9 | 0.0 |

TABLE 16

VEGFang2-0015 (without AAA mutation) and VEGFang2-0016 (with AAA mutation): Comparison of serum concentrations after intravenous application

| ID | VEGFang2-0015 (without AAA mutation) Average conc. [µg/mL] | VEGFang2-0016 (with AAA mutation) Average conc. [µg/mL] |
|---|---|---|
| 1 h | 17.7 | 18.4 |
| 7 h | 12.1 | 10.0 |
| 24 h | 8.3 | 3.3 |
| 48 h | 6.9 | 1.0 |
| 96 h | 4.1 | 0.1 |
| 168 h | 2.7 | 0.0 |

Results: B) Concentrations in Eye-Lysates of Left and Right Eyes

Results for concentrations in eye lysates are shown in Tables 17 to 18 and FIGS. 7D to 7E

TABLE 17a

Concentrations of VEGFang2-0015 (without AAA mutation) in eye lysates after intra vitreal application into right eye
Mean conc. values from n = 6 mice

| ID | | mean conc. [ng/mL] |
|---|---|---|
| 96 h | Left eye | 8.7 |
| | Right eye | 46.1 |
| 168 h | Left eye | 4.3 |
| | Right eye t | 12.9 |

TABLE 17b

Concentrations of VEGFang2-0015 (without AAA mutation) in eye lysates after intravenous application
Mean conc. values from n = 5 mice

| ID | | mean conc. [ng/mL] |
|---|---|---|
| 96 h | Left eye | 4.2 |
| | Right eye | 7.5 |
| 168 h | Left eye | 3.4 |
| | Right eye | 6.1 |

TABLE 18a

Concentrations of VEGFang2-0016 (with AAA mutation) in eye lysates after intra vitreal application into right eye
Mean conc. values from n = 5 mice

| ID | | mean conc. [ng/mL] |
|---|---|---|
| 96 h | Left eye | 0.3 |
| | Right eye | 34.5 |
| 168 h | Left eye | 0.1 |
| | Right eye | 9.0 |

TABLE 18b

Concentrations of VEGFang2-0016 (with AAA mutation) in eye lysates after intravenous application
Mean conc. values from n = 5 mice

| ID | | mean conc. [ng/mL] |
|---|---|---|
| 96 h | Left eye | 0.0 |
| | Right eye | 0.1 |
| 168 h | Left eye | 0.0 |
| | Right eye | 0.1 |

Summary of Results:

After intravitreal application the bispecific <VEGF/ANG2>antibody according to the invention VEGFang2-0016 (with AAA mutation) shows similar concentrations (after 96 and 168 hours) in the eye lysates as compared to the bispecific <VEGF/ANG2>antibody without AAA mutation VEGFang2-0015.

Also after intravitreal application the bispecific <VEGF/ANG2>antibody according to the invention VEGFang2-0016 (with AAA mutation) shows in addition a faster clearance and shorter half-life in the serum as compared to the bispecific <VEGF/ANG2>antibody without AAA mutation VEGFang2-0015.

Example 7

Mouse Cornea Micropocket Angiogenesis Assay

To test the anti-angiogenic effect bispecific <VEGF/ANG2>antibody with the respective anti-VEGF VH and VL of SEQ ID NO: 7 and 8 and the anti-ANG2 VH and VL of SEQ ID NO: 15 and 16 on VEGF-induced angiogenesis in vivo, we perform the mouse corneal angiogenesis assay. In this assay a VEGF soaked Nylaflo® disc is implanted into a pocket of the avascular cornea at a fixed distance to the limbal vessels. Vessels immediately grow into the cornea towards the developing VEGF gradient. 8 to 10 weeks old female Balb/c mice were purchased from Charles River, Sulzfeld, Germany. The protocol is modified according to the method described by Rogers, M.S., et al., Nat. Protoc. 2 (2007) 2545-2550. Briefly, micropockets with a width of about 500 μm are prepared under a microscope at approximately 1 mm from the limbus to the top of the cornea using a surgical blade and sharp tweezers in the anesthetized mouse. The disc (Nylaflo®, Pall Corporation, Michigan) with a diameter of 0.6 mm is implanted and the surface of the implantation area was smoothened. Discs are incubated in corresponding growth factor or in vehicle for at least 30 min. After 3, 5 and 7 days (or alternatively only after 3, 5 or 7 days), eyes are photographed and vascular response is measured. The assay is quantified by calculating the percentage of the area of new vessels per total area of the cornea.

The discs are loaded with 300 ng VEGF or with PBS as a control and implanted for 7 days. The outgrowth of vessels from the limbus to the disc is monitored over time on day 3, 5 and/or 7. One day prior to disc implantation the antibodies are administered intravenously at a dose of 10 mg/kg (due to the intravenous application the serum-stable VEGFang2-0015 (without AAA mutation) which only differs from VEGFang2-0016 by the AAA mutation and has the same anti-VEGF and anti-ANG2 VHs and VLs to mediate efficacy, is used as surrogate) for testing the anti-angiogenic effect on VEGF-induced angiogenesis in vivo. Animals in the control group receive vehicle. The application volume is 10 ml/kg.

The invention claimed is:

1. A bispecific antibody comprising a first antigen-binding site that specifically binds to human vascular endothelial growth factor (VEGF) and a second antigen-binding site that specifically binds to human angiopoietin-2 (ANG-2), wherein
   i) said first antigen-binding site specifically binding to VEGF comprises as heavy chain variable domain VH an amino acid sequence of SEQ ID NO: 7, and as light chain variable domain VL an amino acid sequence of SEQ ID NO: 8, and
   ii) said second antigen-binding site specifically binding to ANG-2 comprises as heavy chain variable domain VH an amino acid sequence of SEQ ID NO: 15, and as light chain variable domain VL an amino acid sequence of SEQ ID NO: 16, and wherein
   iii) the bispecific antibody comprises a constant heavy chain region of human IgG1 or human IgG4 subclass comprising the mutations I253A, H310A, and H435A (numbering according to EU Index of Kabat).

2. The bispecific antibody according to claim 1, wherein the constant heavy chain region under iii) is of IgG1 subclass.

3. The bispecific antibody according to claim 1, wherein the constant heavy chain region of IgG1 subclass further comprises the mutations L234A L235A and P329G (numbering according to EU Index of Kabat).

4. The bispecific antibody according to claim 1, wherein the constant heavy chain region under iii) is of IgG4 subclass.

5. The bispecific antibody according to claim 4, wherein the constant heavy chain region of IgG4 subclass further comprises the mutations S228P and L235E (numbering according to EU Index of Kabat).

6. The bispecific antibody according to claim 4, wherein the constant heavy chain region of IgG4 subclass further comprises the mutations S228P L235E and P329G (numbering according to EU Index of Kabat).

7. A pharmaceutical composition comprising the antibody according to any one of claims 1 to 6.

8. A bispecific antibody according to claim 1 obtained by a method comprising the steps of
   a) transforming a host cell with vectors comprising nucleic acid molecules encoding said antibody;
   b) culturing the host cell under conditions that allow synthesis of said antibody molecule; and
   c) recovering said antibody molecule from said culture.

9. A bispecific, bivalent antibody comprising a first antigen-binding site that specifically binds to human VEGF and a second antigen-binding site that specifically binds to human ANG-2, wherein the antibody comprises a first heavy chain comprising the amino acid sequence of SEQ ID NO: 25, a first light chain comprising the amino acid sequence of SEQ ID NO: 27, a second heavy chain comprising the amino acid sequence of SEQ ID NO: 26, and a second light chain comprising the amino acid sequence of SEQ ID NO: 28.

10. A bispecific, bivalent antibody comprising a first antigen-binding site that specifically binds to human VEGF and a second antigen-binding site that specifically binds to human ANG-2, wherein the antibody comprises a first heavy chain comprising the amino acid sequence of SEQ ID NO: 21, a first light chain comprising the amino acid sequence of SEQ ID NO: 23, a second heavy chain comprising the amino acid sequence of SEQ ID NO: 22, and a second light chain comprising the amino acid sequence of SEQ ID NO: 24.

11. A bispecific, bivalent antibody comprising a first antigen-binding site that specifically binds to human VEGF and a second antigen-binding site that specifically binds to human ANG-2, wherein the antibody comprises a first heavy chain comprising the amino acid sequence of SEQ ID NO: 29, a first light chain comprising the amino acid sequence of SEQ ID NO: 31, a second heavy chain comprising the amino acid sequence of SEQ ID NO: 30, and a second light chain comprising the amino acid sequence of SEQ ID NO: 32.

* * * * *